(12) United States Patent  
Casscells, III et al.

(10) Patent No.: US 7,426,409 B2  
(45) Date of Patent: *Sep. 16, 2008

(54) METHOD AND APPARATUS FOR DETECTING VULNERABLE ATHEROSCLEROTIC PLAQUE

(75) Inventors: S. Ward Casscells, III, Houston, TX (US); James T. Willerson, Houston, TX (US); Morteza Naghavi, Houston, TX (US); Bujin Guo, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 984 days.

This patent is subject to a terminal disclaimer.

(21) Appl. No.: 10/212,860

(22) Filed: Aug. 5, 2002

(65) Prior Publication Data

US 2003/0171691 A1 Sep. 11, 2003

Related U.S. Application Data

(63) Continuation of application No. 09/340,089, filed on Jun. 25, 1999, now Pat. No. 6,615,071.

(51) Int. Cl.
  *A61B 1/00* (2006.01)
  *A61B 1/04* (2006.01)
  *A61B 6/00* (2006.01)
(52) U.S. Cl. .................. 600/474; 600/101; 600/116; 600/473; 607/122
(58) Field of Classification Search .......... 600/549; 606/192
See application file for complete search history.

(56) References Cited

U.S. PATENT DOCUMENTS 3,273,395 A 9/1966 Schwarz (Continued)

FOREIGN PATENT DOCUMENTS

EP 0392897 A3 10/1990

(Continued)

OTHER PUBLICATIONS

Belli, James A., et al. Influence of Temperature on the Radiation Response of Mammalian Cells in Tissue Culture, Radiation Research, 18, 272-276 (1963).

(Continued)

*Primary Examiner*—Brian L. Casler
*Assistant Examiner*—James Kish
(74) *Attorney, Agent, or Firm*—Conley Rose, P.C.

(57) ABSTRACT

Methods and devices are disclosed for detecting vulnerable atherosclerotic plaque, or plaque at risk of reducing blood flow in a vessel, by identifying a region of elevated temperature along a living vessel wall. The disclosure that human atherosclerotic plaque with measurable temperature heterogeneity has the morphological characteristics of plaque that is likely to ulcerate provides a new and sensitive technique for detecting and treating these dangerous plaques before myocardial infarction and its consequences occur. The disclosed methods are advantageous over conventional plaque detection techniques because they are capable of differentiating between those plaques that are at great risk of rupture, fissure, or ulceration, and consequent thrombosis and occlusion of the artery, and those that are not presently at risk. Infrared heat-sensing catheters useful for identifying potentially fatal arterial plaques in patients with disease of the coronary or other arteries are also described. In some embodiments a coherent infrared fiber optic bundle is employed to radially and longitudinally explore a luminal wall to identify inflamed, heat-producing, atherosclerotic plaque. Certain other methods and devices are disclosed which are particularly suited for non-invasively identifying and then monitoring the progression or amelioration of an inflamed plaque in a patient, and for monitoring for onset of inflammation in an implanted arteriovenous graft. Also disclosed are thermocouple basket catheters and thermistor basket catheters which are also capable of detecting temperature heterogeneity along a vessel wall.

20 Claims, 36 Drawing Sheets
(15 of 36 Drawing Sheet(s) Filed in Color)

U.S. PATENT DOCUMENTS

| | | | |
|---|---|---|---|
| 3,638,640 A | 2/1972 | Shaw | |
| 3,866,599 A | 2/1975 | Johnson | |
| 3,913,568 A | 10/1975 | Carpenter | |
| 4,005,605 A | 2/1977 | Michael | |
| 4,200,110 A | 4/1980 | Peterson et al. | |
| 4,281,645 A | 8/1981 | Jöbsis | |
| RE32,204 E | 7/1986 | Halvorsen | |
| 4,602,642 A | 7/1986 | O'Hara et al. | |
| 4,691,709 A | 9/1987 | Cohen | |
| 4,699,147 A * | 10/1987 | Chilson et al. | 600/374 |
| 4,718,417 A * | 1/1988 | Kittrell et al. | 606/7 |
| 4,752,141 A | 6/1988 | Sun et al. | |
| 4,776,334 A | 10/1988 | Prionas | |
| 4,777,955 A | 10/1988 | Brayton et al. | |
| 4,784,149 A | 11/1988 | Berman et al. | |
| 4,790,324 A | 12/1988 | O'Hara et al. | |
| 4,794,931 A | 1/1989 | Yock | |
| 4,797,840 A | 1/1989 | Fraden | |
| 4,799,479 A | 1/1989 | Spears | |
| 4,841,981 A | 6/1989 | Tanabe et al. | |
| 4,849,885 A | 7/1989 | Stillwagon et al. | |
| 4,862,887 A | 9/1989 | Weber et al. | |
| 4,986,671 A | 1/1991 | Sun et al. | |
| 4,995,398 A | 2/1991 | Turnidge | |
| 4,997,431 A | 3/1991 | Isner et al. | |
| 5,000,185 A | 3/1991 | Yock | |
| 5,046,501 A | 9/1991 | Crilly | |
| 5,057,105 A | 10/1991 | Malone et al. | |
| 5,106,387 A | 4/1992 | Kittrell et al. | |
| 5,109,859 A | 5/1992 | Jenkins | |
| 5,174,299 A | 12/1992 | Nelson | |
| 5,197,470 A | 3/1993 | Helfer et al. | |
| 5,217,456 A | 6/1993 | Narciso, Jr. | |
| 5,233,515 A | 8/1993 | Cosman | |
| 5,237,996 A | 8/1993 | Waldman et al. | |
| 5,275,594 A | 1/1994 | Baker et al. | |
| 5,279,565 A | 1/1994 | Klein et al. | |
| 5,282,813 A | 2/1994 | Redha | |
| 5,293,872 A | 3/1994 | Alfano et al. | |
| 5,304,173 A | 4/1994 | Kittrell et al. | |
| 5,313,949 A | 5/1994 | Yock | |
| 5,336,178 A | 8/1994 | Kaplan et al. | |
| 5,355,880 A | 10/1994 | Thomas et al. | |
| 5,373,849 A | 12/1994 | Maroney et al. | |
| 5,400,788 A | 3/1995 | Dias et al. | |
| 5,439,000 A | 8/1995 | Gunderson et al. | |
| 5,439,003 A | 8/1995 | Schnurer et al. | |
| 5,445,157 A | 8/1995 | Adachi et al. | |
| 5,453,448 A | 9/1995 | Narciso, Jr. | |
| 5,496,271 A | 3/1996 | Burton et al. | |
| 5,542,915 A | 8/1996 | Edwards et al. | |
| 5,547,472 A | 8/1996 | Onishi et al. | |
| 5,558,093 A | 9/1996 | Pomeranz | |
| 5,582,170 A | 12/1996 | Soller | |
| 5,596,995 A | 1/1997 | Sherman et al. | |
| 5,606,974 A | 3/1997 | Castellano et al. | |
| 5,611,338 A | 3/1997 | Gallup et al. | |
| 5,620,438 A | 4/1997 | Amplatz et al. | |
| 5,623,940 A | 4/1997 | Daikuzono | |
| 5,682,899 A | 11/1997 | Nashef et al. | |
| 5,708,275 A | 1/1998 | Rhodes | |
| 5,733,739 A | 3/1998 | Zakim et al. | |
| 5,782,239 A * | 7/1998 | Webster, Jr. | 600/374 |
| 5,792,050 A | 8/1998 | Alam et al. | |
| 5,836,947 A * | 11/1998 | Fleischman et al. | 606/47 |
| 5,849,028 A | 12/1998 | Chen | |
| 5,853,411 A * | 12/1998 | Whayne et al. | 606/41 |
| 5,871,449 A * | 2/1999 | Brown | 600/474 |
| 5,924,997 A * | 7/1999 | Campbell | 600/549 |
| 5,935,075 A | 8/1999 | Casscells et al. | |
| 6,014,579 A * | 1/2000 | Pomeranz et al. | 600/374 |
| 6,023,638 A * | 2/2000 | Swanson | 600/510 |
| 6,036,689 A * | 3/2000 | Tu et al. | 606/41 |
| 6,233,491 B1 * | 5/2001 | Kordis et al. | 607/122 |
| 6,245,026 B1 | 6/2001 | Campbell et al. | |
| 6,263,248 B1 * | 7/2001 | Farley et al. | 607/98 |
| 6,450,971 B1 | 9/2002 | Andrus et al. | |
| 6,475,210 B1 | 11/2002 | Phelps et al. | |
| 6,500,172 B1 | 12/2002 | Panescu et al. | |
| 6,511,478 B1 | 1/2003 | Burnside et al. | |
| 6,514,214 B2 | 2/2003 | Kokate et al. | |
| 6,529,756 B1 * | 3/2003 | Phan et al. | 600/374 |
| 6,536,949 B1 | 3/2003 | Heuser | |
| 6,554,801 B1 | 4/2003 | Steward et al. | |
| 6,615,071 B1 * | 9/2003 | Casscells et al. | 600/474 |
| 6,763,261 B2 * | 7/2004 | Casscells et al. | 600/474 |
| 2001/0047137 A1 | 11/2001 | Moreno et al. | |
| 2001/0047138 A1 | 11/2001 | Kokate et al. | |
| 2001/0053882 A1 | 12/2001 | Haddock et al. | |
| 2002/0045816 A1 | 4/2002 | Atalar et al. | |
| 2002/0067754 A1 | 6/2002 | Werneth | |
| 2002/0068928 A1 | 6/2002 | Werneth | |
| 2002/0071474 A1 | 6/2002 | Werneth | |
| 2002/0077564 A1 | 6/2002 | Campbell et al. | |
| 2002/0082515 A1 | 6/2002 | Campbell et al. | |
| 2002/0087079 A1 | 7/2002 | Kaufman et al. | |
| 2002/0107511 A1 | 8/2002 | Collins et al. | |
| 2002/0111560 A1 | 8/2002 | Kokate et al. | |
| 2002/0198465 A1 | 12/2002 | Fox et al. | |
| 2003/0009875 A1 | 1/2003 | Saadat | |
| 2003/0013983 A1 | 1/2003 | Saadat | |
| 2003/0013984 A1 | 1/2003 | Saadat | |
| 2003/0013985 A1 | 1/2003 | Saadat | |
| 2003/0013986 A1 | 1/2003 | Saadat | |
| 2003/0013987 A1 | 1/2003 | Saadat | |
| 2003/0028114 A1 | 2/2003 | Casscells, III et al. | |
| 2003/0055307 A1 | 3/2003 | Elmaleh et al. | |
| 2003/0082105 A1 | 5/2003 | Fischman et al. | |
| 2003/0088187 A1 | 5/2003 | Saadat et al. | |
| 2003/0088420 A1 | 5/2003 | alSafadi et al. | |

FOREIGN PATENT DOCUMENTS

| | | |
|---|---|---|
| EP | 0856278 A2 | 8/1998 |
| EP | 0856278 A3 | 8/1998 |
| EP | 1025797 A1 | 8/2000 |
| EP | 1281350 A1 | 2/2003 |
| EP | 1294275 | 3/2003 |
| EP | 0392897 B1 | 12/2003 |
| GR | 649410 | 1/1976 |
| WO | WO 8902718 | 4/1989 |
| WO | WO 8911311 | 11/1989 |
| WO | WO 9415529 | 7/1994 |
| WO | WO 9502362 | 1/1995 |
| WO | WO 9710748 | 3/1997 |
| WO | WO 0019889 | 4/2000 |
| WO | WO 0027278 | 5/2000 |
| WO | WO 0154581 | 8/2001 |
| WO | WO 0174263 | 10/2001 |
| WO | WO 0195787 A2 | 12/2001 |
| WO | WO 0195787 A3 | 12/2001 |
| WO | WO 0215780 | 2/2002 |
| WO | WO 0228276 | 4/2002 |
| WO | WO 0239080 | 5/2002 |
| WO | WO 02069795 | 9/2002 |
| WO | WO 02078535 | 10/2002 |
| WO | WO 02089871 | 11/2002 |
| WO | WO 03011125 | 2/2003 |

OTHER PUBLICATIONS

Bellocq et al. J. Biol Chem 273:5086-5092 (1998).

Berliner, Judith A., et al. Atherosclerosis: Basic Mechanisms—Oxidation, Inflammation, and Genetics, Circultaion, vol. 91, No. 9, May 1, 1995, pp. 2488-2496.

Biffl, Walter L., et al. Interleukin-6 Delays Neutrophil Apoptosis, Arch Surg/vol. 141, Jan. 1996, pp. 24-30.

Blackburn, M.J., et al. The Sensitivity to Hyperthermia of Human Granulocyte/Macrophage Progenitor Cells (CFU-GM) Derived from Blood or Marrow of Normal Subjects and Patients with Chronic Granulocytic Leukaemia, Br. J. Cancer (1984), 50, 745-751.

Buja et al., Role of Inflammation in Coronary Plaque Disruption, pp. 503-505, Circulation, vol. 89, No. 1, Jan. 1994.

Carney et al. Near-Infrared Spectrophotometric Monitoring of Stroke-Related Changes in the Protein and Lipid Composition of Whole Gerbil Brains, Anal. Chem. 65:1305-1313 (1993).

Casscells, et al. Thermal Detection of Cellular Infiltrates in Living Atherosclerotic Plaques: Possible Implications for Plaque Rupture and Thrombosis, pp. 1447-1449, The Lancet, vol. 347, May 25, 1996.

Cassis, et al. Near-IR Imaging of Atheromas in Living Arterial Tissue, Anal. Chem. 65:1247-56 (1993).

Chen, Ben D-M., et al. Induction of Prostaglandin Production by Hyperthermia in Murine Peritoneal Exudate Macrophages, Cancer Research 47, 11-15, Jan. 1, 1987.

De Vries, et al. Acute Effects of Oxidized Low Density Lipoprotein on Metabolic Responses in Macrophages FASEB J. 12:111-118 (1998).

Dempsey, R.J., et al. Near-Infrared Imaging and Spectroscopy in Stroke Research: Lipoprotein Distribution and Disease, Annals New York Academy of Sciences pp. 149-169 [Lodder@pop.uky.edu][http://kerouac.pharm.uky,edu/ASRG/Wave/Lipo/lipo.htm].

Elkon, David, et al. Thermal Inactivation Energy of Granulocyte-Monocyte Stem Cells, Radiation Research 87, 368-372 (1981).

Ensor, Jeffrey E., et al. Warming Macrophages to Febrile Range Destabilizes Tumor Necrosis Factor-α mRNA Without Inducing Heat Shock, Am. J. Physiol. 269:C1140-C1146 (1995).

Falk, et al., Coronary Plaque Disruption, pp. 657-671, Circulation, vol. 92, No. 3, Aug. 1, 1995.

Field, S.B., et al. The Relationship Between Heating Time and Temperature: Its Relevance to Clinical Hyperthermia, Radiotherapy and Oncology, 1 (1983) 179-186.

Fouqueray, Bruno, et al. Heat Shock Prevents Lipopolysaccharide-Induced Tumor Necrosis Factor-α Synthesis by Rat Mononuclear Phagocytes, Eur. J. Immunol. 1992, 22:2983-2987.

Gerweck, Leo E., et al. Influence of Nutrient and Energy Deprivation on Cellular Response to Single and Fractionated Heat Treatments, Radiation Research 99, 573-581 (1984).

Gronholdt, et al. Eur. Heart J. 19 Supp C:C24-C29 (1998).

Hamilton, Raymond F., et al. Bleomycin Induces Apoptosis in Human Alveolar Macrophages, Am. J. Physiol. 269: L317-L325, 1995.

Haveman, J., et al. The Role of Energy in Hyperthermia-Induced Mammalian Cell Inactivation: A Study of the Effects of Glucose Starvation and An Uncoupler of Oxidative Phosphorylation, Journal of Cellular Physiology 107:237-241 (1981).

Kim, Young-Myeong, et al. Nitric Oxide Protects Cultured Ray Hepatocytes from Tumor Necrosis Factor-α-Induced Apoptosis by Inducing Heat Shock Protein 70 Expression, vol. 272. No. 2 Issue of Jan. 10, pp. 1402-1411, (1997).

Kobayashi, Eiji, et al. Cell Cycle-Dependent Heat Sensitization of Murine Granulocyte-Macrophage Progenitor Cells in Regenerating Marrow, Cancer Research 45, 1459-1463, Apr. 1985.

Kunkel, S.L., et al. Regulation of Macrophage Tumor Necrosis Factor Production by Prostaglandin $E_2$, Biochemical and Biophysical Research Communications, vol. 137, No. 1., May 29, 1986, pp. 404-410.

Lippman, Richard D., Rapid in Vitro Quantification and Comparison of Hydroperoxides and Oxidized Collagen in Aging Mice, Rabbits and Man, Exp. Geron. 20:1-5 (1985).

Liu et al. Modification of the Extracellular Matrix Following Myocardial Infarction Monitored by FTIR Spectroscopy; Biochim. Biophys. Acta. 1315:73-77 (1996).

Mangan, Dennis F., Lipopolysaccharide, Tumor Necrosis Factor-α, and IL-1β Prevent Programmed Cell Death (Apoptosis) in Human Peripheral Blood Monocytes, The Journal of Immunology, vol. 146, 1541-1546, No. 5, Mar. 1, 1991.

Morange, M., et al. Interferon Pretreatment Lowers the Threshold for Maximal Heat-Shock Response in Mouse Cells, Journal of Cellular Physiology, 127:417-422 (1986).

McShane, et al. Near-Infrared Spectroscopy for Determination of Glucose, Lactate, and Ammonia in Cell Culture Media, Appl. Spectroscopy 52:1073-1078 (1998).

Muller, et al., Triggers, Acute Risk Factors and Vulnerable Plaques: The Lexicon of a New Frontier, pp. 809-813, JACC, vol. 23, No. 3, Mar. 1, 1994.

Morteza Nagahavi, Said Siadaty, James T. Willerson, Ward Casscells, University of Texas Houston, School of Medicine TX; Thermosensor Catheter; a Nitinol Shape Memory Basket Catheter to Measure Temperature of Vessel Wall with Continuous Blood Flow Abstract No. 862-1, The Journal of the American College of Cardiology, Feb. 2000.

Nagata, Shigekazu, et al. The Fas Death Factor, Science, vol. 267, Mar. 10, 1995, pp. 1449-1456.

Nishina, Hiroshi, et al. Stress-Signalling Kinase Sek1 Protects Thymocytes From Apoptosis Mediated by CD95 and CD3, Nature, vol. 385, Jan. 23, 1997, pp. 350-353.

Ohdan, et al. New Technique Using Near-Infrared Spectroscopy for Quantifying Nitric Oxide During Acute Rejection of Liver Allograft, Transplantation 57:1674-1677 (1994).

Ohdan et al. Simultaneous Evaluation of Nitric Oxide Synthesis and Tissue Oxygenation in Rat Liver Allograft Rejection Using Near-Infrared Spectroscopy Transplantation 60:531-535 (1995).

Papadimitriou, J.M., et al. Quantitative Investigations of Apoptosis of Murine Mononuclear Phagocytes During Mild Hyperthermia, Experimental and Molecular Pathology 59, 1-12 (1993).

Patterson et al. Human Serum, Cysteine and Histidine Inhibit the Oxygenation of Low Density Lipoprotein Less at Acidic pH, FEBS Lett. 434:317-321 (1998).

Pizurki, Lara, et al. cAMP Modulates Stress Protein Synthesis in Human Monocytes-Macrophages, Journal of Cellular Physiology, 161:169-177 (1994).

Prins, Johannes B., et al. Apoptosis of Human Adipocytes in Vitro, Biochemical and Biophysical Research Communications, vol. 201, No. 2, (1994), pp. 500-507.

Reddy, M. Venkata, et al. Heat Shock Treatment of Macrophages Causes Increased Release of Superoxide Anion, Infection and Immunity, Jun. 1992, vol. 60, No. 6, pp. 2386-2390.

Ribeiro, Sergio P., et al. Effects of the Stress Response in Septic Rats and LPS-Stimulated Alveolar Macrophages: Evidence for TNF-α Posttranslational Regulation, Am. J. Respir. Crit. Car. Med. 1996: 154: 1843-1850.

Robinson, M.R. et al. Noninvasive Glucose Monitoring in Diabetic Patients: A Preliminary Evaluation Clin. Chem. 38:1618-1622 (1992).

Sivo, Judit et al. Heat Shock Mimics Glucocorticoid Effects on IFN-γ-Induced FcγRI and Ia Messenger RNA Expression in Mouse Peritoneal Macrophages, The Journal of Immunology, 1996, pp. 3450-3454.

Snyder, Yvonne M., et al. Transcriptional Inhibition of Endotoxin-Induced Monokine Synthesis Following Heat Shock in Murine Peritoneal Macrophages, Journal of Leukocyte Biology, vol. 51, Feb. 1992, pp. 181-187.

Thompson, Craig B. Apoptosis in the Pathogenesis and Treatment of Disease, Science, vol. 267, Mar. 10, 1995, pp. 1456-1462.

van der Wal, Allard C., et al. Site of Intimal Rupture or Erosion of Thrombosed Coronary Atherosclerotic Plaques is Characterized by an Inflammatory Process Irrespective of the Dominant Plaque Morphology, pp. 36-44, Circulation, vol. 89, No. 1, Jan. 1994.

Vaux, D.L., et al. The Molecular Biology of Apoptosis, Proc. Natl. Acad. Sci. USA, vol. 93, pp. 2239-2244, Mar. 1996.

Verheij, Marcel, et al. Requirement for Ceramide-Initiated SAPK/JNK Signalling in Stress-Induced Apoptosis, Nature, vol. 380, Mar. 1996, pp. 75-79.

Wang, Jiang Huai, et al. Induction of Heat Shock Protein 72 Prevents Neutrophil-Mediated Human Endothelial Cell Necrosis, Arch. Surg./vol. 130, Dec. 1995, pp. 1260-1265.

Wang, Jiang Huai, et al. Induction of Human Endothelial Cell Apoptosis Requires Both Heat Shock and Oxidative Stress Responses, Am. J. Physiol. 272, 1997, pp. C1543-C1551.

Westra, Arthur, et al. Variation in Sensitivity to Heat Shock During the Cell-Cycle of Chinese Hamster Cells In Vitro, Int. J. Radiat. Biol., 1971, vol. 19, No. 5, pp. 467-477.

Wike-Holley, J.L. et al. The Relevance of Tumour pH to the Treatment of Malignant Disease, Radiotherapy and Oncology, 2 (1984) 343-366.

Zhang, S. et al. App. Spectroscopy 52:400-406 (1998).

* cited by examiner

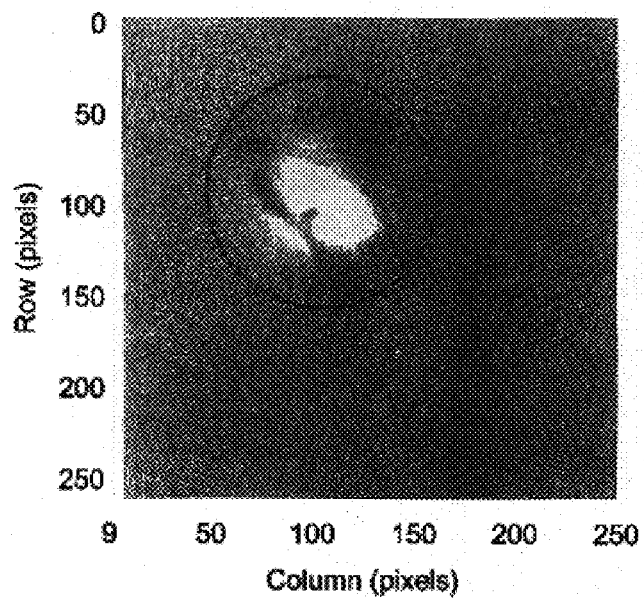
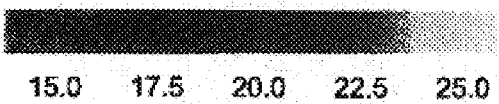
FIG. 3
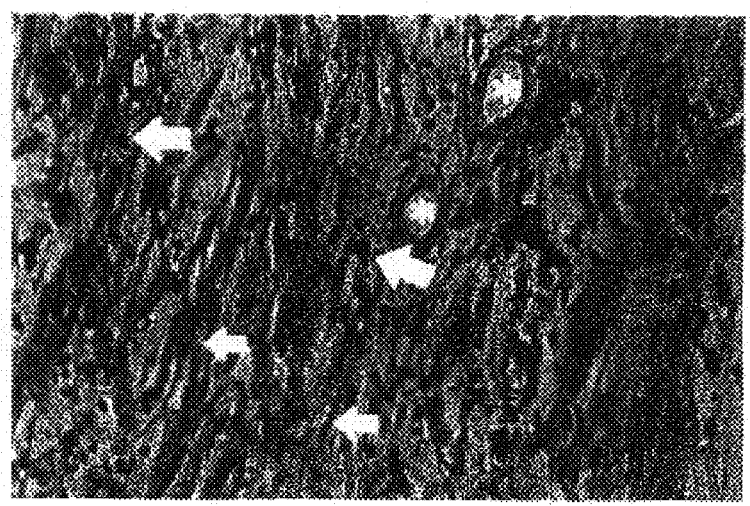
FIG. 7

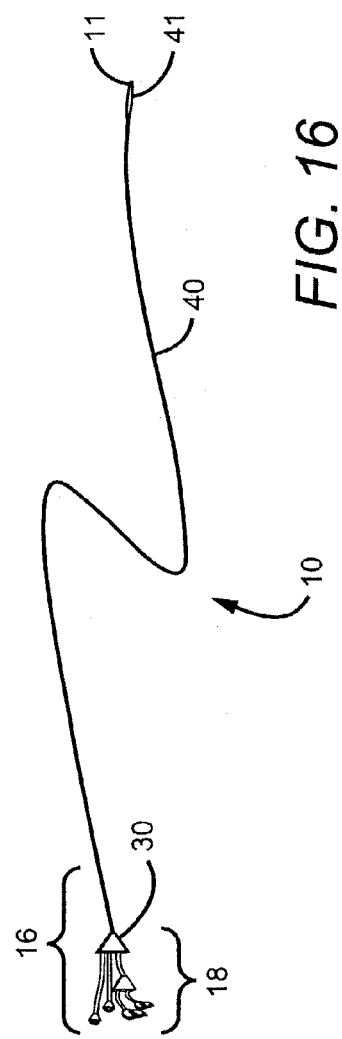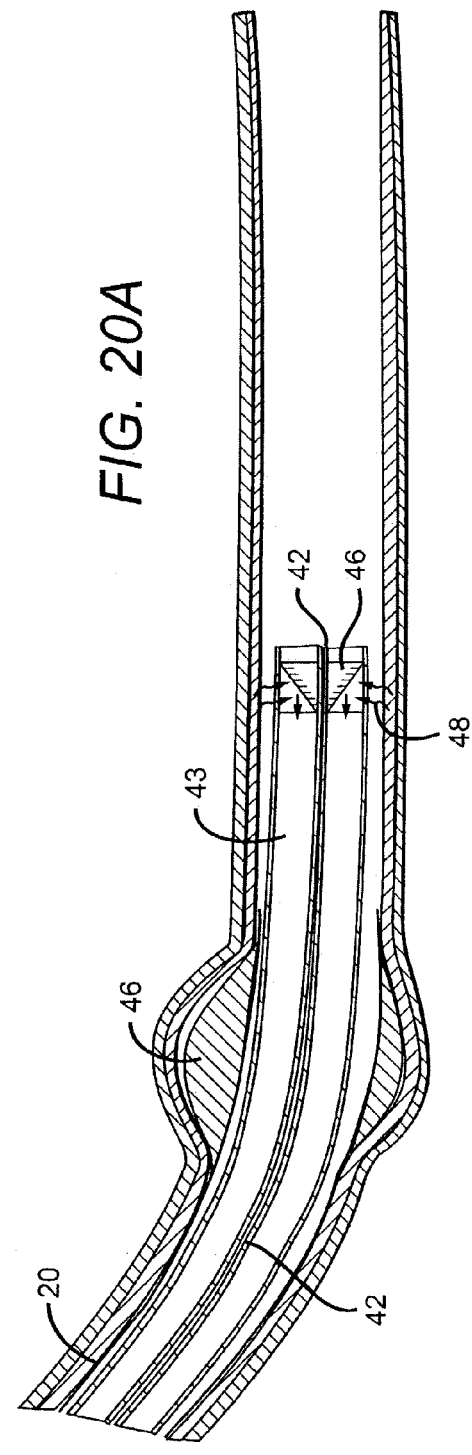

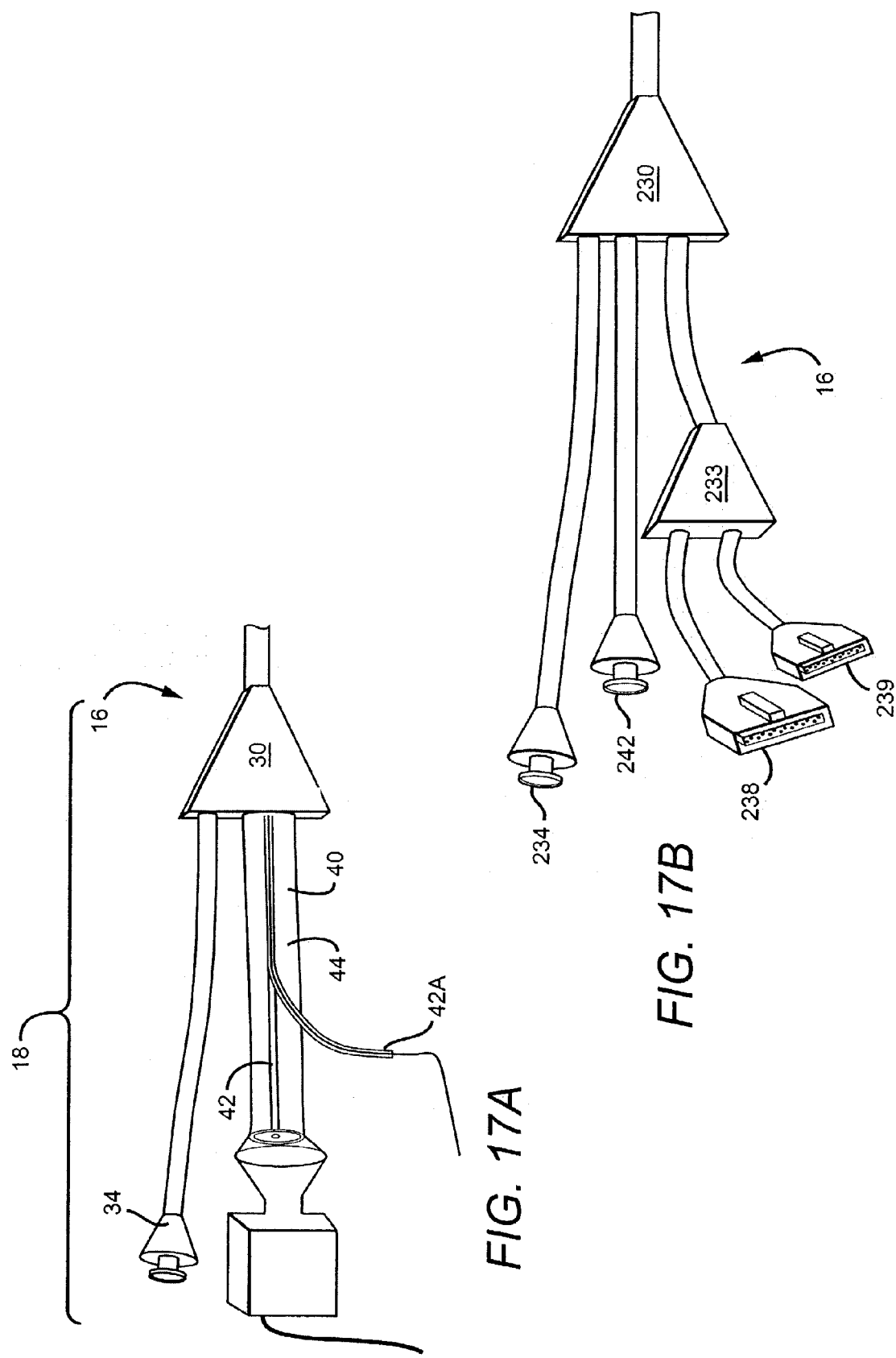

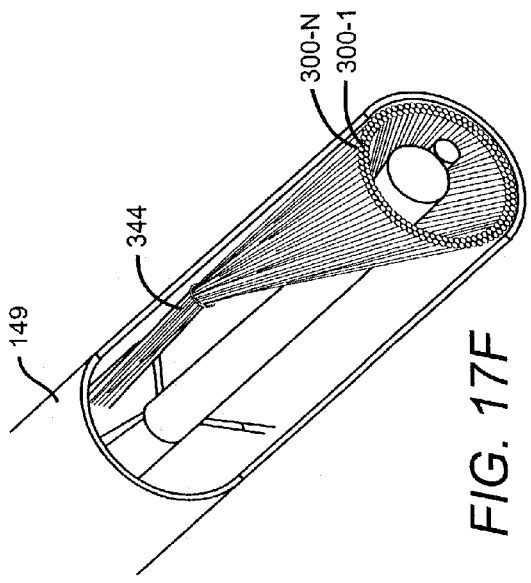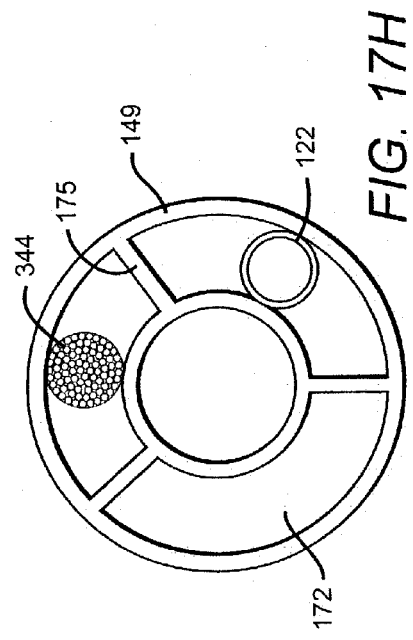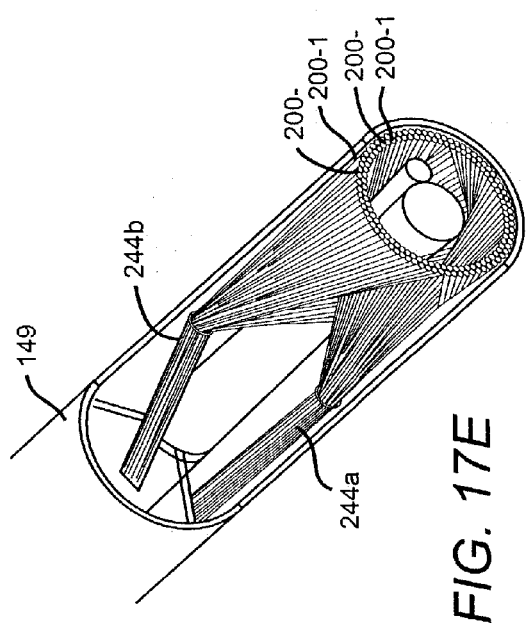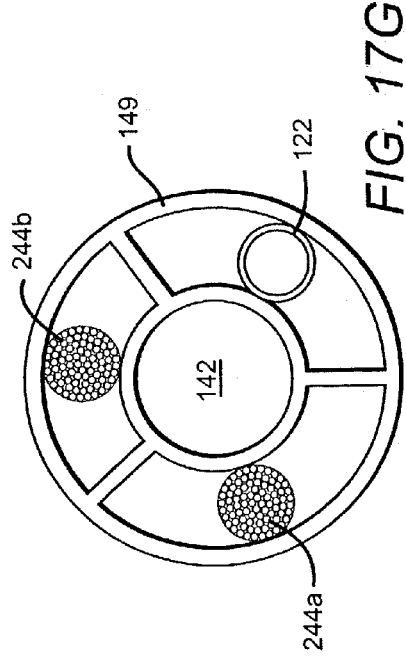

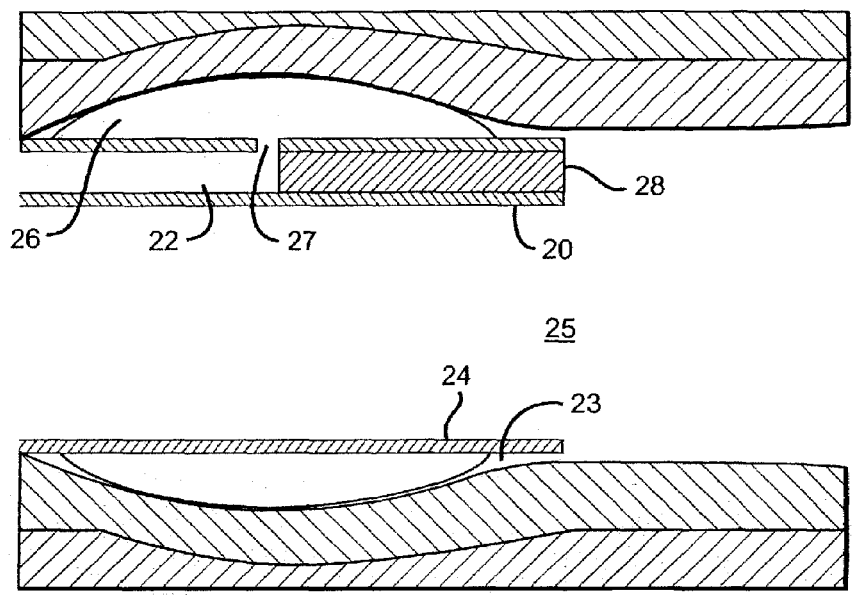
FIG. 18
FIG. 19A
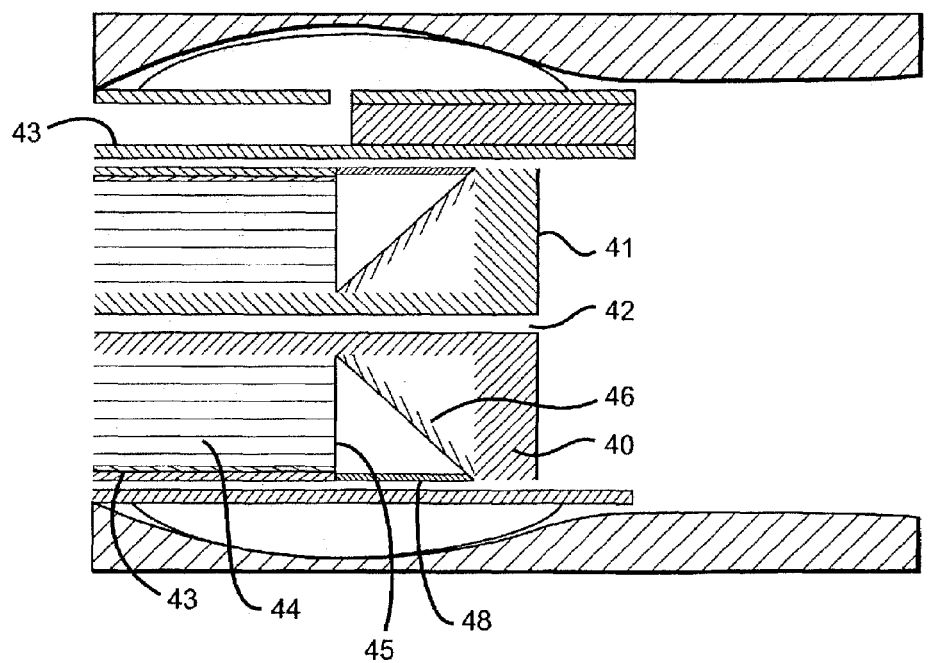

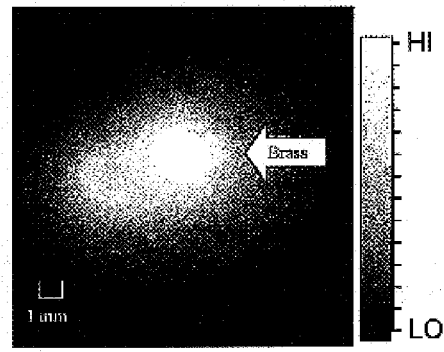
FIG. 22A
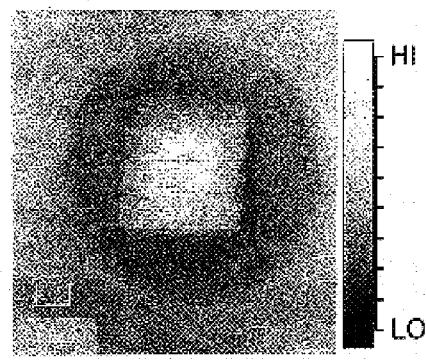
FIG. 22B
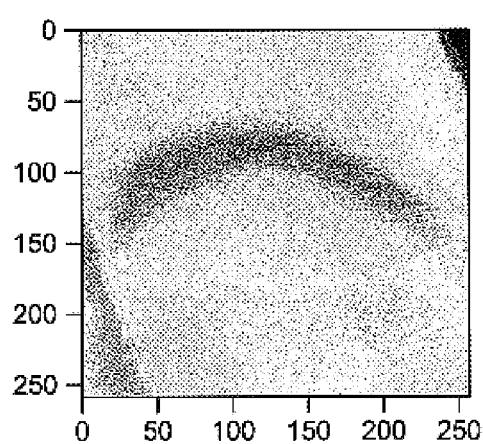
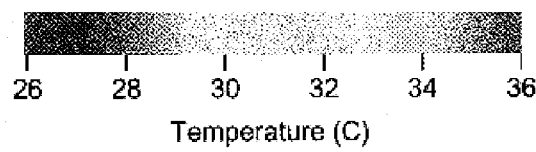
Temperature (C)
FIG. 34A

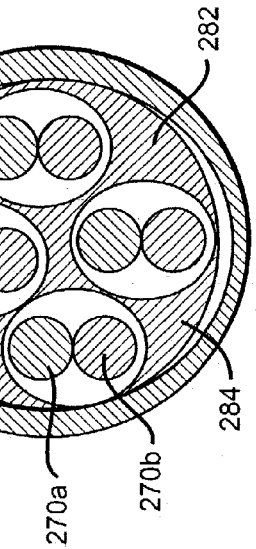
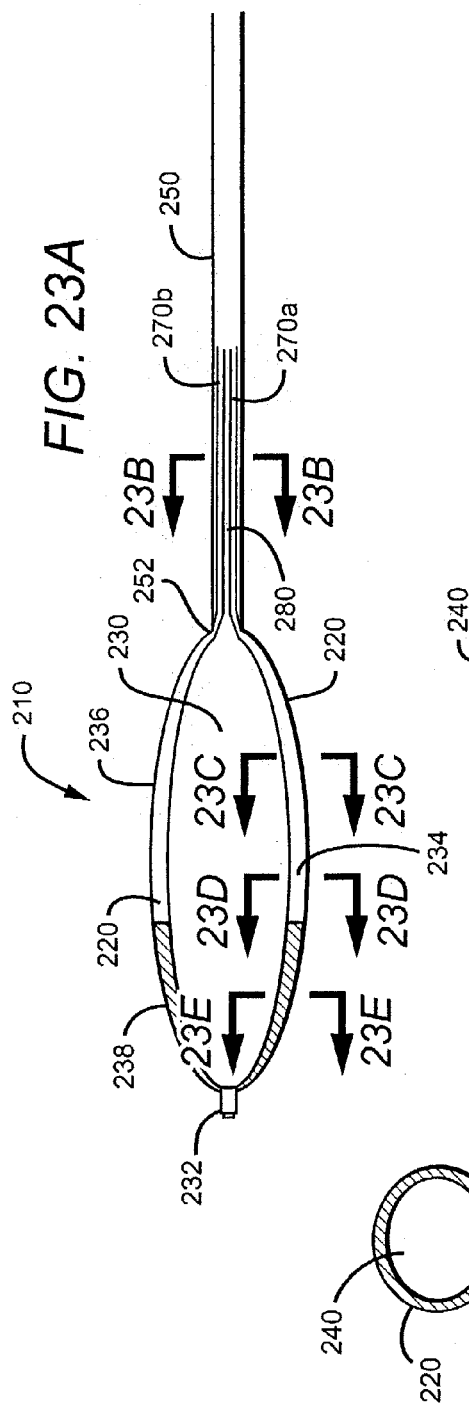
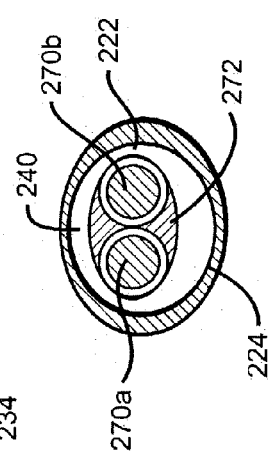
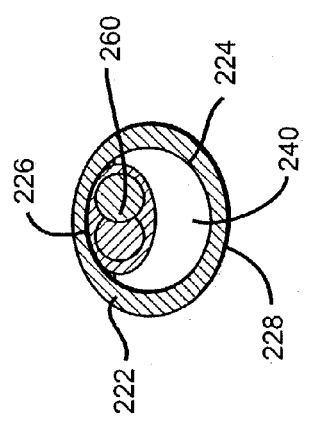

METHOD AND APPARATUS FOR DETECTING VULNERABLE ATHEROSCLEROTIC PLAQUE

CROSS-REFERENCE TO RELATED APPLICATION

The present application is a continuation application of Ser. No. 09/340,089, filed Jun. 25,1999, now U.S. Pat. No. 6,615,071 which is incorporated by reference herein.

STATEMENT REGARDING FEDERALLY SPONSORED RESEARCH OR DEVELOPMENT

Not applicable

BACKGROUND OF THE INVENTION

1. Field of the Invention

The present invention relates generally to methods of identifying in a living vessel an atherosclerotic plaque at risk of rupture or thrombosis. More particularly, the invention relates to such methods that include detecting sites of inflammation in a vessel wall exhibiting about 0.2°-5° C. temperature elevation above adjacent or ambient vessel wall temperature. The invention also relates to intravascular and non-invasive devices for measuring vessel wall temperatures and detecting about 0.2-5° C. temperature differences between regions of living vessel wall.

2. Description of the Related Art

Despite the declining age-specific mortality of coronary atherosclerosis, many people who feel well and have no known cardiovascular disease continue to die suddenly of a first myocardial infarction or cardiac arrest. An estimated 35% of these patients had neither symptoms nor a diagnosis of coronary artery disease (Casscells et al. *Lancet* 347:1147-1149 (1996); Falk et al. *Circulation* 92:657-671 (1995); Davies et al. *Lancet* 347:1422-1423 (1996); Falk et al. *Am J Cardiol* 63:114E-120E (1989)). Rupture and/or thrombosis of an atherosclerotic plaque is the immediate cause of most myocardial infarctions and strokes. Myocardial infarction is not predictable by presently available clinical means, which greatly hampers prognosis and treatment of patients suffering from cardiovascular disease (Fuster et al. *Circulation* 82:1147-1159 (1990); Davies et al. *Brit Heart J* 53:363-373 (1985); Libby, P. *Circulation* 91:2844-2850 (1995); Liuzzao et al. *N Engl J Med* 331:417-424 (1994); Itoh et al. *Coronary Artery Disease* 6:645-650 (1995); and Ridker et al. *N Engl J Med* 336:973-979 (1997)).

In most instances of myocardial infarction, cardiac arrest, or stroke, it is found that only one of the potential obstructions, or plaques, has in fact, ruptured, fissured, or ulcerated. The rupture, fissure, or ulcer causes a large thrombus or blood clot to form on the inside of the artery, which may completely occlude the flow of blood through the artery, thereby injuring the heart or brain. It is known that approximately one-half of the unstable coronary atherosclerotic plaques are in arteries with 50% or less luminal diameter narrowing. See, for example, Fuster, V., et al., *N Engl J Med* 326:242-250 and 310-318 (1992). These are lesions that are usually considered insignificant anatomically. Thus, it would be highly desirable if methods and devices were available to detect the unstable atherosclerotic plaque, independent of the degree of luminal diameter narrowing, and treat it before unstable angina and/or acute myocardial infarction and their consequences occur.

These culprit lesions, referred to as "vulnerable," "dangerous," "unstable" or "at-risk" plaques, have some unique histopathologic features. These features include: a lipid core containing a substantial amount of free and esterified cholesterol, and other necrotic debris; infiltrated macrophages (and less frequently lymphocytes, monocytes and mast cells); less abundant smooth muscle cells; and, consequentially, low content of collagen and other matrix proteins.

The lipid core characterizing most ruptured plaque is mainly a large pool of cholesterol resulting from insudation and from the release of the contents of foam cells following degradation of the cell wall. The low content of collagen and matrix proteins associated with at-risk plaque contributes to an important feature of the unstable plaque—the thin plaque cap. The release of matrix-digesting enzymes by the inflammatory cells is thought to contribute to plaque rupture. Small blood clots, particularly microthrombi, are also frequently found on non-ruptured but inflamed ulcerated plaque surfaces.

The rupture process is not completely understood, but it is known that the plaques most likely to rupture are those that have both a thin collagen cap (fibrous scar) and a point of physical weakness in the underlying plaque. Such points are thought to be located (as determined by modeling studies and pathologic analysis) at junctures where pools of cholesterol meet a more cellular and fibrous part of the plaque. It has been observed that plaques with inflamed surfaces or a high density of activated macrophages and a thin overlying cap are at risk of tirombosis. Van der Wal, et al., *Circulation* 89:36-44 (1994); Shah, et al., *Circulation* 244 (1995); Davies, et al., *Br Heart J* 53:363-373 (1985); Farb, et al., *Circulation* 92:1701-1709 (1995); Van Damme, et al., *Cardiovasc Pathol* 3:9-17 (1994).

Identifying Vulnerable Plaque

The development of medically feasible techniques to identify those plaques that are most likely to rupture, thrombose or rapidly progress in severity of vascular stenosis is an area of intense investigative activity. Most of the techniques undergoing study at the present time focus on the histological features of dangerous plaque. Modalities such as intravascular ultrasound, which might identify plaque vulnerability on the basis of cap thinness has been proven to be incapable of identifying which plaques are at risk of rupturing (de Feytia et al. *Circulation* 92:1408-13 (1995). Perhaps this is because the average cap thickness at the time of rupture is estimated to be 50 μm (Burke et al. *N Engl J Med* 336:1276-82 (1997); Mann et al. *Circulation;* 94:928-31 (1996); and Falk et al. id. (1995)).

Moreno et al. (*Circulation* Suppl 17:I-1016 (1998) employ NIR spectroscopy to correlate the NIR spectra of plaque with the histological features of thin fibrous cap, lipid pool, macrophages and calcium content in an atherosclerotic rabbit model.

In U.S. Pat. No. 5,935,075 (issued to Casscells, et al.) (U.S. patent application Ser. No. 08/717,449) some of the present inventors demonstrated for the first time that there is thermal heterogeneity in human atherosclerotic arteries and that inflamed plaques give off more heat than non-inflamed plaques. These inflamed regions, sometimes called "hot" plaques, are regions of atherosclerotic plaque that exhibit temperatures that are elevated about 0.4-4.0° C. above non-inflamed adjacent vessel wall temperature. Previously, local heat had not been identified in atherosclerosis and exploited for diagnosing vulnerable plaque based on the association of inflammation and macrophages with plaque rupture.

Recently, Stefanadis et al. (*Circulation* 99:1965-1971 (1999)) has reported a confirmatory study in patients suffering acute myocardial infarction showing substantial thermal heterogeneity (1.7° C.) at points along their coronary arteries, as measured by a catheter-mounted thermistor in contact with the vessel wall.

U.S. Pat. No. 5,935,075 (Ser. No. 08/717,449) (Casscells et al.) also discloses a method of detecting heat-producing inflammatory cells at sites along a vessel wall using an infrared-sensing catheter, or other invasive or non-invasive temperature measuring devices. One exemplary catheter includes an infrared-transparent balloon enclosing a group of optical fibers.

U.S. Pat. No. 5,871,449 (issued to Brown) describes another infrared fiber optic catheter intended for measuring vessel wall temperature to reveal inflamed plaques. One problem with currently-available infrared optical fibers is that they are not made of biocompatible material, and are therefore unsuitable for directly contacting tissues and fluids inside a human blood vessel. Also, the somewhat brittle nature of conventional infrared optical fibers makes them incapable of bending sufficiently to be aimed directly into a plaque (i.e., perpendicular to the linear axis of the vessel). Infrared fiber optic catheter designs must also take into account the interference by blood, saline or other vessel fluids with the infrared signal.

Catheter-Based Temperature Sensing Devices

A number of devices and procedures have been employed to diagnose, treat or inhibit vascular obstructions, and in some of these devices a temperature sensing element is included. Most of these temperature sensing means are intended to monitor high-temperature heating of vascular lesions. Very few of these intravascular heat sensing devices are actually capable of, or practical for, discerning slight to moderate temperature elevations (i.e., 0.01° C. or more) along the luminal wall of a vessel.

U.S. Pat. No. 5,057,105 relates to a hot tip catheter assembly for "melting" plaque. This device employs a thermocouple to continuously monitor the heating of the catheter tip in order to prevent overheating of the vessel wall.

The recent U.S. Pat. No. 5,775,338 (issued to Hastings) describes a heated perfusion balloon for reduction of restenosis by application of low-level heat to a site of arterial injury. For measuring the extent of heating of the vessel wall, a J-type thermocouple mounted on the outside of a balloon is pressed against the vessel wall to measure temperature relative to bloodstream temperature. The blood temperature is measured by another temperature sensor which is disposed upstream of the thermocouple sensor.

Most of the prior art methods and catheter-based heat sensing devices are unable to differentiate plaque from normal vessel wall, much less distinguish between unstable plaques and the more stable ones that are not at imminent risk of rupturing or occluding. Even when the presence or absence of histological features such as calcification in plaque can be assessed by one of the existing devices, it is not adequately predictive of whether the plaque is unstable or whether it will tend to rapidly progress in severity of vascular stenosis. It is very important to be able to detect the unstable atherosclerotic plaque independent of the degree of luminal diameter narrowing, and treat it before the unstable angina and/or acute myocardial infarction and their consequences occur.

Medical Infrared Thermography

Infrared thermography or radiometry (IR), has long been used for non-destructive testing in a wide range of industrial disciplines, such as determining the condition of selected electrical components, motors, metal fatigue, for example. Similar technology has also been widely employed for many years to make practical temperature measurements in military and medical fields by applying principles of infrared radiation and thermal imagery.

In the human body, heat is produced by metabolism. It is distributed by blood and the lymphatic system to the rest of the body, and particularly to the overlying skin. Heat is lost primarily by radiation and convection of the excessive heat energy through the skin and into the surrounding air. The IR radiation from the human body can be detected by the IR thermography. Correlating the temperature to the metabolic state of the body, one can obtain useful information about the diseased states of the body organs.

For example, U.S. Pat. No. 5,445,157 (Adachi et al.) describes a type of infrared thermographic endoscope for imaging a body cavity after injecting a low-temperature gas. U.S. Pat. No. 4,995,398 relates to the use of thermography during the course of by-pass heart surgery for the purpose of checking the success of the operation before closing the chest cavity. This patent describes the use of a scanning thermal camera, image processing, temperature differentials and displaying images in real time. Stenoses at the sites of distal anastomoses are detected using a cold injectate, which when mixed with the warmer circulating blood, provides images which are captured by a thermal camera focused on the heart.

Several decades ago, IR thermography was investigated for detecting breast cancer. In these early studies, thermographic liquid crystals and infrared-sensitive film were used to record asymmetries in the venous drainage from the breasts. The steins in most people are close enough to the surface to be identifiable by thermal mapping techniques. Markedly asymmetric patterns often indicated the presence of breast lesions, in some cases before a symptom or palpable mass was evident. Infrared thermography did not have the sensitivity of x-ray mammography for deep masses, however, because the temperature of many such masses does not directly reach the skin. Also, many such masses do not create an obvious disturbance in the pattern of venous drainage.

Recent developments in thermal imaging detectors, semiconductors, and high speed computers and imaging software have enhanced the accuracy and sensitivity of infrared thermography, thus making it more attractive as a non-invasive tool for medical and diagnosis. Medical IR thermography today is a noninvasive diagnostic technique that allows the examiner to visualize and quantify changes in skin surface temperature, which maps the body temperature several mm deep to the skin, and is referred to as a thermogram (Cotton *J Am Med Assoc* 267:1885-1887 (1992)). Since there is a high degree of thermal symmetry in the normal body, subtle (0.02° C.) temperature asymmetries can be identified quickly and an explanation can be sought. IR thermography has also been used recently in determining the level of amputation in patients with gangrene (McCollum et al. *Br J Surg* 75:1193-5[see comments] 1988; Spence et al. *Prosthet Orthot Int* 8:67-75 (1984); Spence et al. *Angiology* 32:155-69 (1981); Bergtholdt et al. *Arch Phys Med Rehabil* 56:205-9 (1975)). These surgeons found that a degree of coolness accurately demarcated nonviable tissue. Thermography has also been recently used by others to assess the completeness of revascularization during aortocoronary bypass surgery. In this procedure, an infrared camera is placed several feet over the open chest, and when the aorta is unclamped and normal blood flow is returned to the myocardium, the areas that have been revascularized promptly radiate warmth; whereas the ischemic areas remain cool. The grafts to these areas can then be adjusted to improve the flow (Saxena et al. *Pediatr Surg Int* 15:75-76 (1999); Merin et al. *Cardioivasc Surg* 3:599-601 (1995); Falk et al. *J Card Surg* 10:147-60 (1995); Lawson et al. *Am J Cardiol* 72:894-6 (1993). Despite this work, infrared is little used clinically today, and workable IR catheters have not been developed, due at least in part to the large size, brittleness and expense of commercially available IR optical fibers.

There are a number of commercially available catheters that monitor blood temperature in order to measure cardiac output (e.g. American Edwards/Baxter Swan Ganz catheter) by continuous thermo-dilution, but these catheters cannot measure the temperature of the vessel wall itself, or of specific plaque regions on the vessel wall.

Of the existing catheter-based and non-invasive methods and devices, none have proved to be adequate or practical for clinical use to identify unstable atherosclerotic plaques. What is needed are better ways to distinguish the dangerous plaques from the relatively more stable ones, regardless of their degree of luminal narrowing. Also needed are ways to detect specific arterial sites that are at risk for arterial restenosis after angioplasty or atherectomy.

SUMMARY OF THE INVENTION

The present invention overcomes many of the failures of the prior art by providing a sensitive method of identifying vulnerable or at-risk atherosclerotic plaque in a vessel. Moreover, the methods of the invention are able to distinguish such vulnerable plaques from the relatively stable plaques by detecting regions of elevated temperature along the vessel wall as an indicator of populations or clusters of activated inflammatory cells. An important advantage of the present methods is that they assist the physician in diagnosing plaques at imminent risk of rupturing or occluding so that appropriate interventional steps may be taken to avert a possibly fatal cardiovascular event. Certain embodiments of the invention also permit the physician to monitor the condition of grafts and transplants so that the influx of inflammatory cells and the development of transplant vasculopathy can be detected and treated before the occurrence of a critical event.

In addition, new devices are disclosed which are useful for carrying out the minimally or non-invasive methods of the invention. Preferred exemplary devices include an infrared-sensing fiber optic bundle catheter and a thermocouple basket catheter, each of which is capable of detecting slight to moderate temperature differences between identifiable regions of a vessel. Such temperature differences are primarily in the range of about 0.2-5.0° C., particularly the 0.4-4.0° C. range, with plaques often exhibiting temperature differences of about 1.5° C. or more.

The methods and devices of the present invention are also useful in predicting the behavior of injured blood vessels in medical patients, such as identifying specific arterial sites at risk for arterial restenosis after angioplasty or atherectomy, or identifying which patients are at risk due to vasculopathy or tissue rejection.

The devices and methods of the present invention also are capable of effectively identifying patients who have arterial wall areas of unusually low temperature and which represent previously undetected arterial at-risk areas. Just as excess heat can identify regions at risk due to inflammation, subnormal heat (i.e., areas cooler than the rest of a vessel) indicates a lack of actively metabolizing healthy cells, since heat in the body results from actively metabolizing cells. Non-cellular areas are typically regions of hemorrhage, thrombosis, cholesterol pools, or calcium—all indicators of high risk plaques. The devices and methods of the invention achieve these ends by identifying and analyzing thermal discrepancies in the wall temperature of blood vessels. In some embodiments of the invention, devices are provided that are also capable of providing a thermal image of the vessel wall and of applying therapeutic gentle heat treatment.

In accordance with the present invention, a method is provided for detecting along a vessel wall an atherosclerotic plaque that is at risk of reducing the flow of fluid within the vessel. The method includes determining whether a plaque exhibits an elevated temperature compared to a predetermined baseline temperature, such as an average vessel wall temperature.

Also in accordance with the invention is a method of identifying in a living vessel an atherosclerotic plaque at risk of rupture or thrombosis. The method comprises measuring the temperature of at least two sites along the lumen wall of a vessel in a living subject and detecting a temperature elevation of about 0.2 to 5° C. at one site relative to the temperature of at least one other site along the vessel In certain embodiments of the methods of the invention an average or ambient vessel wall temperature is established and a 0.4 to 4° C. temperature difference is assessed between one site and the average or ambient vessel wall temperature. In some embodiments the temperature difference detected is about 0.2-2.5° C., and preferably a temperature difference of at least about 1.5° C. is detected in at-risk plaque.

In preferred embodiments of the methods a heat detecting catheter assembly is introduced into a vessel of a living subject to identify at-risk plaque. In some embodiments the heat detecting catheter of the assembly is an infrared imaging catheter that has a flexible housing enclosing a flexible imaging bundle. The infrared imaging bundle contains a plurality of coherent optical fibers that are, a circumferential window in the housing that is designed for contacting a vessel wall. Also enclosed by the catheter housing is a reflective surface is in "optical communication" with both the window and the optical fibers. This means that optical radiation emitted from the vessel wall is received by the reflective surface and directed into the fibers. Likewise, optical radiation emitted from the fibers is received and reflected by the reflective surface and directed onto the vessel wall. Also enclosed by the catheter housing is a lumen that can accommodate either a guidewire or a flushing fluid for washing the occluded vessel ahead of the catheter. The catheter assembly employed in the methods may also include a guiding catheter that has an inflatable occluding balloon, an inflation lumen and a special lumen for receiving or guiding the infrared catheter.

In certain alternative embodiments of the methods a heat detecting catheter that employs a thermocouple basket catheter is introduced into the vessel. In some of these the thermocouple basket have a point of maximum outer diameter when deployed, at least one channel containing a pair of electrically insulated thermocouple wires, and a thermocouple junction situated at said maximum diameter point and disposed inside said channel between a thermally conductive layer and a thermally insulating layer. Some embodiments include an intravascular ultrasound wire (IVUS) for obtaining an ultrasound image in conjunction with obtaining a thermal map of a vessel wall.

Certain other embodiments of the methods introduce a thermistor basket catheter into the vessel. In some of these thermistor basket catheter embodiments the basket has a point of maximum outer diameter when deployed and at least one channel containing a resistive temperature device situated at said maximum diameter point.

Still other alternative embodiments of the methods involve introducing a catheter chosen from the group consisting of intravascular ultrasound, intravascular magnetic resonance imaging, liquid crystal coated balloon catheter thermometry and catheter-based near-infrared spectroscopy.

Also in accordance with the present invention are non-invasive methods for detecting at-risk plaque. Some of these include measuring the temperature of at least two sites along the vessel wall using infrared, microwave, or magnetic resonance imaging.

The present invention further provides an infrared imaging catheter that comprises a flexible housing enclosing a flexible imaging bundle. The imaging bundle contains a plurality of coherent optical fibers, preferably about 900. The imaging bundle is arranged around a guidewire/flushing lumen that extends lengthwise through the catheter. There is a window in the housing that extends around the circumference of the catheter and is made for contacting the vessel wall. A reflective surface, such as a mirror, is in optical communication with the window and the optical fibers.

An intravascular infrared imaging catheter assembly for detecting temperature heterogeneity along a vessel wall is also provided by the present invention. One embodiment of this assembly includes the above-described IR catheter and also has a guiding catheter for receiving the IR catheter in such a way that the IR catheter can slide within the lumen of the guiding catheter. The guiding catheter also has an inflatable occluding balloon and an inflation lumen connected to the balloon. In some embodiments an ultrasound wire or transducer is located in the guidewire/flushing lumen, so that ultrasound examination of the vessel wall can be conducted in conjunction with the temperature sensing. In some embodiments means are included in the catheter assembly for applying 38° to 45° C. heat to discrete regions of vessel wall.

An infrared imaging catheter in accordance with the invention may also include an infrared array detector, a signal processor, a microcontroller programmed for receiving, storing, analyzing and reporting temperature information obtained from a plurality of sites along a vessel wall, a display system, such as a computer monitor, and a user interface such as a keyboard. The catheter is in optical contact with the infrared array detector. The detector is in electronic contact with the signal processor, and the signal processor is in electronic contact with the display system and the microcontroller. The microcontroller, which may be a personal computer, is also in electronic contact with the user interface.

In some embodiments, particularly those incorporating a heating modality, the assembly also has an infrared radiation source in optical communication with an infrared fiber multiplexer. In this case, the multiplexer is also in electrical contact with the microcontroller.

A thermocouple basket catheter according to the invention also provides for detecting temperature heterogeneity along a vessel wall. Certain embodiments of this catheter comprise an expandable basket formed by at least two hollow channels that have proximal and distal end. Each of these channels contains a thermally conductive material, and each channel has a vessel wall-contacting side and a vessel lumen facing side. A hollow shaft is joined to the proximal end of the basket and a tip is joined to the basket's distal end. A thermocouple junction is situated inside each channel, with the junction being situated along the length of each channel at a point about mid-way between the basket's proximal and distal ends. Inside each channel, the junction is situated "off center" so that it is in thermal contact with the side of the channel that touches the vessel wall. The junction is away from, and thermally insulated from, the lumen facing side of the channel. The two insulated thermocouple wires inside each channel extend from the junction through the hollow shaft of the catheter. The basket also includes a tip that encloses the distal end of each channel. The channel ends may be either fixed securely inside the tip or they may be able to move back and forth inside the tip.

One embodiment of an intravascular thermocouple catheter assembly for detecting temperature heterogeneity along a vessel wall contains the above-described thermocouple basket catheter and a guiding catheter with a guiding lumen adapted for slidingly receiving the thermocouple basket catheter. In some embodiments the guiding catheter has an inflatable occluding balloon and an inflation lumen in communication with the balloon. Certain embodiments include a thermally insulating material disposed inside each of the channels between the junction and the lumen-facing side of the channel.

Another catheter embodiment of the invention is a thermistor basket catheter. An expandable basket is formed by at least four hollow channels, each channel having a vessel wall-contacting side and a lumen facing side. A hollows shaft is joined to the proximal end of the basket and a tip is connected to the basket's distal end. On each channel a thermistor is situated on the outside of each of the channels, and placed longitudinally on each channel at about the point of maximum deployment for each channel on the vessel contacting side of the channel. A pair of insulated wires in electrical contact with the thermistor extends from the thermistor through the hollow shaft.

Certain preferred embodiments of the catheters of the present invention have an outer diameter of no more than about 6 mm, and in some embodiments the diameter is no more than 3 mm.

One preferred assembly for identifying vulnerable atherosclerotic plaque includes an infrared catheter having an external diameter of no more than 6 mm. This catheter includes a flexible housing that encloses a flexible imaging bundle containing a plurality of coherent optical fibers. The bundle is disposed about a guidewire/flushing lumen that extends lengthwise through the catheter. There is a circumferential window in the housing that is designed for contacting the vessel wall. A reflective surface, such as a conical mirror is in optical communication with both the window and the optical fibers. The assembly also includes a guiding catheter with an inflatable occluding balloon, an inflation lumen connected to the balloon, and a guiding lumen designed for receiving the imaging catheter in such a way that the catheter slides through the guiding lumen. The assembly also includes an infrared array detector, a signal processor, a microcontroller programmed for receiving, storing, analyzing and reporting temperature information obtained from a plurality of sites along a vessel wall, a display system and a user interface. The optical fibers are in optical contact with the infrared array detector, and the detector is in electrical contact with the signal processor. The signal processor is in electrical contact with the display system and the microcontroller. The microcontroller is in electrical contact with the user interface. In an alternative embodiment the assembly also includes an infrared radiation source in optical communication with an infrared fiber multiplexer, and the multiplexer is also in electrical contact with the microcontroller.

Another assembly for identifying vulnerable atherosclerotic plaque, which is provided by the invention, employs one of the thermocouple or thermistor catheters of the invention, a suitably programmed microprocessor capable of receiving, storing, analyzing and reporting temperature information, a temperature display, system, and a user interface.

A method of detecting and monitoring inflammation in a transplanted arteriovenous (AV) graft in a living subject is also provided by the invention. This method comprises using an infrared camera and non-invasively imaging said arteriovenous graft to obtain an initial infrared thermogram of the AV graft. After obtaining an initial infrared thermogram, the infrared imaging is repeated to obtain a second infrared thermogram of the graft. After the second thermogram, the infrared imaging is optionally repeated to obtain at least one subsequent infrared image of the graft. The initial, second and subsequent infrared images are then compared to identify temperature changes in a region of the graft. From the observed temperature changes, an increase, decrease or no change in inflammation is determined for at least one region of the graft.

The invention further provides a method of evaluating an anti-atherosclerotic interventional therapy in a flowing mammalian artery. This method includes producing an animal model of human atherosclerosis by feeding cholesterol to a Watanabe heritable hypercholesterolemic rabbit such that visible, palpably warm atherosclerotic lesions extending along the central ear artery of the rabbit develop. The temperature of at least one region of the ear artery is then measured non-invasively to obtain at least one baseline temperature measurement. Preferably the non-invasive temperature measurement is done with an infrared imaging camera. An anti-atherosclerotic interventional treatment it then administered to at least one said animal model. A suitable control treatment is similarly administered to at least one said animal model. Subsequent to said treatments, the temperature of at least one region of rabbit artery in at least one said treated animal model is non-invasively measured to obtain at least one post-treatment temperature measurement. The method further includes comparing the baseline, control and post-treatment temperature measurements, and detecting any temperature differences in an artery attributable to the interventional treatment.

Also according to the present invention a method of monitoring the progression or amelioration of an atherosclerotic plaque in a flowing mammalian artery is provided. This method comprises breeding genetically hypercholesterolemic animals characterized by development of atherosclerotic lesions that are histologically similar to human atherosclerotic plaques, whereby an animal model of human atherosclerosis is produced. Employing a heat-detecting catheter of the invention, the temperature of a multiplicity of sites along a vessel wall of the animal is measured, in order to obtain a baseline temperature measurement for each of the sites. The physical location of each such site along the vessel wall corresponding to each respective temperature measurement is recorded. The catheter is then removed from the vessel of the animal. At a later time, the same or a similar catheter is reinserted and the temperature measurement and recording of physical location are repeated. Any temperature difference between adjacent sites of the vessel wall and/or any temperature difference between each site and its corresponding baseline temperature are then determined.

The invention's methods and devices will have a number of utilities, including reduction of morbidity and mortality from coronary and carotid artery atherosclerosis, reduction of restenosis and thus the need for repeated angioplasties or atherectomies, and also including reduction of vasculopathy in organ-transplant patients. In turn, these improved outcomes will produce the benefits of better health care, improved public health, and reduced health care costs. These and other objects, features and advantages of the present invention will become apparent with reference to the following description and drawing.

BRIEF DESCRIPTION OF THE DRAWINGS

The patent or application file contains at least one color photograph. Copies of this patent or patent application publication with color photographs will be provided by the Office upon request and payment of the necessary fee.

For a detailed description of a preferred embodiment of the invention, reference will now be made to the accompanying drawings wherein:

FIG. 3 is an ex vivo infrared photograph of a freshly harvested living carotid endarterectomy specimen, taken in a 23° C. room.

FIG. 7 is a color photomicrograph of atherosclerotic plaque showing predominantly macrophages, as indicated by immunoreactivity with HAM-56 antibody (dark brown stain/large arrow). Lightly stained (non-apoptotic) cells having the appearance of smooth muscle cells are marked by small arrows. Asterisks denote venules.

FIG. 16 is a perspective view of one embodiment of the catheter assembly represented in FIG. 15.

FIG. 17A is an enlarged view of one embodiment of the proximal end of the catheter shown in FIG. 16.

FIG. 17B is an enlarged view of another embodiment of the connector assembly and proximal end of FIG. 16.

FIG. 17E is a partial cutaway view of the catheter of FIG. 17B.

FIG. 17F is a partial cutaway view of an alternative embodiment of the catheter of FIG. 17B.

FIG. 17G is a cross-sectional taken across the axis of the catheter shown in FIG. 17E.

FIG. 17H is a cross-sectional taken across the axis of the catheter shown in FIG. 17F.

FIG. 18 is a longitudinal cross-sectional view of the distal end of on embodiment of the introducer catheter of the present invention, showing its operative placement in a blood vessel for used in conjunction with the infrared catheter of FIG. 16 to measure the temperature of a region of vessel wall.

FIG. 19A is similar to FIG. 18 and shows one embodiment of the infrared catheter of FIG. 16 as it is introduced into a blood vessel.

FIG. 20A is a longitudinal cross-section illustrating the use of the infrared catheter and introducer of FIGS. 19A-C for detecting infrared radiation emitted from a plurality of circumferentially arrayed sites on an interior vessel wall.

FIGS. 20D-1 through 20D-4 illustrate various embodiments of the reflector mounted at the tip of the catheter shown in FIG. 20B. Shown are (D-1) a conical surface reflector where the mirror surface and the fiber axis form an angle between 0 and 90, preferably 45°; (D-2) a convex surface at each cross section form a cone which will reflect a wider area of lumen wall onto fiber bundle; (D-3) step wise mini reflectors also reflect a wide area of lumen wall onto fiber bundle; and (D-4) a concave reflector which will focus a narrower area of the lumen wall.

FIG. 22A is a black and white infrared image of a temperature phantom taken with the infrared fiber optic bundle of a catheter of the invention.

FIG. 22B is a close up infrared image of the brass rod taken with a 900 fiber array.

FIG. 23A is a side view of one embodiment of the thermocouple shape memory basket catheter assembly of the invention showing the basket in the expanded configuration outside the guiding catheter.

FIG. 23B is a radial view of a cross-section of the catheter shown in FIG. 23A taken across the hollow shaft of the catheter.

FIG. 23C is a radial view of a cross-section of a channel taken on the proximal side of the thermocouple junction.

FIG. 23D is a radial view of a cross-section of a channel taken at the thermocouple junction.

FIG. 23E is a radial view of a cross-section of a channel taken on the distal side of the thermocouple junction.

FIG. 34A is an infrared photograph of the prosthetic arteriovenous hemodialysis graft of a patient with renal failure.

DETAILED DESCRIPTION OF PREFERRED EMBODIMENTS

Figure 1:
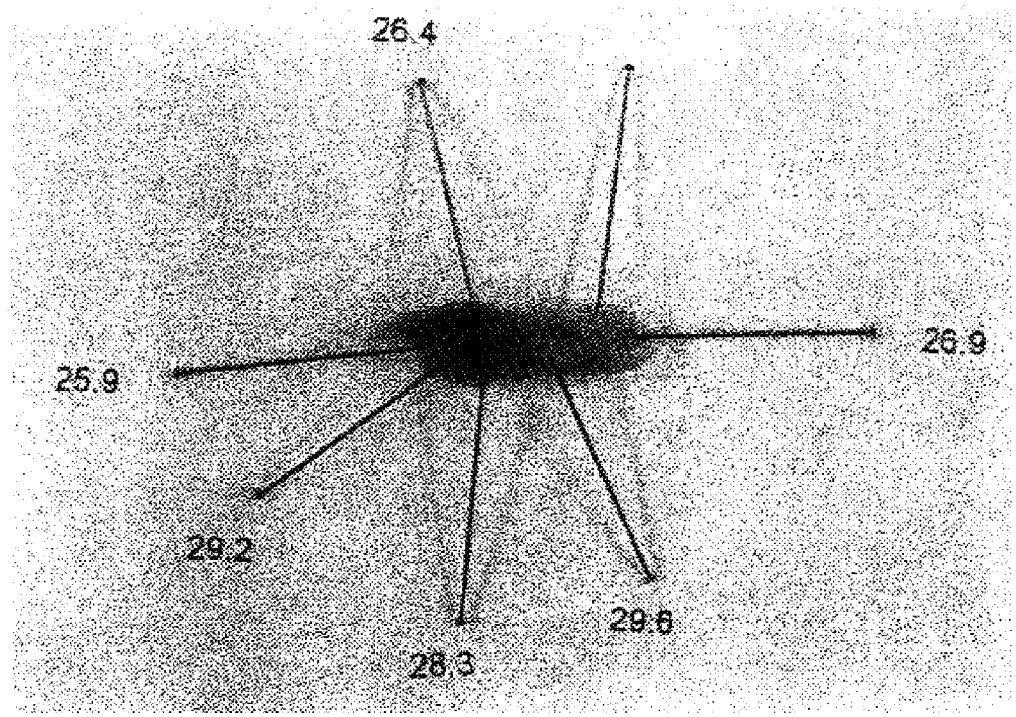
FIG. 1 is a color photomicrograph of the luminal wall of a fresh carotid endarterectomy specimen, with pins denoting regional temperatures, measured by thermistor, in a 25° C. room.

In the description which follows, the inventors confirm and extend their earlier observations that approximately one-third of human atherosclerotic plaque specimens have temperature heterogeneity ranging from about 0.2° to 4.0° C. as measured in live, freshly excised carotid endaiterectomy specimens. FIG. 1 is a photomicrograph of one such specimen, with pins marking the temperatures of various regions of the plaque. The term "temperature heterogeneity" means that the surface temperature of a plaque is not uniform along its length and width. The term also refers to the temperature differences between certain plaque regions and other vessel sites or an average or ambient vessel wall temperature. The fact that human atherosclerotic plaque with measurable temperature heterogeneity has the morphological characteristics of plaque that is likely to ulcerate provides a new and sensitive way to detect and treat these dangerous plaques before myocardial infarction and its consequences occur. This temperature heterogeneity can be detected in vivo in accordance with the methods of the invention using any suitable intravascular or externally applied thermographic device that is capable of discriminating slight to moderate temperature differences (i.e., about 0.2-4.0° C.) between regions of a luminal wall, or between a particular region and the average or ambient vessel wall temperature. Exemplary new devices have been developed for use in the heat detection methods, and these are also described in detail below.

Correlation of "Hot" Plaque with Vulnerable Plaque in Ex Vivo Studies

Extending the observations described in U.S. Pat. No. 5,935,075 (application Ser. No. 08/717,449), 61 atherosclerotic plaques were removed from 61 patients at the time of carotid endarterectomy performed for neurological symptoms or after ultrasound screening. These specimens were collected in the operating room and immediately inspected by an experienced pathologist. Immediately thereafter the specimens were examined with a 24-gauge needle thermistor (Cole-Parmer Model No. 8402-20, resolution 0.1° C.; time constant 0.15 sec) in a 37° chamber. Temperature measurements were taken at approximately 2-mm intervals, yielding approximately 30 temperature measurements per plaque. This enabled a background temperature to be established with, in general, 6-7 zones per plaque, and reflecting temperature variations of more than 0.2° C. In each case, the background temperature and two other zones (most of which were warmer than background) were marked with colorfast dye of different colors for subsequent localization on tissue sections. The tissues were then fixed in 10% formalin and cut and embedded to reveal the intima and media and processed for routine histology followed by staining with haematoxylon and eosin or Masson's trichrome or immunostaining for macrophages with the HAM-56 and KP1 (CD68) antibodies from Dako. Under a Nikon microscope (SMZ-U Nikon Optiphot-2), the cell density was measured in a 200×400-micron (depth×width) region beneath the marked regions, using the program NIH Image, Version 1.43. The results are shown in FIG. 2, demonstrating that lumen temperature increases with increased cell density in living human atherectomy specimens.

Figure 2:
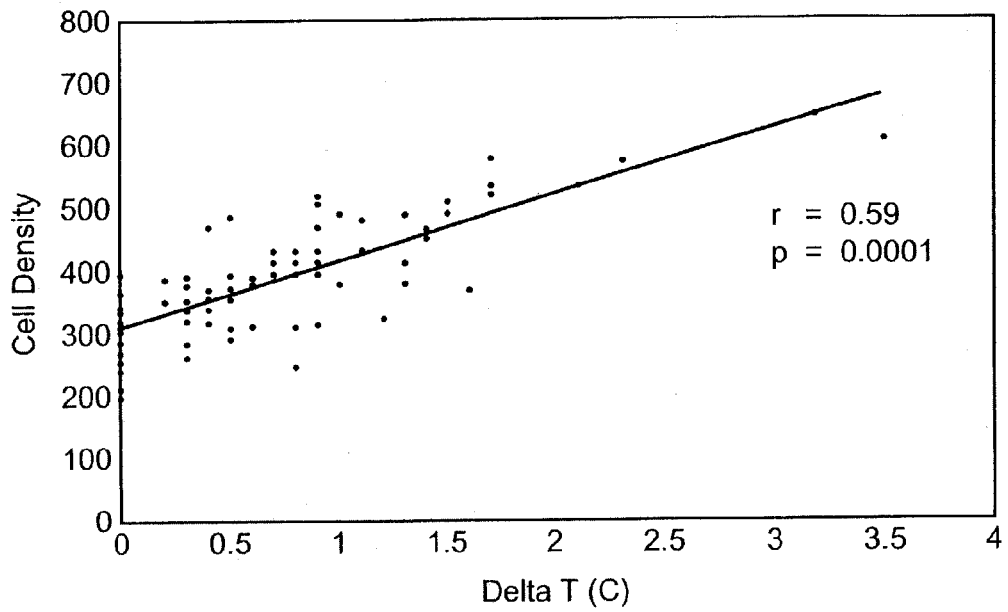
FIG. 2 is a graph showing the relationship of vessel wall surface temperature to underlying cell density, as measured by thermistor in freshly excised human carotid endarterectomy specimens.

FIG. 2 is a graph showing that regional lumen temperature increases as the underlying cell density of the region increases in living human carotid atherectomny specimens. For each specimen three points were plotted (the median, coolest and warmest zones) in relative degrees centigrade. The representative plaque shown in FIG. 1 demonstrates considerable thermal heterogeneity. The temperature of various regions of the lumen of this freshly harvested carotid endarterectomy specimen was measured by thermistor in a room at 25° C. In the photomicrograph the pins denote the temperatures of various plaque regions. The results of these studies clearly demonstrate that the temperature of the lumen surface in living human carotid endarterectomy specimens varied by as much as 3.5° C. within the same specimen, indicating that there is thermal heterogeneity in living human atherosclerotic plaques. In these studies, the themistor's characteristics and the reproducibility of the temperatures at these locations were excellent, always being 0.2° C. or less. All of the specimens demonstrated differences of 0.3° C. or more between their warmest and coolest measured locations.

A representative number of the human endarterectomy specimens were photographed immediately after removal from the 37° C. incubator using a Santa Barbara Focalplane (Lockheed Martin, Santa Barbara, Calif.) infrared camera (Model IC 11000) which has a thermal resolution of 0.015° C. FIG. 3 is a color infrared photograph showing temperature heterogeneity of a typical endarterectomy plaque specimen.

Surprisingly, it was found that there is poor correlation of heat with color in these plaque specimens, as can be readily appreciated in FIG. 1. Regions of similar gross appearance have different temperatures, and there is no obvious relationship of color to temperature. This was also true for the other plaques which were examined, as shown in the graph in FIG. 4. This poor correlation of regional color of the lumen surface to the regional temperature, as assessed in freshly harvested, living (unfixed) specimens of human carotid atherosclerosis obtained during endarterectomy was an unexpected observation. For example, red color, a classic sign of hemorrhage, does not adequately discriminate fresh from old hemorrhage in these tissues. Also, unperturbed blood may be less metabolically active than active thrombosis (e.g., heat of platelet release and coagulation enzyme reactions), or an organizing (inflammed) thrombus. The yellow color in vascular tissue may reflect cholesterol or esterified cholesterol, with varying amounts of carotene pigments. Moreover, little is known of the heat capacity, emissivity, insulation, and cooling rates of different cells and extra-celluliar matrix. White may indicate collagen, which is not metabolically active, or platelets, which emit heat upon activation. The surface color of a plaque region may also mask deeper colors.

In another series of investigations, Watanabe hypercholesterolemic rabbits were anesthetized and their aortas removed. Each aorta was quickly rinsed and studied by the thermistor technique described above and were also subjected to needle thermometry, routine photography, and infrared photography, as described above. Similar temperature heterogeneity was found in the rabbit aorta plaques (not shown).

Histology of "Hot" Plaques

Figure 6:
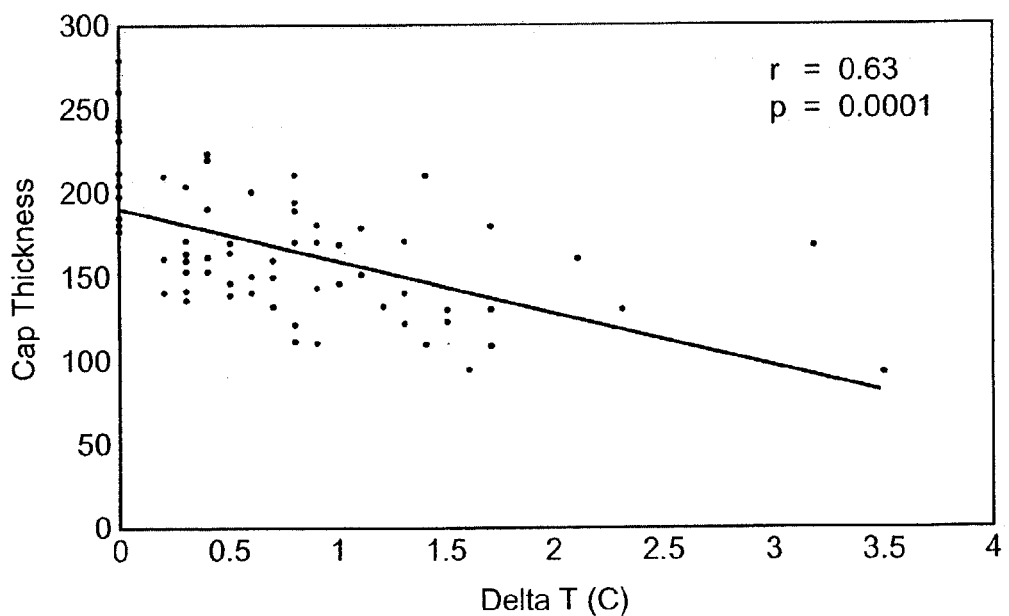
FIG. 6 is a graph showing the inverse relationship of lumen temperature measured by thermistor, to the depth of underlying cells in the plaque.
Figure 5:
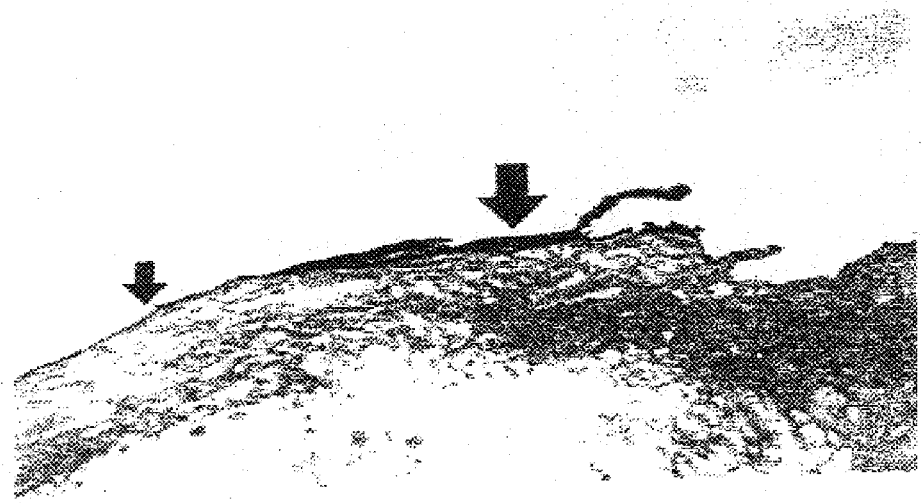
FIG. 5 is a color photomicrograph of a living human carotid atherosclerotic plaque marked in vivo by dye. The small arrow indicates a cool region adjacent to a 0.6° C. warmer region, indicated by a large arrow.
Figure 8:
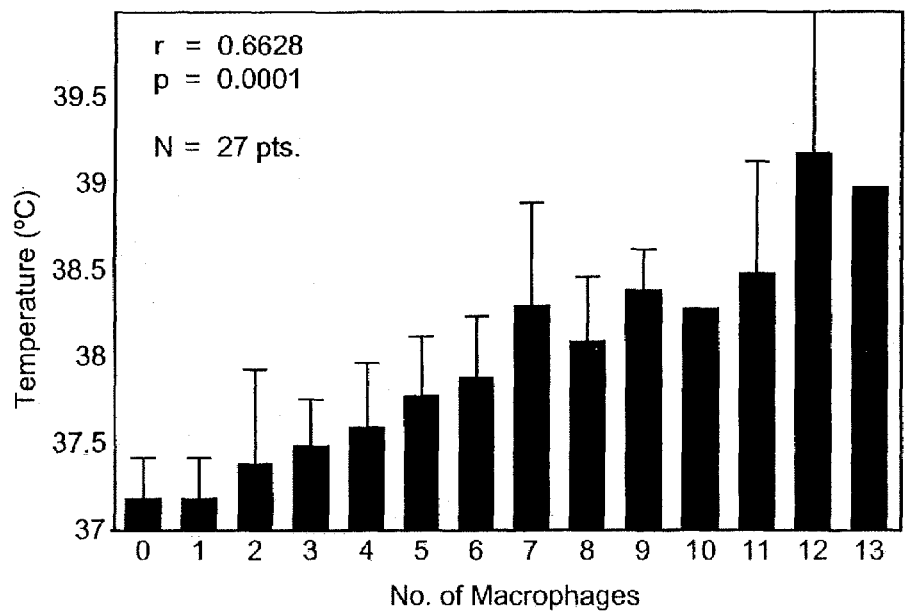
FIG. 8 is a graph showing the dependence of regional temperature on the number of macrophages in a region of freshly harvested living carotid endarterectomy specimen, as measured with a thermistor.

To elucidate this observed disparity between regional color and regional temperature, the inventors examined the histology beneath the color-coded temperature-mapped sections. FIG. 5 is a color photomicrograph showing the histology of adjacent regions in a living human carotid atherosclerotic plaque. A cool region is indicated by the small arrow and an adjacent (2.5 mm apart) 0.6° C. warmer region is indicated by the large arrow (also marked in vivo by dye). The cool region is relatively acellular while the cap beneath the warm region is inflamed. The graph of temperature vs cap thickness (FIG. 6) indicates that the deeper the clusters of cells with respect to the surface, the lower the temperature at the surface. The cap thickness was measured (in microns) from the lumen to the center of the cluster of underlying cells, of any morphology. The analysis arbitrarily included both acellular and hypocellular caps, since so few caps are completely acellular, and no distinction was made between endothelialized and non-endothelialized caps, nor was a distinction made between regions with a dense cluster of cells which might act as a point source of heat vs. regions with diffuse cellularity. Nevertheless, there was a statistically significant inverse relationship between cell depth (essentially, cap thickness) and surface temperature. Surprisingly, $1/(\text{distance})^2$ yielded no higher a correlation coefficient than $1/(\text{distance})$, suggesting to the inventors that a point source of heat is not an accurate assumption. In a subsequent series of plaques, it was found that there is a close correlation of heat with the density of monocyte-macrophages, as can be seen in FIGS. 7 and 8. FIG. 7 is a color photomicrograph of atherosclerotic plaque showing predominantly macrophaes (large arrow), as indicated by immunoreactivity (dark brown) with HAM-56 antibody. Some cells with the appearance of smooth muscle cells are lightly stained (non-apoptotic) and marked with small arrows. Asterisks denote venules in which most of the endothelial and smooth muscle cells are not undergoing apoptosis. FIG. 8 is a bar graph showing the dependence of temperature on the number of macrophages in a plaque region. In another series of 27 freshly harvested living carotid endarteroctomy specimens obtained from 27 patients, temperature was measured in a 37° C. incubator using a needle thermistor and colorfast dyes to relate the temperature to the underlying density of cells. Macrophages were identified by their typical morphology and correlated in the first few specimens by immunocytochemistry with HAM-56 and CD-28 antibodies, and by electron microscopy. The NIH image program was used to define a 200×400 micron area beneath the luminal dye marking each temperature. The density of macrophages is seen to account for approximately 44 percent of the temperature variance.

Figure 9:
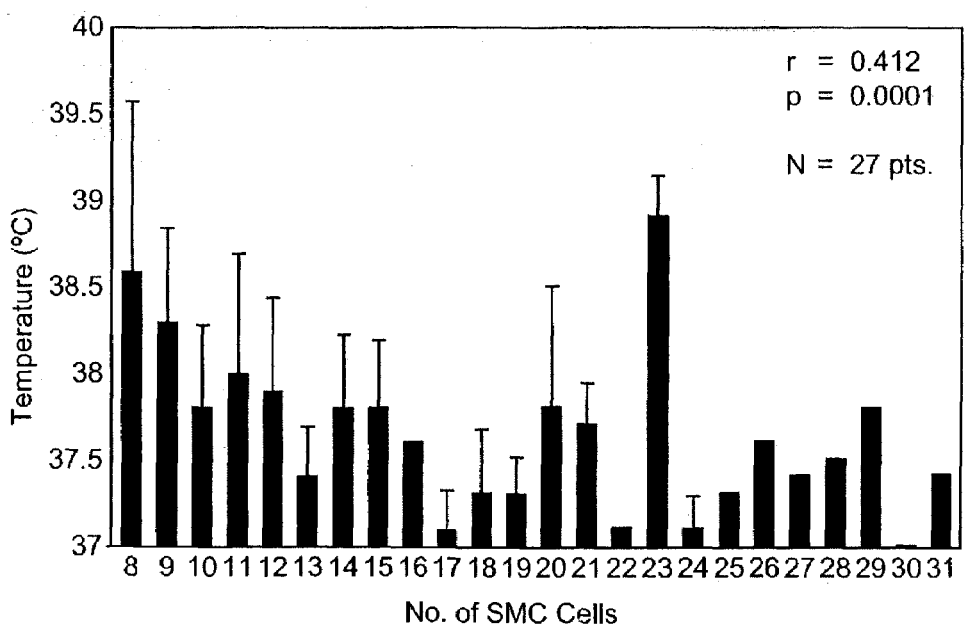
FIG. 9 is a graph similar to FIG. 8, but showing the lack of dependence of regional temperature on the number of smooth muscle cells in a region of freshly harvested living carotid endarterectomy specimen.

FIG. 9 is a similar graph plotting heat vs smooth muscle cell density. Temperatures were mapped by thermistor in a 37° C. incubator immediately after carotid endarterectomy. There is a negative correlation (−0.4) of heat with smooth muscle density. This paradox may be explained by the negative relationship between macrophage and smooth muscle cell density ($r=-0.72$). These observations lead the inventors to now suggest that macrophages generate much more heat than some SMC.

Relationship of Angiogenesis to Lumen Temperature

Figure 10:
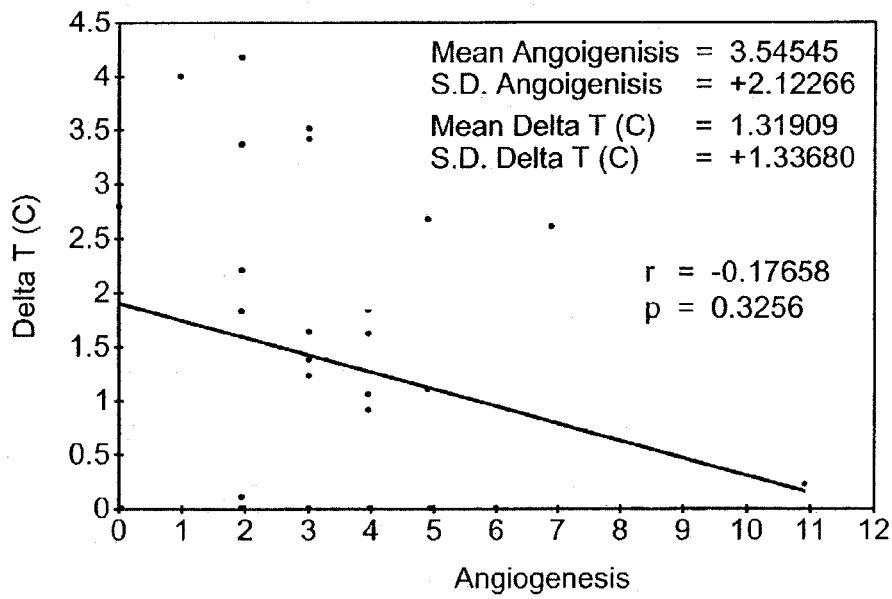
FIG. 10 is a graph showing a weak inverse relationship of relative lumen temperature to underlying density of microvessels (capillaries and venules) in a region of freshly harvested living carotid endarterectomy specimen.
Figure 11:
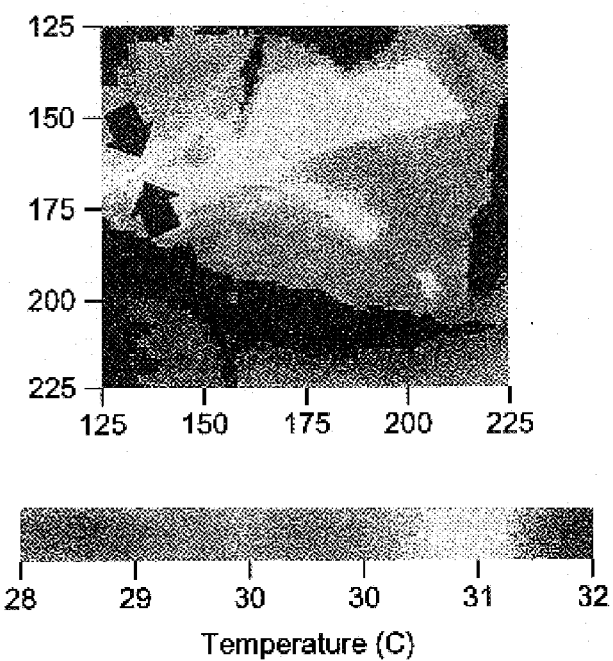
FIG. 11 is a color infrared photo showing in vivo temperature heterogeneity in the thoracic aorta of Watanabe hypercholesterolemic rabbit.

To determine if heat is merely a function of vascularity, e.g. heat brought from the body core to the plaque, lumen temperature was recorded in human carotid atherosclerotic specimens immediately after removal by carotid endarterectomy and was graphed against density of underlying capillaries and venules, as shown in FIG. 10. A weak negative correlation was observed, indicating that vascularity does not account for all of the observed thermal heterogeneity in plaque. Active macrophages in plaque may generate considerable heat, and this heat may be dissipated poorly (i.e., by radiation only) until plaque angiogenesis occurs, at which time the new vessels remove heat by convection. In intact plaque, blood flow may increase regional temperature or decrease it, by carrying heat away from a previously non-vascularized region. Further studies carried out in an animal model of atherosclerosis, temperature heterogeneity up to 1.5° C. (data not shown) inside the intact aorta of a Watanabe rabbit was measured using a thermistor catheter. Thermal heterogeneity was also demonstrated by IR thermography of the exterior of the aorta of another Watanabe rabbit, despite the presence of normal blood flow (FIG. 11). These data, together with the lack of correlation of heat with color (discussed above) lead the inventors to suggest that thermal heterogeneity of plaque is not just due to angiogenesis and/or vasodilation, and strongly support that the in vivo detection of thermal heterogeneity is feasible and desirable.

Correlation of Thermistor Temperature Measurement to Infrared Measurements

Figure 12:
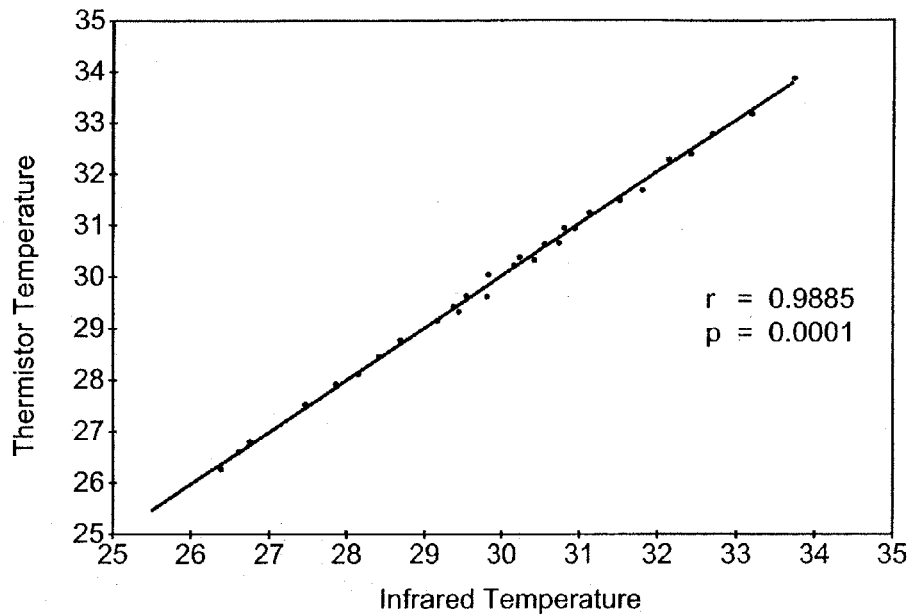
FIG. 12 is a graph demonstrating excellent correlation between thermistor temperature measurements of the lumen of a freshly harvested living carotid endarterectomy specimens and infrared camera temperature measurements.

Confirming the ex vivo studies in which thermal heterogeneity was detected by a thermistor and establishing the usefulness of an infrared catheter for making in vivo measurements, temperature heterogeneity in fresh endarterectomy plaque specimens was also detected using an infrared thermographic camera. This study was begun by confirming the correlation of mercury bulb thermometry with infrared thermometry, using heated beakers of water, which yielded a correlation co-efficient of $r=0.998$ (not shown). Because of the possibility that the emissivity of tissue would differ from that of water (despite the fact that tissue is mostly water), the correlation of the needle thermistor measurements with the infrared thermographic camera in living human atherosclerotic plaque, were first verified, as shown in FIG. 12. The graph of FIG. 12 demonstrates excellent correlation ($r=0.988$) between thermistor temperature measurements of the lumen and human carotid plaque specimens compared with measurements made with an infrared camera.

Figure 14:
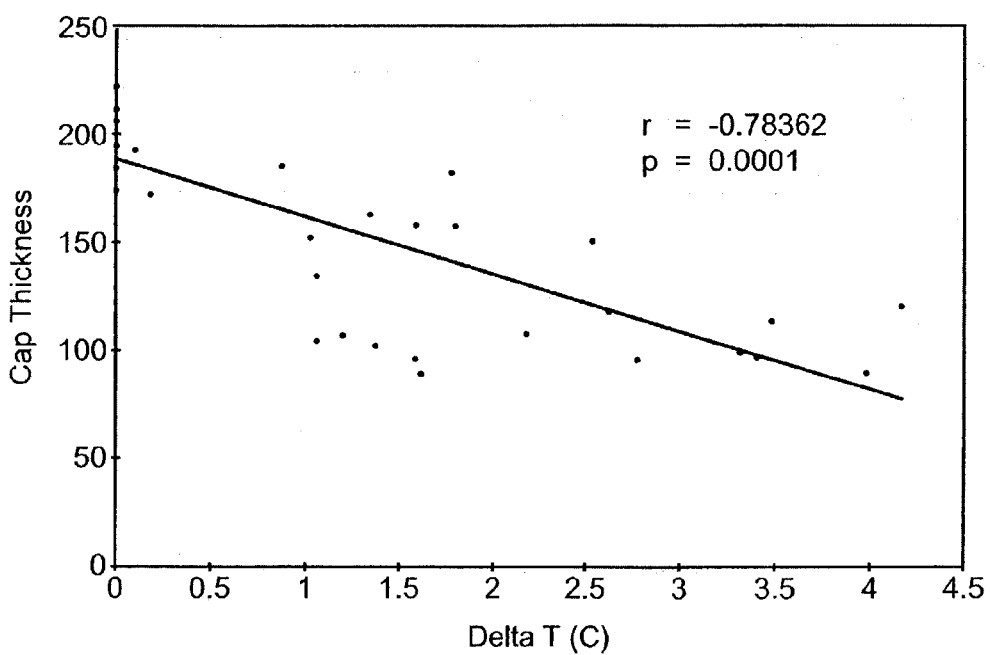
FIG. 14 is a graph showing the inverse relationship of lumen temperature to the depth of underlying cells in the plaque, similar to FIG. 6, except temperature was measured by infrared.
Figure 13:
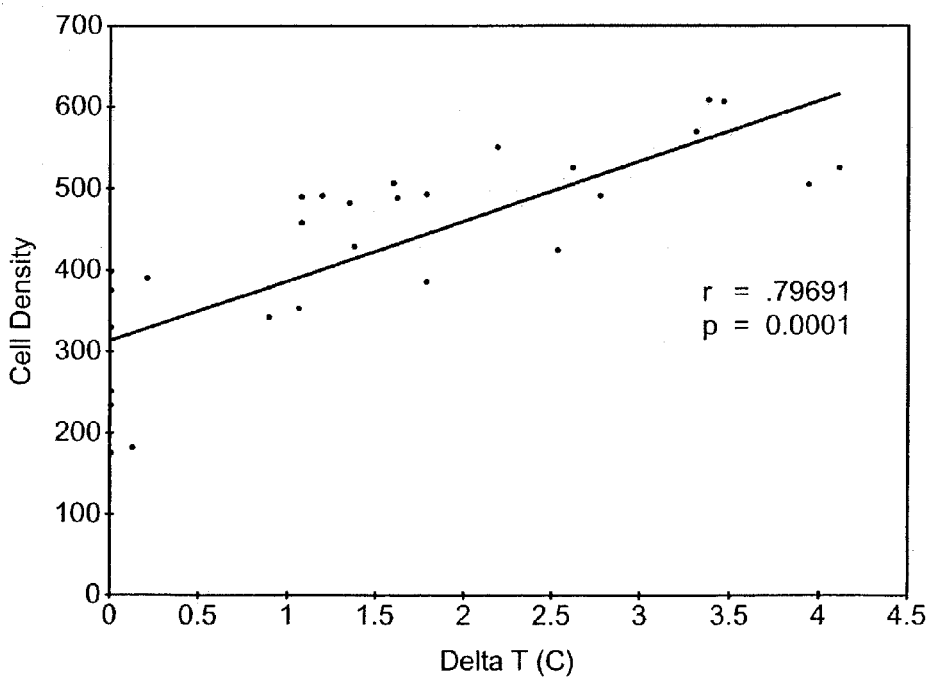
FIG. 13 is a graph similar to FIG. 2 except that temperature measurements were made with an infrared camera instead of a thermistor.

Next, the temperature vs cell density correlation studies were repeated, this time using an infrared camera and a fresh set of human endarterectomy specimens. FIG. 13 is a graph showing the relationship of lumen temperature, recorded with an infrared camera, to density of the underlying cells in 11 plaques. The relationship between temperature and cell density is tight ($r=0.797$, $p=0.001$). The distance from the lumen to the center of the cluster of underlying cells, of any morphology, was measured with the infrared camera, regardless of whether the cap was acellular or infiltrated, or its surface endothelialized or denuded. A graph of the results, shown in FIG. 14, depicts the inverse relationship of lumen temperature to depth of cells. Again there is an inverse relationship with the depth of the cells ($r=-0.783$, $p=0.0001$).

Referring again to FIG. 3, an infrared photograph was taken of the luminal surface of a typical plaque immediately after removal in the operating room. Excellent spatial and thermal resolution is demonstrated. This ex vivo infrared photograph of living atherosclerotic plaque removed by carotid endarterectomy was taken in a 23° C. room. The adjacent temperature scale in the figure reflects the calibration performed both electronically (by the "black body") and by correlation with beakers of water equilibrated at various temperatures and measured with a mercury thermometer. In this study, a warm central zone and a cool red island a few millimeters away were observed.

Therapeutic Implications

If continuing studies establish that a statistically significant proportion of hot plaques do indeed go on to develop superficial thrombosis and/or rupture, some interventionists may wish to treat such plaques with angioplasty on the grounds that rupture and/or thrombosis is better performed in a safe, controlled environment. Appropriate therapies other than angioplasty and stenting might include local treatment with anti-inflammatory drugs, antibiotics (Gupta et al. *Circulation* 96:404-7 (1997)) or cytokines, such as TGF beta-1, which is anti-inflammatory while at the same time stimulating SMC proliferation and matrix secretion (Grainger et al. *Nat Med* 1:74-9 (1995). A preferred method of treatment is gentle heating to induce apoptosis of macrophages, as proposed in U.S. Pat. No. 5,906,636. Treatments such as these may temporarily stabilize the patient until such time as atherosclerotic regression (in response to statins, aspirin, antioxidants, ACE inhibitors and lifestyle changes, for example) can take effect.

Other applicable therapies include local delivery of agents (peptides, peptide mimetics, oligonucleotides, and others) that prevent monocyte recruitment, attachment, activation, or DNA synthesis. Toward strengthening the plaque cap, collagen synthesis might be stimulated with ascorbic acid or transforming growth factor β (which also acts to inhibit angiogenesis, inflammation, and smooth muscle proliferation in most models, though it can also provoke inflammation in non-inflamed tissue and delay endothelial regeneration) (See Nathan, et al., *J Cell Bol* 113:981-986 (1991)). Endothelial regeneration can be enhanced by basic or acidic fibroblast growth factor or by vascular endothelial growth factor, among others (Casscells, *Circulation* 91:2699-2702 (1995)).

Since macrophage density has been reported by Moreno et al (id.) to be the best cellular predictor of restenosis, the heat-localizing techniques described above are also expected to be useful in predicting lesions at risk of restenosis so that appropriate local treatment can be instituted. Heat localization may also aid in predicting, and then preventing, progression of inflammatory aneurysms (Dobrin et al. *Ann N Y Acad Sci* 800:74-88 (1996); Freestone et al. *Arterioscler Thromb Vasc Biol* 15:1145-51 (1995)).

The type of medical therapy applied to a hot plaque would depend, in part, on whether the inflammation is on the surface or beneath an intact cap. This distinction may one day be facilitated by angioscopy (especially with the use of light-emitting antibodies) or by sampling blood for soluble markers of inflammation (P-selectin, VCAM-1, and others). As discussed above, magnetic resonance imaging, ultrasound, and near-infrared imaging may also prove helpful.

In summary, living human carotid atherosclerotic plaques exhibit thermal micro-heterogeneity attributable mainly to active macrophages at or near the lumen. These regions of increased temperature can be identified by intravascular techniques including infrared thermography, thermistors, thermocouples, MRI, liquid crystals and NIR spectroscopy; and by non-invasive thermal imaging techniques, including MRI, ultrasound and microwave. Vulnerable plaques at high risk of thrombosis or restenosis, or, in the case of adventitial inflammation, of aneurysmal rupture, are expected to be routinely treated by the above-described catheter-based and non-invasive means of imaging and treating these potentially life-threatening lesions. These techniques for detecting thermal heterogeneity are also expected by the inventors to find widespread use in many areas of medical specialization. For example, to detect subepithelial clusters of inflammatory or malignant cells in various organs by magnetic resonance imaging or by endoscopy, ophthalmoscopy, laparoscopy, artheroscopy, or transcranial imaging.

New Thermography Devices and Their Use

IR Fiber Optic Thermography Catheter Assembly

Figure 15:
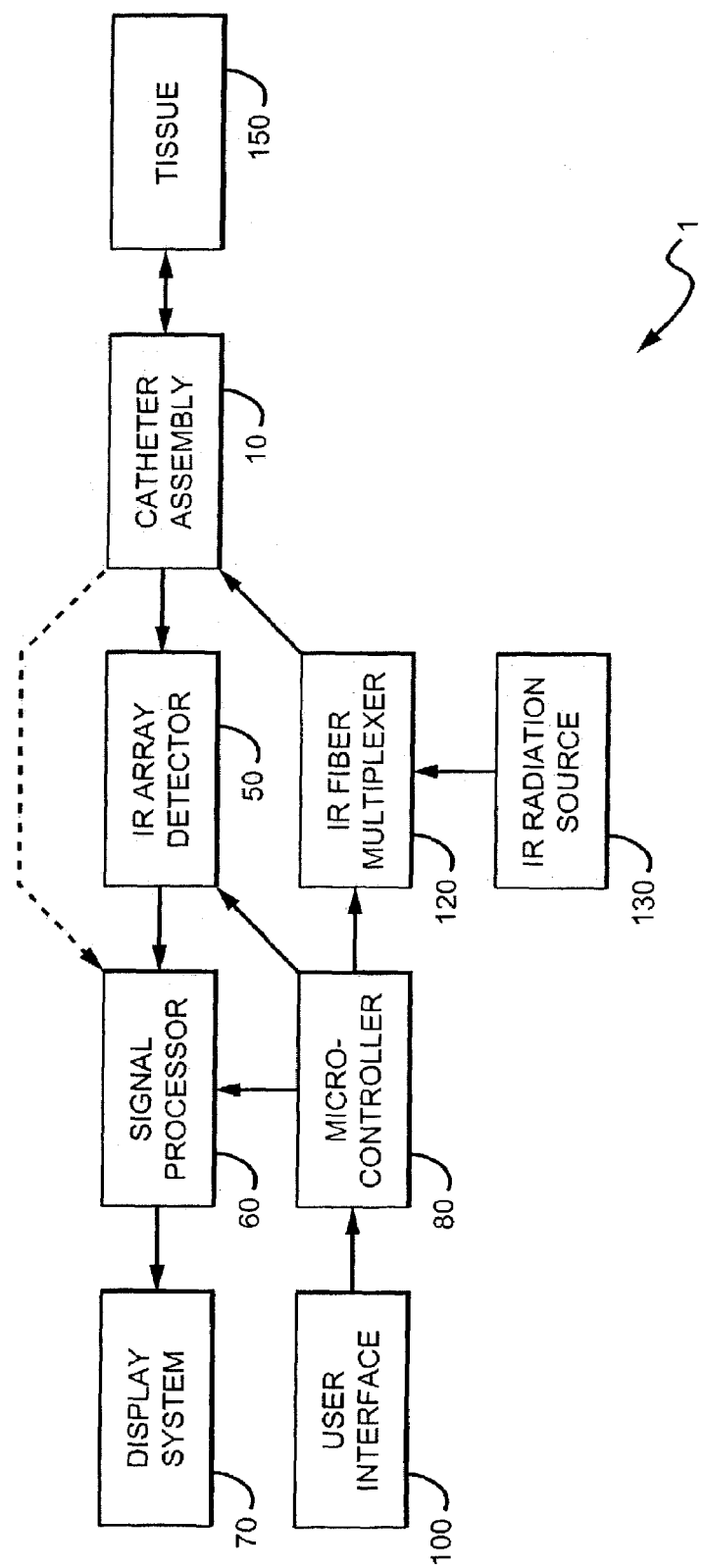
FIG. 15 is a schematic diagram of an embodiment of the heat detection assembly of the present invention.

FIG. 15 shows a block diagram of an infrared thermography assembly 1 for detecting vulnerable atherosclerotic plaque in a living vessel. Assembly 1 includes infrared catheter assembly 10, IR array detector 50, signal processor 60, display system 70, microcontroller 80, user interface 100, and optional IR fiber multiplexer 120 and IR radition source 130. User interface 100 preferably includes a power switch and such other controls as may be needed for operating assembly 10. User interface 100 may operate in conjunction with display system 70 to provide menu-driven control of assembly 10. Microcontroller 80 may be a hardware implementation of a state machine, but is preferably a general purpose microcontroller which operates on software instructions stored in a nonvolatile memory. Microcontroller 80 controls IR array detector 50 and signal processor 60. In an alternative dual function heat detection/heat delivery embodiment, microcontroller 80 implements a state machine for controlling the operation of infrared light source 130 and IR fiber multiplexer 120. Infrared radiation source 130 is preferably a broad band source such as a commercially available GLOBAR™ lamp (Cesiwid Inc., Niagra Falls, N.Y.). Signal processor 60 is preferably a general purpose digital signal processor which operates on the digital signals from the detector 50 according to software stored in a nonvolatile memory (not specifically shown). Values generated by signal processor 60 are provided to display system 70 for viewing by the user, or may be output to a printer or in electronic format. One form of output may be desired over another for a particular situation. The measurements and indicators are preferably displayed in numerical form, although graphical image form may also be used. When catheter 140 or 340 is provided with a capability for transporting visible or near-infrared light (as discussed elsewhere), signal processor 60 may also process the corresponding signals, to generate a visible-light image of the interior of the vessel for display by display system 70, for example. In alternative embodiments, the microcontroller 80 and signal processor 60 functions may be performed by a single processing unit, and in some embodiments the infrared signal is received by a video camera operatively connected to a computer.

IR Fiber Bundle Catheter Assemblies

FIG. 16 shows a perspective view of an embodiment of the infrared catheter assembly 10 of thermography assembly 1.

Catheter assembly 10 has a distal end 11 and a proximal end 16. Assembly 10 includes an infrared catheter 40 having a distal tip 41 for inserting into a vessel. Proximal end 16 (located outside the body during use) terminates in connector assembly 18. Infrared catheter 40 extends from manifold 30 to distal end 11 of catheter assembly 10. The assembly may also include a catheter introducer 20 (shown in FIGS. 18 and 19).

FIGS. 19A-C and FIG. 20A depict an infrared catheter 40 that has a distal tip 41 and contains within its walls 43 a guidewire lumen/flushing lumen 42, an infrared fiber bundle 44 and a reflective surface 46. A circumferential window 48 is located in wall 43 of catheter 40. Window 48 is a fluid-tight transparent or IR transmitting surface in wall 43. Optical fiber tips 45 are directed at reflective surface 46 which is positioned near distal tip 41 for directing infrared radiation arising radially to the fibers into discrete fiber tips 45. Preferably reflective surface 46 is a substantially conical or frustoconical radial view mirror, as shown in FIGS. 19A-C and FIG. 20A. Instead of being flat, the reflective surface may be slightly curved or concave in order to collect infrared radiation from a wider subtended area of vessel wall (i.e., a fish eye view).

Figure 19B:
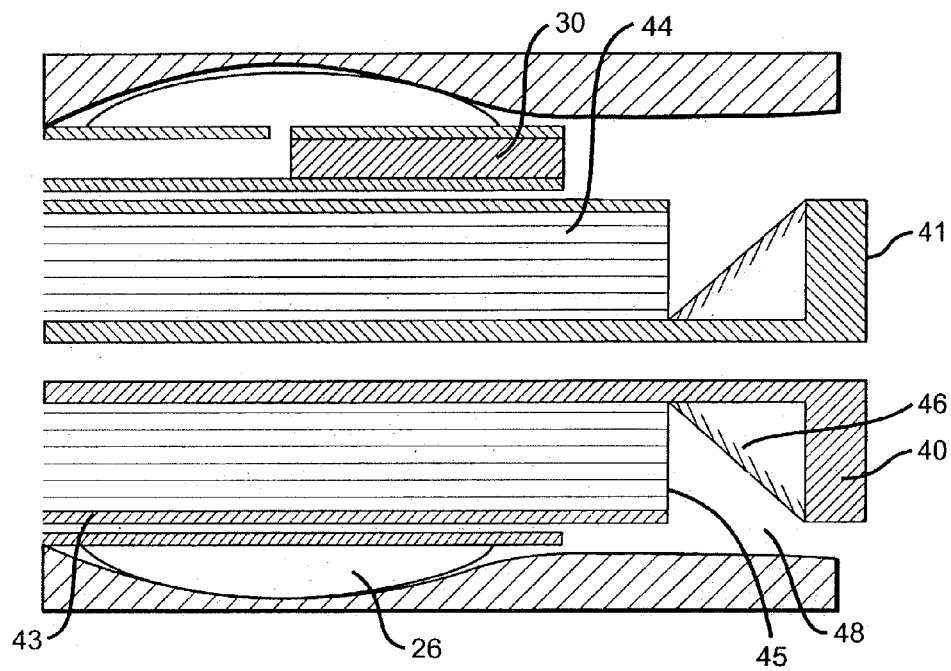
FIG. 19B is like FIG. 19A but shows the infrared catheter advanced further into the vessel.

The guiding catheter or catheter introducer 20 of catheter assembly 10, shown in FIGS. 18, 19A-B and 20A, is similar to conventional cardiovascular introducer catheters but includes an inflation lumen or air lumen 22 extending lengthwise along a section of the interior wall 24, an air outlet 27, and an inflatable balloon 26 joined circumferentially to the outer wall 23 of guiding catheter 20 adjacent distal end 28. Inflation lumen 22 is in fluid communication with balloon 26 via air outlet 27. Balloon 26 is shown in its inflated state in FIGS. 4, 5A, 5B and 6. Balloon 26, which is preferably similar to a conventional angioplasty balloon. Introducer catheter 20 contains an interior lumen 25 for receiving infrared catheter 40, as shown in FIG. 19A. Alternatively, the catheter assembly 10 may include a transitional catheter which does through the guiding catheter 20 and carries the IR catheter 40. In this case, the balloon and inflation lumen are on the transitional catheter instead of the guiding catheter.

Figure 17C:
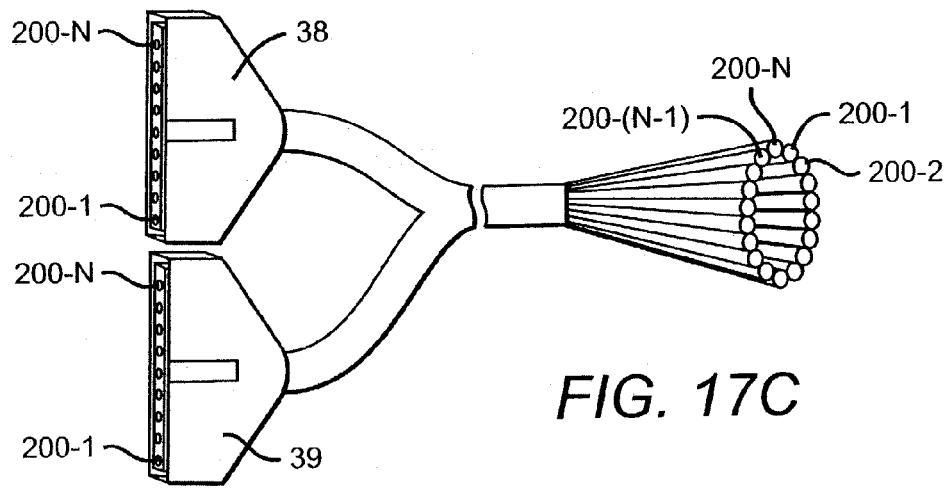
FIG. 17C illustrates the spatial relationship of the coherent optical fibers in relationship to the detection and multiplex connectors shown in FIG. 17B.
Figure 17D:
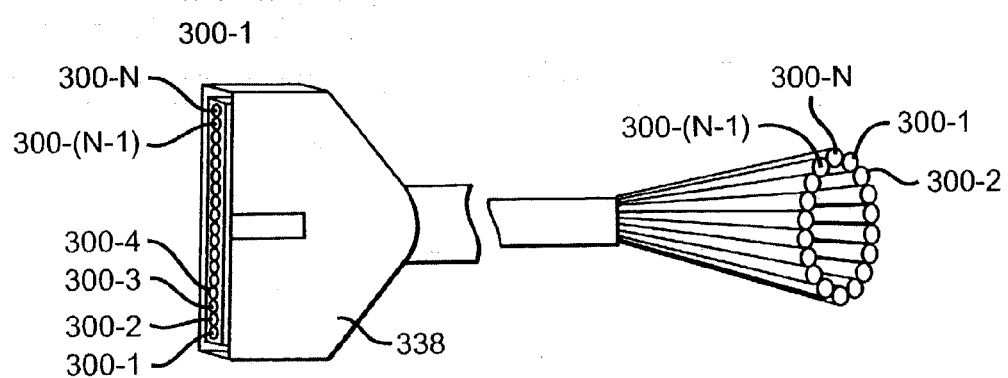
FIG. 17D illustrates an alternative embodiment of the assembly of FIG. 17C in which a separate multiplex connector is omitted.

Optical fibers 44 are "coherent" fibers which couple to a dector 50 via connector 38 (shown in FIGS. 17A-B). The individual optical fibers are arranged in circumferential order within catheter 40 at the distal end 41, and this ordered spatial relationship is preserved by connector 38 and IR fiber bundle splitter 33. For some purposes it is preferred to have both diagnostic and therapeutic capabilities on a single catheter assembly. This avoids the problem of marking the hot plaque through fluoroscopy and returning later with another catheter to treat the targeted plaque. For this purpose, an optional IR heating modality may be included (as shown in the block diagram in FIG. 15). In this case the reflective surface 46 of the catheter shown in FIG. 19C also serves to direct IR radiation emerging from the coherent fibers through window 48 onto the targeted region of vessel wall. The catheter designs shown in FIGS. 20 B-C can also be varied to include an IR heating modality in addition to the IR detection modality. In this case, connector 39 is also present (as shown in FIG. 17C) and is in operative communication with a portion of the fiber array and with multiplexer 120 when delivery of heat to through discrete fibers is desired. Alternatively, IR multiplexer connector 40, fiber bundle 46b and fiber array 52 are omitted, and IR array detector 38 is adapted for being detached from detector 55 and attached to IR radiation source 130, for introduction of IR radiation to discrete IR fibers in array 52 under the control of microcontroller 80 (as illustrated in FIG. 17D).

FIG. 17A provides a detailed view of one embodiment of proximal end 16 of catheter assembly 10. Connector assembly 18 includes a manifold 30 from which branch inflation connector 34 and catheter 40, containing imaging bundle 44 and guidewire/flushing lumen 42. Access to guide wire lumen 42 is also provided by guide wire inlet 42a. An infrared camera is shown operatively positioned adjacent the proximal end of imaging bundle 44, and is also operatively connected to a processor, such as a computer.

In a variation of this design (FIG. 17B), the proximal end of catheter assembly 10 includes a manifold 230, inflation connector 234, a guide wire/flushing connector 242, an IR bundle splitter 233, an IR detection connector 238 and an IR multiplexer connector 239. Detection connector 238 is configured to couple to signal processor 60 and to receive a signal from the discrete fibers which comprise fiber bundle 44a (shown in FIG. 17C, 17E). IR multiplexer connector 120 is configured to couple to IR radiation source 130 to transport infrared radiation via connector 239 to discrete fibers which comprise fiber bundle 44b (shown in FIGS. 17E, 17G).

Alternatively, IR multiplexer connector 120 is omitted ad IR detection connector 338 (FIG. 17D) is detachable from dector 50 and attachable to IR radiation source 130, for introduction of IR radiation to fiber bundles 44a,b (FIGS. 17F, 17H) under the control of microcontroller 80. For example, catheter assemblies employing either of the IR catheters shown in FIGS. 20B and 20C may be modified in this way.

Inflation connector 34 or 234 is configured to couple to a conventional balloon inflation source and flushing connector 42a or 242 is configured to couple to a fluid source, such as isotonic saline. The balloon inflation source preferably provides air at a the desired pressure.

Figure 4:
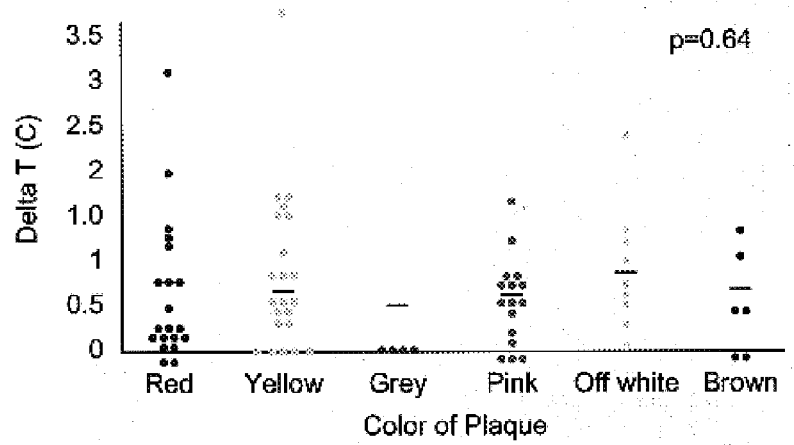
FIG. 4 is a graph showing the poor relationship of regional color differences of the lumen surfaces to regional temperature in a freshly harvested living (unfixed) specimen of human carotid atherosclerosis obtained at endarterectomy.
Figure 20B:
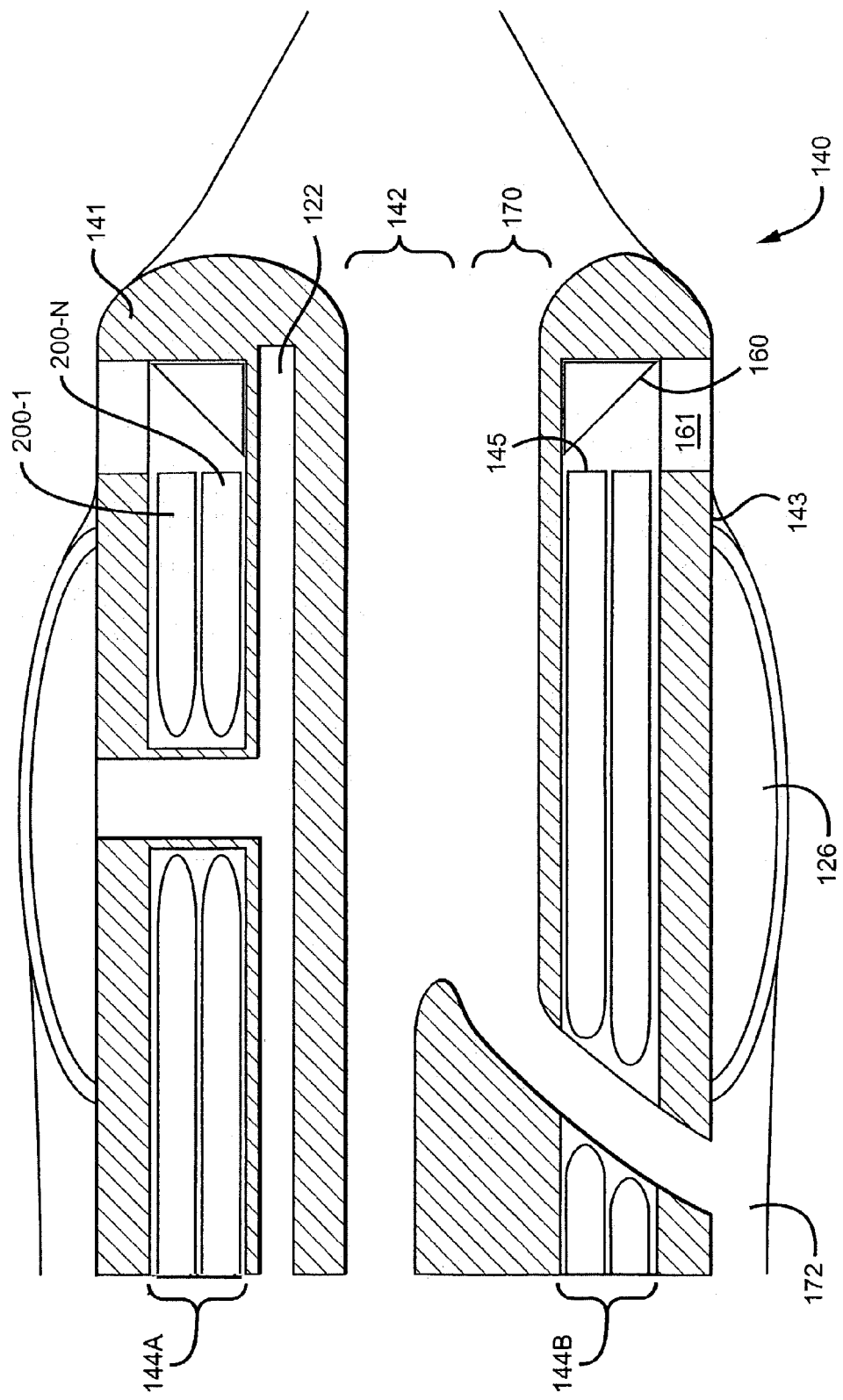
FIG. 20B is an alternative embodiment of the IR imaging catheter of the invention employing a reflective surface for directing infrared radiation.

Referring now to FIG. 20B, the distal end 141 of an alternative IR catheter 140 is shown as operatively positioned inside a vessel. Catheter 140 includes a centrally disposed wire lumen 142, a perfusion lumen 170, a perfusion inlet 172, a balloon 126, an inflation lumen 122 and two IR imaging bundles 144a,b each having a plurality of fibers 200-1 through 200-N (FIG. 17E) which terminate in an array opposite mirror 160. Mirror 160 is situated inside catheter 140 adjacent end 141. Catheter window 161 is a circumferentially located in the catheter wall 143 adjacent distal end 141. Mirror 160 can be flat, but is preferably curved so that the temperature of a larger area can be mapped, consistent with the size of a typical vulnerable plaque (e.g., about $0.5 \times 1$ cm$^2$) and the desirability of imaging as much atherosclerotic area and normal area as practical. If desired, an array of NIR or visible optical fibers may be substituted for a portion comprising at least one layer of IR fibers in order to provide supplemental visual imaging or NIR spectroscopy, in addition to the thermal imaging. Various configurations of the mirror or reflective surface 160 (shown in FIG. 20B) may be employed at the tip of catheter 140, as shown in FIGS. 20D-1 through 20D-4. The reflector surfaces are preferably polished metal, coated with highly reflective materials such as gold, or aluminum. In FIG. 20D-1, a conical surface reflector is shown where the mirror surface and the fiber axis form an angle between 0 and 90, preferably 45°. The arrows indicate incident and reflected radiation. FIG. 20D-2 illustrates a convex surface at each cross section form a cone which will reflect a wider area of lumen wall onto fiber bundle. Step wise mini reflectors also reflect a wide area of lumen wall onto fiber bundle, as shown in FIG. 20D-3. This configuration can also make a one-to-one correlation with each fiber layer, as shown in FIG. 20B. A concave reflector which will focus a narrower area of the lumen wall, as shown in FIG. 20D-4, which may be desirable for certain applications.

Figure 20C:
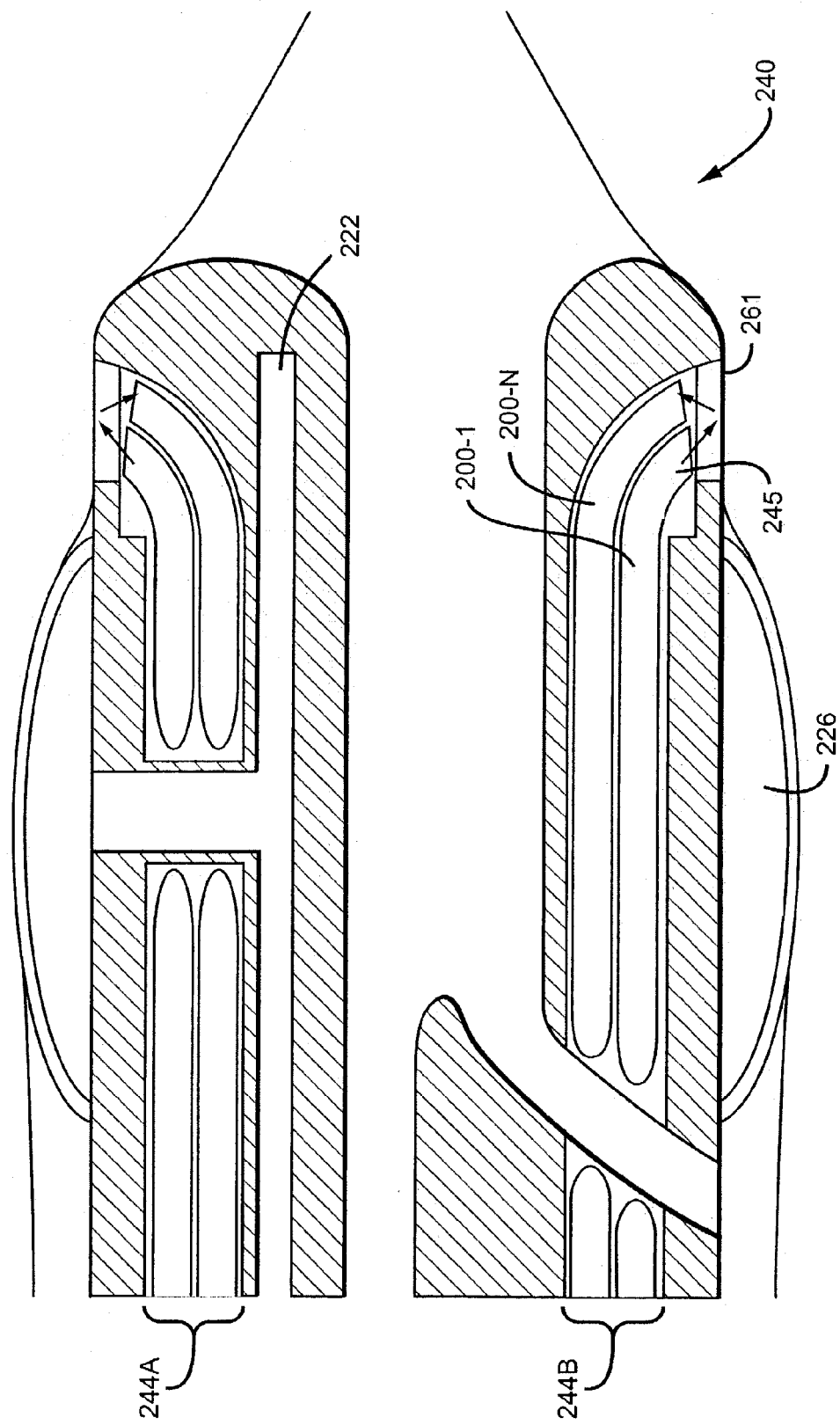
FIG. 20C is another alternative embodiment of the IR imaging catheter of the invention illustrating bent tip fibers.
Figures 2, 20D:
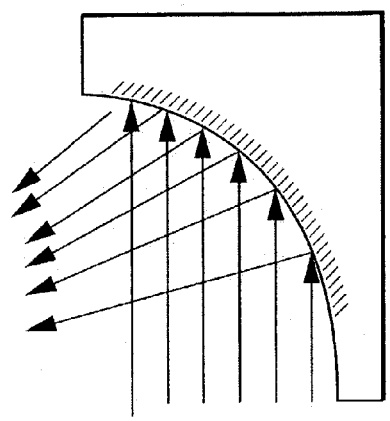
Figures 4, 20D:
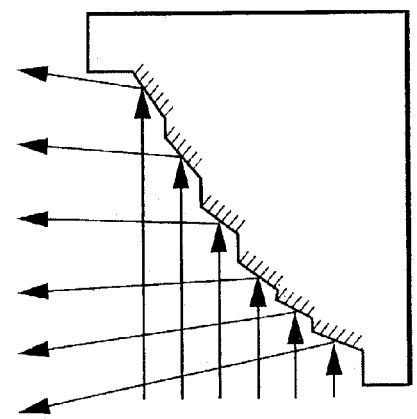
Figures 1, 20D:
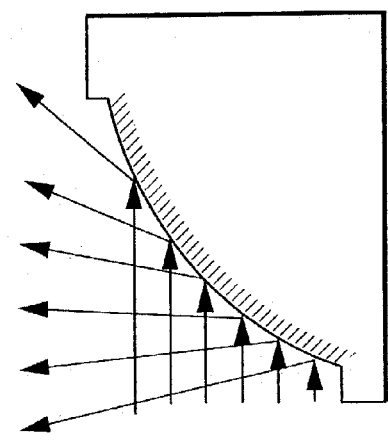
Figures 3, 20D:
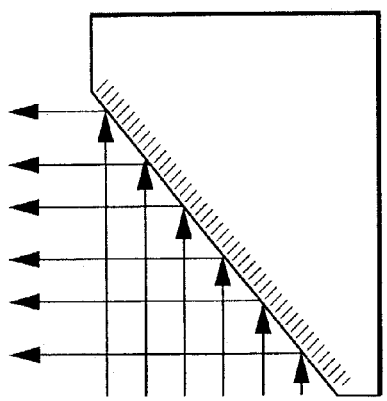

Another alternative IR catheter shown in FIG. 20C is like the catheter shown in FIG. 20B except mirror 160 is eliminated, and instead fiber tips 245 are slightly bent and terminate adjacent window 261. FIG. 20C is a cross-sectional view showing the individual fibers of optical fiber bundles 244a,b bent radially outward at their distal tips 245. IR radiation emitted from arterial wall tissue 151 passes through window 261 into distal tips 245 and is conveyed by the fibers back to detector 50. In FIG. 20C, the arrows indicate the direction of incident and reflected light. For some applications, the bent tip embodiment might be preferred over the straight-tip-with-mirror embodiment of FIG. 20B. For ease of manufacturing, some users may prefer the straight tip version.

Referring again to FIG. 17E, a partially cut away view of the distal portion of the catheters of FIGS. 20B-C is shown, with the tip of the catheter removed. The arrayed fiber tips 145 or 245 are gathered from their circumferential positions into bundles 144a,b or 244a,b. Inflation lumen 122, 222 and guidewire/flushing lumen 142 and 242 are each shown entering a divided portion of conduit 149, 249 of catheter 140, 240. The cross-sectional view of conduit 149, 249 shown in FIG. 17G illustrates one way the fiber bundles 144a,b or 244a,b, inflation lumen 122, 222 and guidewire/flushing lumen 142, 242, may be spatially arranged along the length of catheter 140, 240. The guidewire lumen passes along the central axis of the catheter, and the annular space between the guidewire lumen 142, 242 and the wall 143, 243 of the catheter 140, 240 may be divided by radial walls 175, 275, which extend proximally through the catheter. In the divided annular spaces 172, 272 the fiber bundles 144a,b or 244a,b are placed, as well as the inflation lumen. Although the inflation lumen is shown as a tube within a divided annular segment, it is understood that the entire divided segment can be used as a lumen for transporting the inflation medium, for ease of construction. FIG. 17C shows the relationship between the distal and proximal ends of the arrayed individual fibers 200-1 through 200-N or 300-1 through 300-N. The individual fibers are arranged in order around the circumference of catheter 140 or 240 at the distal end 141, 241 and this ordered spatial relationship is preserved by connector 138 or 139. FIG. 17D is similar to FIG. 17C but shows the relationship when connector 139 is eliminated and connector 138 is instead adapted for coupling with either the dector 50 or multiplexer 120.

FIG. 17H illustrates how the lumens and fiber bundle shown in FIG. 17F may be spatially arranged and routed through the catheter from the distal to proximal ends, in embodiments in which connector 239 is not present.

If desired, an ultrasound transducer/receiver is employed in combination with one of the above-described IR catheters to increase the diagnostic power of the catheter assembly. A conventional intravenous ultrasound (IVUS) wire that is small and flexible (such as IVUS made by EndoSonics Corporation, Rancho Cordova, Calif.) can be incorporated into the above-described IR catheters, and is preferably threaded to the tip of the catheter through the guide wire lumen.

Fiber Optic Materials

Optical fibers are well known for a wide range of applications in telecommunication, medicine and industry. A coherent image fiber bundle, also known as an aligned image bundle, is an assembly of fibers in which the coordinates of each fiber are the same at the two ends of the bundle. Generally, a coherent bundle is used where spatial resolution is important. For example, it can be used to transfer the image plane remotely or locate an object. This is a desirable capability in the present case for locating plaque heterogeneity. Most conventional fiber optic applications use silica-based glass fibers. Optical fibers fabricated with silica-based glass have achieved the intrinsic attenuation limits of 0.2 dB/km at 1.5 μm. However, the transmittance wavelength range of silica-based fibers is limited below 3 μm, which covers the visible and near-infrared wavelengths.

In biomedical and some industrial applications, the mid-infrared wavelength range (i.e., 2.5-25 μm) of the electromagnetic spectrum is of primary interest. IR fiber optics that transmit from 2-14 μm require entirely different materials for their fabrication, however, in order to avoid appreciable loss of energy during transmission. These mid-IR wavelength transmitting materials include halide crystals and glasses, semiconductor crystals and glasses, heavy metal oxides and metals. Polycrystalline fiber optic materials have been fabricated from the halides of silver, thallium, and potassium. Silver halides (AgCl—AgBr) are currently the most commonly used materials. Chalcogenide glasses are those multi-components glasses containing the group VI elements S, Se or Te as the network forming anions and cations such as As, Ge, and Sb. The heavy metal fluoride glass optical fibers are similar in many ways to the silica based fibers and only transmit the IR radiation up to 4.5 μm. Single-crystals of $Al_2O_3$ or sapphire fiber optics can sustain high temperature and harsh environment.

Fibers that differ in attenuation, strength and flexibility are prepared from chalcogenide glasses in a number of different ways that are known in the field. The composition from the AsSeTe system (C1), shows less than 1 dB/m attentuation in the wavelength range of 2-14 μm. This process is also used to produce C2 fibers from $As_2S_3$ glass. The C2 fibers cover the wavelength range from the visible through near infrared (0.7-7 μm), with less than 1 dB/m attenuation. Both C1 and C2 fibers are chemically inert, not attached by moisture, unaffected by weak acids and bases, and resistant to attack by most organic solvents. The IR image fiber bundle catheters described above employ a coherent image fiber bundle consisting of mid-range IR transmitting optical fibers. Owing to the flexibility of preferred fiber bundles, they can be used for thermal imaging in relatively inaccessible areas. An exemplary fiber optical imaging bundle consists of a 30×30 square infrared optical fiber array of 900 individual $As_2S_3$ chalcogenide glass fibers and has a diameter of about 6 mm or less. In preliminary studies, a 900 fiber bundle that was 1 meter long bundle and only 100 μm in diameter demonstrated very good flexibility for vascular use. The bend to break radius for the $As_2S_3$ fibers used in the catheter is 0.1 cm/Tensile Strength 122,000 psi at 40 Mpa/sec Strain Rate. The chalcogenide glass fibers transmit infrared radiation from 0.7-7 μm with relatively small energy loss (less than 1 decibel/meter). As fiber technology improves and smaller diameter fibers become available, fibers of about 25 mm will be used to improve spatial resolution 4-fold. Accordingly the number of fibers carried in a 6 mm catheter will increase to about 15,000.

Figure 22C:
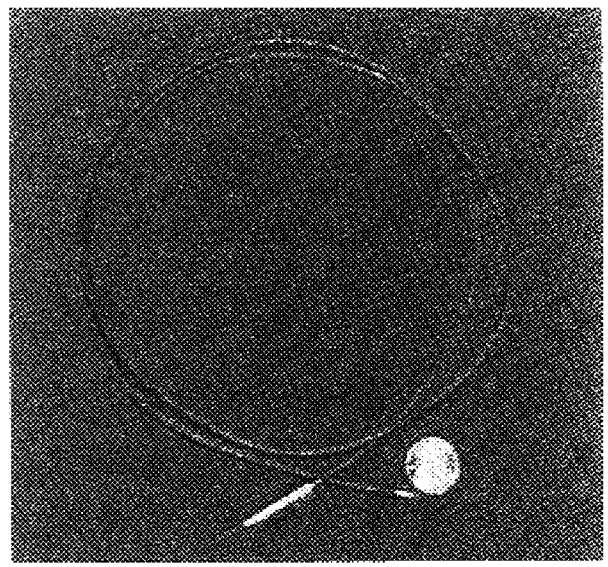
FIG. 22C is a photograph of a 1 meter long×3 mm O.D. catheter containing a 100 fibers imaging bundle.

The catheter is relatively steerable and torquable and has a soft tip to protect the vascular tissue. The overall flexibility of the catheter is about the same as similar-sized cardiovascular laser, fiberoptic, angioplasty and atherectomy catheters. The material of the catheter body is preferably similar to that of a conventional Swan-Ganz catheter, or any suitable material such as high strength polyester or polyethylene terephthalate (PET), which is clear and easily extruded in ultrathin wall sizes. A high strength braided polyester is useful for translating twisting motions over long distances as may be required in certain embodiments. The materials of which the catheters arc constructed may be any of those commonly used, including flexible plastics such as nylon, Teflon™, vinyls such as polyvinyl chloride, polyurethane, and polyethylene, or various rubber compounds. Preferably the catheter is about 12-100 centimeters long and has an outer diameter of about 3-4 millimeters or less, for human use in the peripheral vessels, and 2 mm or less in diameter for delivery to the small-diameter coronary arteries, as illustrated in FIG. 22C. In the unexpanded configuration, the outer diameter is preferably no more than 0.5-3 mm for coronary catheters and 2-8 mm for peripheral (e.g., femoral) arteries.

The minimum thermal resolution of the heat detection catheter for best clinical utility is about 0.2° C., and the spacial resolution≦1 mm or less. While the devices of the invention are capable of finer thermal discrimination (i.e., about 0.1° C. or less), biological variables are apt to introduce noise into the system. The accuracy, or validity in determining absolute temperature is less critical than the relative temperature measurements, but it is at least 0.5° C. in the preferred catheters. In most instances, plaques that are in danger of rupturing will vary from those less at risk by at least 1.5° C.

The prototype IR imaging optics fiber bundle (a 30×30 square infrared optical fiber array of 900 individual $As_2S_3$ chalcogenide glass fibers) was initially tested using a simple phantom, coupling the fiber bundle directly to the 25 mm camera lens (Amber InSb FPA IR Camera NEDT=18 mk; 256×256 pixel; Raytheon, Goleta, Calif, 93117), which was mounted to a lens extender provided by the manufacture. This configuration allowed focusing of the proximal end of the fiber bundle onto the FPA detector, but sacrificed the temperature calibration of the IR camera. The phantom consisted of a plastic plate supported by four rods of different material (brass, solder lead, plastic and wood). The 1.5 mm (1/16 inch) diameter rods were about 40 mm long and were embedded through the plastic plate to form a diamond shape of different material. The distance between rods was about 3 mm. The bottom ends of the rods were connected together with a brass block. Tile surfaces of the plastic plate and four rod locations were painted with black paint to have a uniform emissivity. When the bottom brass block was heated to a fixed temperature, the different thermal conductivity of the four different materials led to four different temperatures on the surface of the phantom. This can be easily distinguished in the IR images shown in FIG. 22A, with the brightest spot being brass (31.8° C.) followed by the lead rod (29.3° C.). The plastic rod (28.6° C.) is much dimmer, and the wooden rod (28.3° C.) is barely visible in the thermogram. When the IR fiber bundle was placed directly on top of the brass rod the bright spot of the brass rod end markedly differs from the surrounding plastic, as shown in FIG. 22B. Images were taken with and without bending the bundle 180°, and while some attenuation was apparent it did not preclude imaging in the bent configuration. With a precise temperature calibration, temperature differences are measured remotely with a relatively high sensitivity and accuracy using the IR imaging fiber bundle.

IR Thermography Catheter Assembly

Figure 22D:
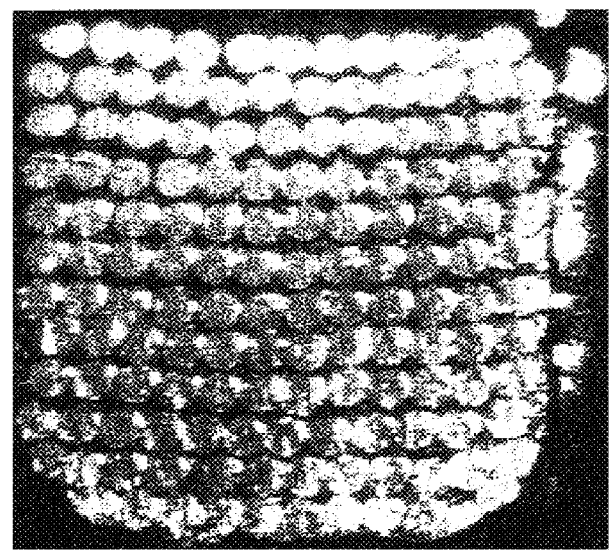
FIG. 22D is a photomicrograph of the distal end of the fiber bundle used in the catheter shown in FIG. 22C.
Figure 22E:
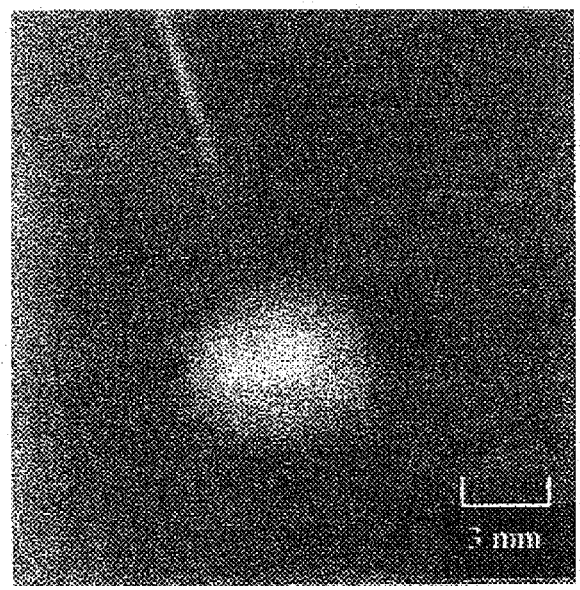
FIG. 22E is a color photograph of a temperature sensitive liquid crystal sheet overlying the ends of the brass and lead rods of the temperature phantom employed in the studies shown in FIG. 22A and FIG. 22B.

A prototype fiber optical imaging bundle consisting of 900 individual $As_2S_3$ chalcogenide glass fibers was used in initial tests. The fibers are arranged in a 30×30 array, which transmit infrared radiation from 0.7 μm to 7 μm, with little energy loss. A highly sensitive Indium Antimonide (InSb) infrared focal plane array (FPA) detector is connected to the proximal end of the fibers. The Focal Plan Array (FPA) detector is cryogenically cooled with a Stirling engine. The detector array preferably has 256×256 pixels. and each pixel is 38 μm×38 μm. The initial prototype IR fiber imaging bundle for the heat-sensing catheters worked well both in vitro and in vivo. However, that device has not yet been employed for in situ testing of the cardiovascular lumen simply because of its size, i.e. about 6 mm OD. Since the technical improvement necessary in order to draw smaller fiber is still under development by the manufacturer (Amorphous Materials, Garland, Tex.), the initial in vivo fiber bundle imaging is carried out using fewer fibers in order to reduce the bundle's diameter. A 1 meter long 10×10 fiber bundle in a catheter having 3 mm O.D. is shown in FIG. 22C. A microscopic image of the 100 fiber array is shown in FIG. 22D. The smaller diameter permits cannulation of smaller arteries. To overcome shortcomings of "forward looking" fibers. the most preferred designs include a "side-looking" capability. This can be accomplished by placing a reflector at the tip of the catheter, such as the conical mirror illustrated in FIGS. 20A and 20B. Some suitable reflectors are reflector cones, convex or concave reflectors. Also, a prism could be used. It is best to coat the reflector with a high IR-reflecting material such as gold or aluminum.

The number of fibers will be increased as smaller diameter fibers become commercially available, in order to further improve the resolution. This IR bundle catheter is capable of measuring the temperature of a circumferential array of vessel wall sites with sufficient sensitivity to distinguish temperature differences as small as 0.2° C.

Figure 19C:
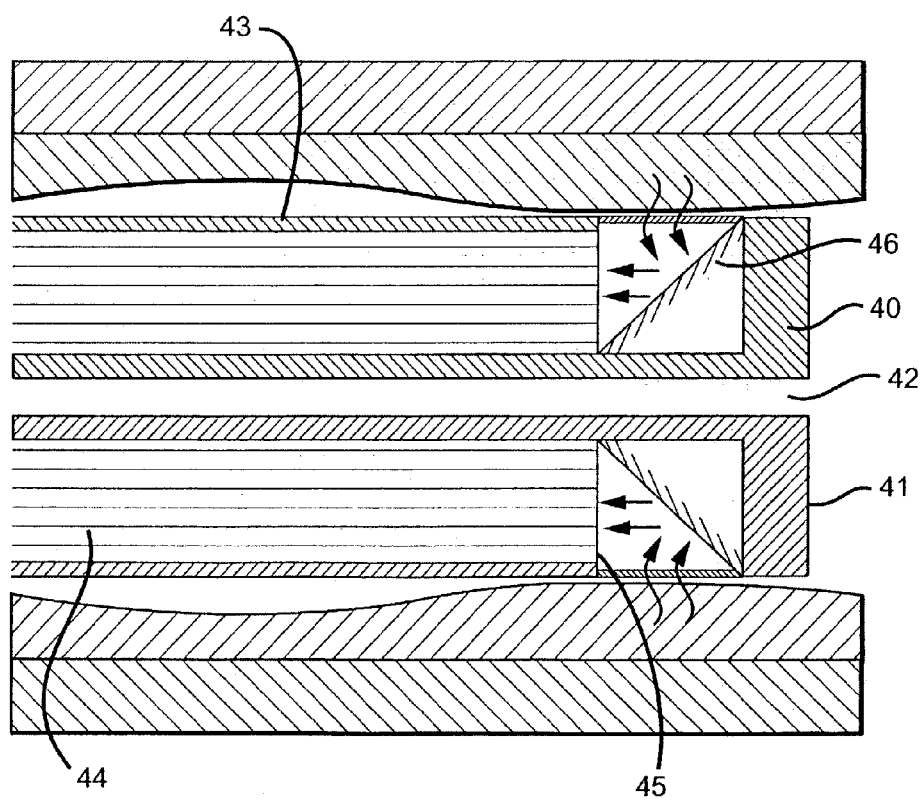
FIG. 19C shows the tip of the infrared catheter shown in FIGS. 19A, B, after advancing a distance beyond the introducer catheter.

An ideal thermographic imaging catheter provides high thermal and spatial resolution, yielding an image similar to that of an angioscope. The image is acquired without computer reconstruction. The operation of the catheter is safe, so that arterial flow would only have to be occluded for less than a second to obtain a snapshot. Real time heat imaging is also important for studying the temporal stability of temperature heterogeneity, to answer the question "Do hot spots in a vessel come and go over seconds or minutes?", for example. Other features of this imaging system include nearly instantaneous speed of acquisition (a fraction of a second) and very high spatial (0.2 mm) and thermal (0.01° C.) resolution. The conventional 100 μm diameter fibers currently available commercially limit the spatial resolution of prototype infrared bundles to 1/10 that of angioscopes and other endoscopes made of 10 μm glass fibers. The preferred catheters of the present invention will employ specially prepared 25 μm infrared fibers, permitting the construction of flexible, very small outer diameter (i.e., 1 to 6 mm OD), steerable, thermal imaging and heat-delivering catheters using a variety of infrared imaging fibers, encased in non-toxic polyurethane and/or polyethylene or other materials in current FDA-approved catheters. Since the commercially available IR optical fibers are made of non-biocompatible materials, the internal fluids and tissues of the body must be shielded from contact with the fibers. It is preferred that a catheter for use in detecting temperature heterogeneity in a vessel has a flushing capability and a lumen for passage of a wire guide. Also, it would be desirable in some applications to include a pressure measurement capability. The preferred designs are equipped with a balloon to occlude blood flow. As illustrated in FIGS. 19A-C, one catheter assembly employs an occluding balloon on the guiding catheter, or on a transitional catheter. Other catheter assemblies employ an occluding balloon on the distal end of the imaging catheter. (FIGS. 20B-C).

As an alternative to using the IR imaging bundles described above, a microbalometer similar to that manufactured by Raytheon (Dallas, Tex.) is placed at the end of the catheter to remotely sense infrared radiation emitted from the vessel wall. The microbalometer employs an integrated circuit, so different temperatures and different positions on the vessel wall do not each require an individual wire or fiber passing through the catheter. Rather, the information is encoded in the electronic chip. A single wire is used to transfer the thermal data through the catheter to the signal processor and display system. This type of detector does not require a cooling system and can be made compactly enough to fit onto a smaller diameter catheter tip. An occluding balloon is used to block the flow of blood for temperature sensing. The microbalometer catheter may present a smaller diameter than is possible with an IR fiber bundle catheter. Another advantage of thermosensing by microbalometer is that no physical contact with the vessel wall is necessary, which decreases the likelihood of precipitating thrombosis during thermosenising. By using one or more microbalometers, the catheter may also be used to deliver heat, and can be used for active or passive spectroscopy in the infrared or near-infrared range, thereby conveying even more information about the vessel than just heat measurements.

Each catheter of the invention is designed so that it can be used with a motorized pullback system, and with computer aided reconstruction. The above-described catheter designs lend themselves to economical mass production of accurate aid nontoxic thermography catheters for single use. In the alternative, at least some of the above-described thermography catheters can be constructed from sterilizable materials such that it can be reused.

Use of an IR Thermography Catheter Assembly to Detect At-Risk Plaque

As shown in the block diagram in FIG. 15. the user employs user interface 100, microcontroller 80 and display system 70, in cooperation with the catheter assembly 10, IR array dector 50 and signal processor 60 (some of which may be a suitably programmed computer, keyboard and video monitor) to test for temperature heterogeneity along the vessel wall. FIGS. 18 and 19A-C depict the distal portion of one embodiment of catheter assembly 10 in operative position within a vessel. First, the guiding catheter or introducer catheter 20 is inserted into a vessel, such as a coronary artery of a patient suffering from atherosclerosis and having a number of vascular lesions or plaques, as in conventional angioplasty procedures. With balloon 26 in the deflated configuration, the distal end 28 of introducer 20 is positioned at the desired location in the vessel. Positioning of the introducer in the vessel is monitored by real time fluoroscopy. Preferably the introducer is moved to within about 5 cm of the section of vessel for which thermographic examination is desired (the "region of interest"). A region of interest may be a section of normal vessel wall or it may contain abnormal tissue such as atherosclerotic plaque, or an area where the epithelial cells have been damaged or eroded. The distal tip 41 of catheter 40 is then introduced into the lumen 25 of introducer 20 (FIG. 19A) and urged beyond distal end 28 of introducer 20 and into the vessel (FIGS. 19B and 19C). Preferably the outer diameter of catheter 40 closely approximates the inner diameter of introducer 20 so that catheter 40 is able to slide along the introducer lumen but at the same time is guided and supported by the close proximity of the interior wall of introducer 20. A conventional guidewire (not shown) is used to facilitate movement of the catheter into the introducer and along the vessel lumen.

Balloon 16 is inflated briefly to occlude the flow of blood in the vessel, and catheter 40 is quickly advanced the desired distance in the vessel and then quickly retracted, whereupon the balloon 16 is deflated and circulation through the vessel is allowed to resume. At points in the vessel beyond the distal end of introducer 20, the window 48 firmly touches the vessel wall. While catheter 40 is advancing and/or retracting, infrared radiation emitted from the vessel wall is transmitted through window 48, directed by reflective surface 46 into coherent optical fibers 44. Window 48 is made of either an IR transmitting or an IR absorptive/retransmitting material. The discrete optical signals emerging from the optical fibers 44, when received by IR array detector 50, which may be a high sensitivity Indium Antimonide (InSb) infrared focal plane array (FPA) detector, are converted into corresponding electronic signals from which the in situ thermal graphic image is obtained and reported by means of a signal processor 60 and visual display 70. Under proper calibration, the digitized thermal image of the living vessel wall of a human patient monitored by the IR optics fibers is reported as a temperature map on the remote visual display.

Figure 21:
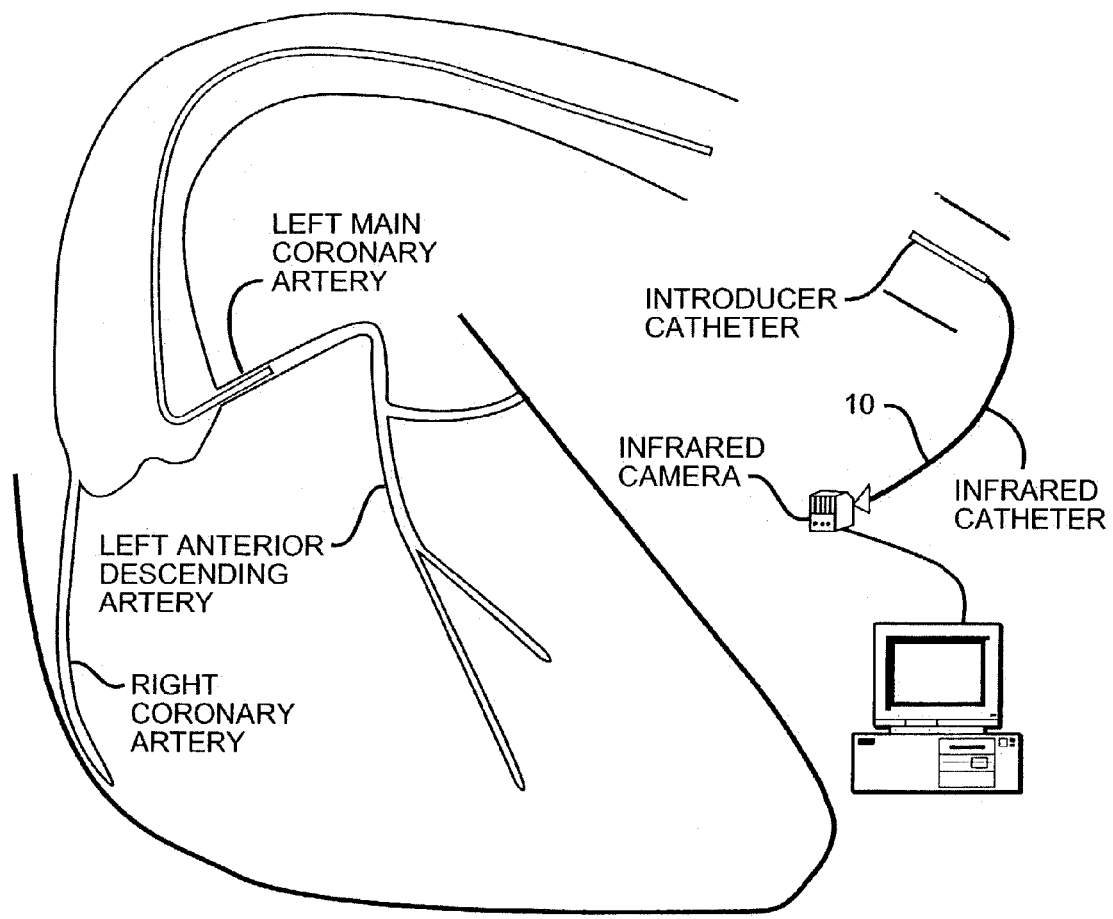
FIG. 21 is a schematic illustration of the placement of one embodiment of the infrared catheter and the introducer catheter of FIGS. 19A-C for performing a coronary thermography procedure.

In some procedures, such as coronary thermography (schematically illustrated in FIG. 21), the distance catheter 40 is advanced and the length of vessel explored is up to about 5 cm. The elapsed time from inflation of balloon 16, including the necessary amount of time for conducting the thermographic exploration of the vessel, until deflation and resumption of blood flow in the artery is about 20 seconds or less. For other situations, the necessary occlusion time and distance explored may be different, and can be readily determined by the interventionist.

One important purpose of balloon 16 is to exclude blood, saline, and other water containing or IR-absorbing substances from the area between window 48 and the heat-emitting vessel wall site or tissue 150 while temperature measurements are being taken. The dimensions of balloon 16, when inflated, are such that inflation causes sealing or closure of the vessel to the flow of blood. To facilitate removal of blood and other interfering substances such as residual erythrocytes or white blood cells that are typically left clinging to the vessel wall during conventional balloon angioplasty procedures which may otherwise become sequestered between window 48 and tissue 150, the guidewire may be removed and the guidewire lumen 42 used for perfusing with isotonic saline or another suitable washing fluid prior to advancing the catheter to the region of interest. In this way the region of interest can be washed ahead of the endoluminal surface. Because of the presence of heat producing inflammatory cells in a vulnerable plaque region, its temperature is higher than that of adjacent vessel regions queried by the IR catheter assembly. The greater the population of active inflammatory cells in the region, the greater the amount of heat, particularly at sites where the plaque cap is very thin. A temperature elevation above ambient or average vessel wall temperature or above that of the preceding site is detected by the IR thermography assembly 10 and reported to the user. Likewise, a region of lower temperature, for example where there is thrombus or fresh erosion of the luminal surface prior to the occurrence of inflammation, the thermography assembly will also be detected and reported. The temperature of each sequential site along the vessel wall is reported, stored and analyzed by the signal processor 60.

Upon completion of the infrared examination of the vessel wall, balloon 16 is deflated, allowing reestablishment of natural blood flow within the vessel, and permitting facile movement of catheter introducer 20 and catheter 40 in the vessel to a next region of interest along the luminal wall, if appropriate. Otherwise, the catheter assembly 10 is removed from the patient. The catheters illustrated in FIGS. 20B and 20C, in which the occluding balloon is located on the distal end of the imaging catheter, are used to assess temperature heterogeneity or thermally map a vessel in a manner similar to that described above.

In some situations, while exploring a vessel to identify dangerous plaque with the IR catheter assembly, it is desirable at the same time to treat a "hot" plaque by applying low-level heating, for example in the range of 38°-44° C. A preferred mode of treatment is to heat the elevated temperature region for at least 15 minutes at about 42° C. (as disclosed in U.S. Pat. No. 5,906,636, the disclosure of which is incorporated herein for all purposes). A suitably programmed microprocessor is in this case employed to average the "hot score" (i.e., skewness of temperature) or heterogeneity score (variance of temperature) of a plaque and then automatically turn on the IR heater to dispense a predetermined amount of heat to the plaque. One potential problem with applying heat treatment in conjunction with further wall temperature measurements is that heating could change the thermal pattern of other plaques yet to be measured further along the artery wall downstream from the treatment site. One way to avoid this problem is to make the temperature assessment during the advancing phase, whereby the vulnerable plaque target sites are identified, and then administering the heat treatment to the targets during the catheter retraction phase. In order to accomplish this, the signal processor 60 memorizes the distance from a defined starting point in the vessel ("point zero") from which the catheter travels down the vessel. Thus, for each specific site along the vessel wall the suitably programmed software would assess at least two bits of information, including temperature and the X-Y coordinates for anatomical position. Using the X-Y coordinates, a target site can be located quickly for subsequent application of heat, after all of the target sites have been identified and the need for treatment has been ascertained. The need for treatment is evaluated by additional software programming and as the software-guided catheter reverses its path in the vessel during retraction, a calculated amount of heat is applied to the targeted sites. All of this can be accomplished within the brief time interval during which the vessel is occluded.

Instead of or in addition to heat treatment, other forms of treatment suitable for use in conjunction with the above-described method of detecting at-risk plaque include local treatment of a target site with a pharmaceutical agent applied through the guidewire/flushing lumen. Suitable agents include anti-inflammatory agents such as steroids, leukotriene inhibitors, prostacyclin adenosine, NO, inhibitors of cyclo-oxygenase I and II, and of PGH synthase, TGFβ, antibodies to TNFα ILI, interferon γ N, agents that stimulate smooth muscle cells to proliferate and secrete collagen, such as PaGFs (platelet-derived growth factors) and TGFβ.

Alternatively, another more conventional treatment may be indicated after vulnerable plaque is identified by this method. Some of these treatments include balloon angioplasty, atherectomy (shaving or cutting the plaque), and laser angioplasty. Treatment options that can be employed after identifying a vulnerable plaque by the methods described herein are discussed above in the section subtitled "Therapeutic Implications."

As alternatives to the IR imaging bundle catheter systems described above, other suitable catheter-based heat detection systems employ thermocouples or thermistors, near-infrared, ultrasound, magnetic resonance microwave, or liquid crystals, as long as they meet the minimum temperature resolution and the physical and operational requirements described above with respect to the infrared catheters.

Thermocouple Basket Catheter

Other exemplary heat detecting devices are shown in FIGS. 23A-E, 24A-B, 25A-C and 26A-C. FIG. 23A depicts a high-speed multi-channel thermocouple catheter 210 with four channels 220 for contacting the vessel wall and simultaneously localizing heat at four circumferential spaced-apart points at each longitudinal position along the vessel wall. In FIG. 23A, only the two channels in the foreground are shown. Catheter 210 works in cooperation with a detector, signal processor and display system to analyze and report the temperature sensed at each point examined. Channels 220 together form an expandable/retractable thermocouple "basket" 230 (shown in the expanded configuration in FIG. 23A). The maximum outer diameter of each channel 220 is about 0.01 inch, and preferably about 0.007-0.008 inch (0.018-0.02 cm) At about the maximum diameter point 234 of basket 230, each channel 220 is configured as shown in the cross-sectional segment depicted in FIG. 23C. At this point, channel 220 has a thermally conductive outer layer 222 which is substantially cylindrical in shape, and an interior space 224. Interior space 224 contains a cold thermocouple junction 260 in contact with the vessel wall-contacting or outward-facing side 226 of outer layer 222. As shown in FIG. 23D, between junction 260 and inward facing side 228 is insulating material 240, which substantially fills the remainder of interior space 224. On the proximal side 236 of basket 230 each channel 220 is configured as shown in FIG. 23C. Within space 224 thermal insulating material 240 surrounds or embeds insulated thermocouple wires 270a, 270b. Encasing wires 270a, 270b is an electrically insulating material 272 such as polyurethane. The maximum outer diameter of insulated wires 270a, 270b is about 0.003-0.005 inch (0.0076-0.0127 cm). Suitable insulated thermocouple wires and cold thermocouple junction assemblies for use in this embodiment are available from well-known commercial sources. On the distal side 238 of basket 230 each channel 220 is configured as shown in FIG. 23E. Space 224 is preferably filled with insulating material 240, which may be air or another material that has low thermal conductivity. At the distal end or tip 232 of basket 230 each of the channels 220 terminate. If desired, insulating material 240 may be omitted from distal section 238 to tip 232. Tip 232 is a soft, preferably rounded covering over the distal terminus 221 (not shown) of each channel 220. The insulation extends distally a sufficient length to ensure adequate protection of the thermocouple junction 260 from any temperature effects of fluids flowing through the vessel. By locating the junction in each channel close to the source of heat (i.e., the vessel wall) and away from sources of artifactual heating or cooling (i.e., fluids flowing through the vessel lumen and through the basket interior), the measured temperature primarily reflects the temperature of the plaque or vessel wall.

Figure 24A:
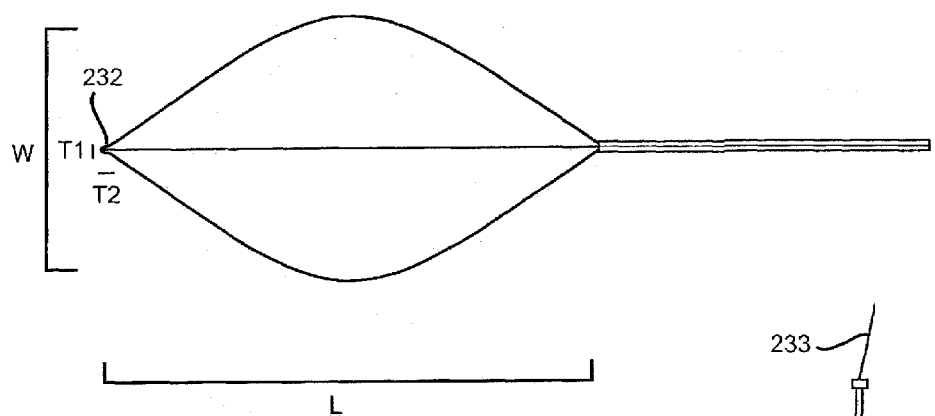
FIG. 24 A is a schematic illustration of a basket catheter similar to that shown of FIG. 23A.
FIG. 24B illustrates the basket catheter of FIG. 24A emerging out of a guiding or introducer catheter.
Figure 24B:

The dimensions of basket 230 are schematically shown in FIG. 24A. The length of the basket (L) is preferably about 1.5-2 cm. The maximum width of the fully expanded basket is preferably about 0.8×L. The width of tip 232 (T1) is dictated by the number and volume of channels and whether they are fixed or slidable inside the tip. Four to 32 channels are preferred. For many applications in which the thermosensor catheter will be used, the termini 221 are fixed securely inside soft tip 232. For some applications, particularly for exploring either eccentric or concentric lesions, it is preferable for the channel ends 221 to have the freedom to move forward and backward in tip 232, as shown in FIGS. 24B-C. In this case, tip 232 is anchored by attachment to two or more channel termini 221 (FIG. 24B). Alternatively, an anchor wire 233 running through the center of the basket attaches to the closed end 235 of tip 232 (FIG. 24C). The length of tip 232 (T2) is preferably sufficient to allow channel ends 221 to travel as much as 5 mm.

At the proximal end 231 of basket 230, channels 220 merge into a hollow shaft 280, the interior 284 being large enough in diameter to accommodate all of the insulated thermocouple wires 270a, 270b. Shaft 280 fits inside a standard guiding catheter (as shown in FIG. 24B). A cross-section of shaft 280 is shown in FIG. 23B. Insulated wires 270a, 270b are preferably embedded together in an insulating material or glue 282. Insulated wires 270a, 270b are routed through the shaft interior 284 to the proximal end of thermocouple catheter 210, and then electrically connected outside the body to a temperature display unit (shown in FIGS. 27A and 27B).

Figure 25A:
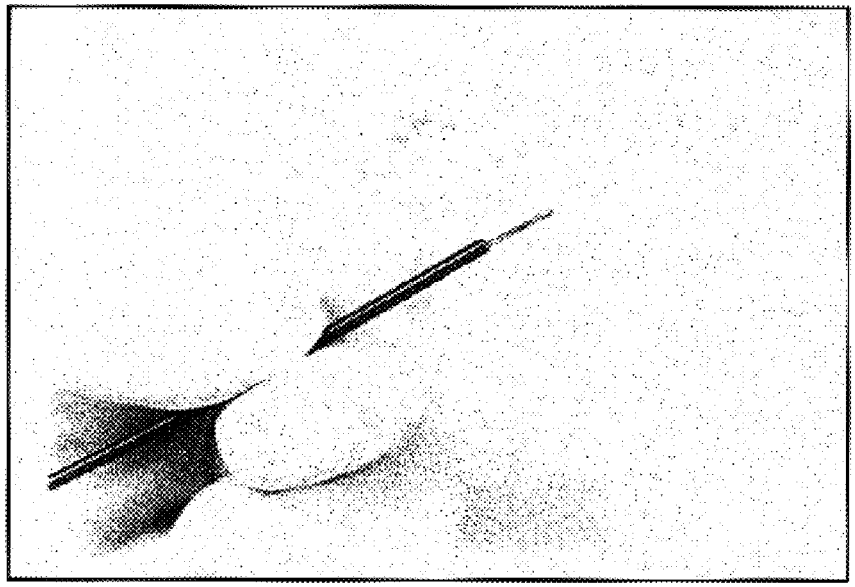
FIG. 25A is a close up photograph of a thermocouple basket catheter of the invention, with the basket emerging from the tip of the guiding catheter.
Figure 25B:
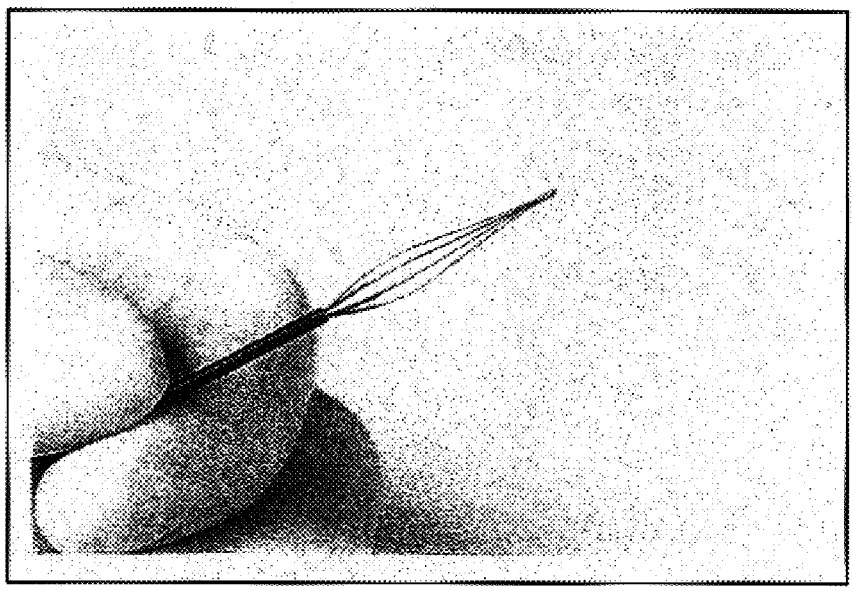
FIG. 25B is another view of the catheter of FIG. 25A with the basket beginning deployment.
Figure 25C:
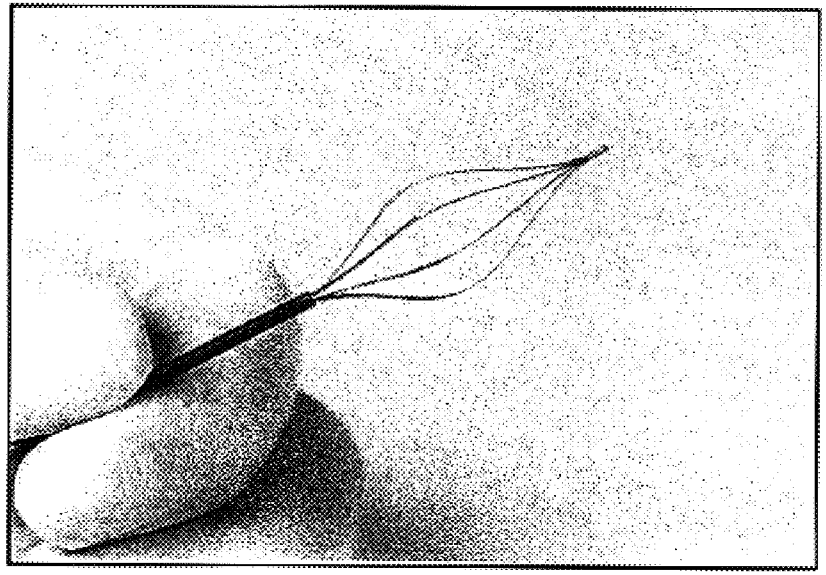
FIG. 25C is another view of the catheter of FIG. 25A with the basket nearly fully deployed.
Figure 25D:
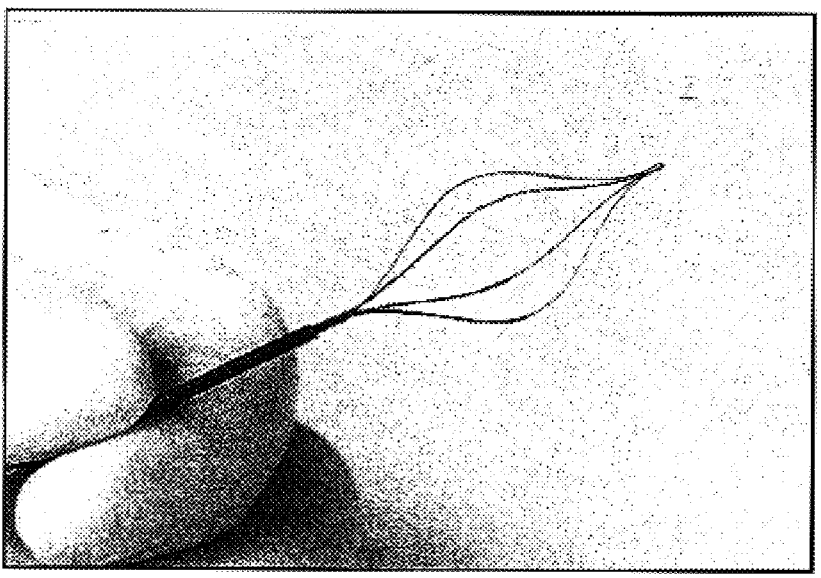
FIG. 25D is another view of the catheter of FIG. 25A with the basket fully opened.

When employed for measuring the temperature at sites along a vessel wall, basket 230 is initially compressed into a column which can be fitted through a guiding or introducing catheter 220 similar to those used in conventional cardiovascular procedures and which range in outer diameter from about 1 to 6 mm, shown in FIG. 25A. After placement of guiding catheter 250 within a vessel adjacent a region of interest along the luminal wall, basket 230 is inserted and conduit 280 is urged distally such that basket 230 emerges at guiding catheter distal end 252, whereupon basket 230 gradually springs open and assumes its "basket" configuration as it emerges (FIGS. 25B-D). Preferably the whole body of the catheter, i.e., basket 230 and shaft 280, is made of a shape memory metal such as NITINOL™. When at least the outer layer 222 of channel 220 is a shape memory metal such as NITINOL, the channels together will define, at least in part, the final shape of basket 230. The metal transition zones are apparent in FIGS. 25A-D. In its fully deployed configuration, basket 230 is a tapered ovoid, or it may be another suitable shape that facilitates the ability of the temperature sensors or junctions 260 within channels 220 to make thermal contact with the lumen surface. In any case, basket 230 substantially conforms to the shape of the vessel lumen as it comes out of the narrow catheter 250, so that channels 220 at maximum diameter point 226 contact circumferentially spaced-apart sites of the vessel wall, which may or may not include a region of vascular lesion. The outer layer 222 of channel 220 is made of thermally conductive material, preferably a memory metal or another material that possesses similar properties. If desired, an expandable balloon may be included on a central inflation lumen (not shown) for deploying inside the basket to momentarily restrict or occlude the flow of blood in the area during temperature measurements. With the inflatable balloon the temperature of the vessel wall downstream can be measured with and without blood flow. The balloon may also assist in biasing the channels 220 firmly into contact with the vessel wall.

Figure 26A:
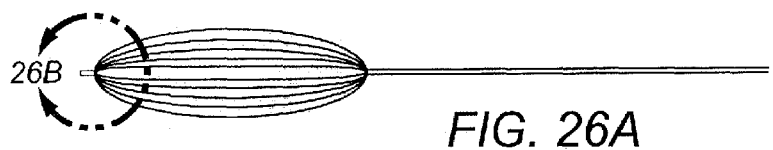
FIG. 26A illustrates another multi-channel thermosensor catheter of the invention showing the tip enclosing the channel ends.
Figures 26B, 26C:
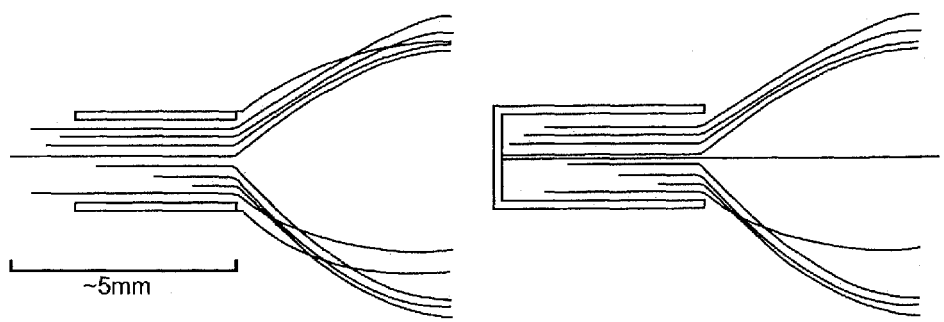
FIG. 26B shows an enlarged view of one embodiment of the tip of FIG. 26A and variable positioning of the channels for optimal contacting of eccentric lesions.
FIG. 26C is an alternative embodiment of the basket catheter shown in FIG. 26B, with a centrally located tip anchoring wire.

If simultaneous or coordinated measurement of several circumferential sites is desired, a multi-channel basket thermosensor catheter such as that shown in FIG. 26A is employed. The number of additional channels is limited only by the maximum diameter constraints of the vessel and the volume of the channel materials needed. Four to 32 channels is preferred. Fewer channels may also be used if a very small diameter thermocouple catheter is needed and the number of circumferental sites to be simultaneously measured can be reduced, or if the catheter can be rotated in situ so as to circumferentially explore each longitudinal region along the vessel wall. It can be readily appreciated in FIGS. 26A-C that when each of a number of channels is able to self-align within tip 232, the surfaces of both smooth and irregularly shaped lesions can be firmly contacted by a channel. The flexibility allows the catheter to have enough bend radius to perform coronary studies, and to mold gently against irregular surfaces. Accordingly, the maximum deployment achieved by each channel 220 may vary when tip 232 is configured so as to permit movement of the free channel ends 221 so that the basket shape better conforms to the shape of the lesion.

Figure 27A:
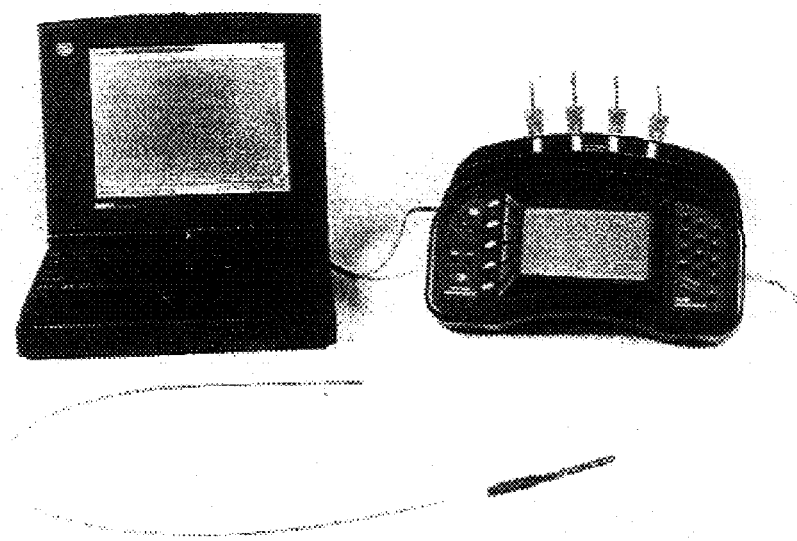
FIG. 27A is a photograph of one vascular temperature measuring assembly of the invention.
Figure 27B:
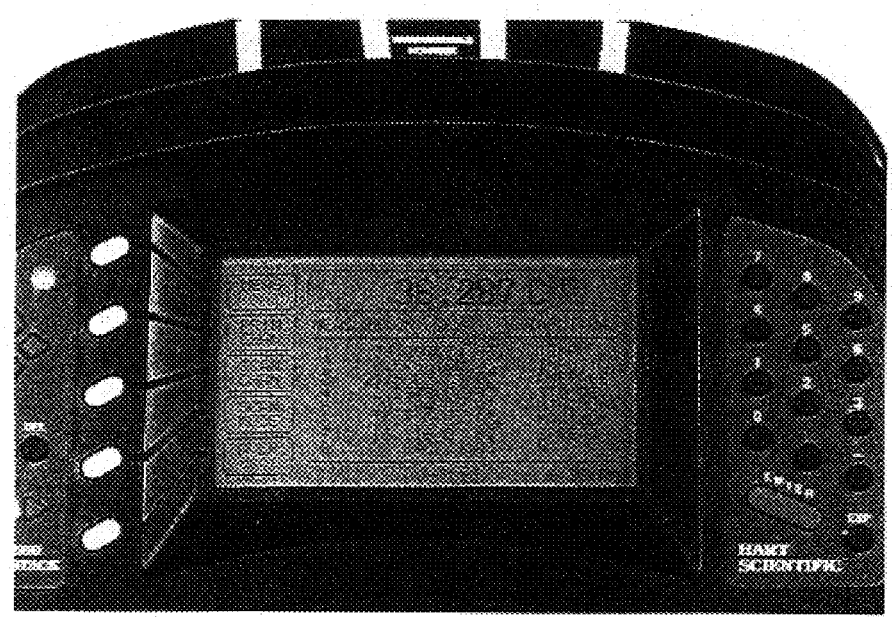
FIG. 27B is a close up view of the display screen of the assembly shown in FIG. 27A.

Thermocouple catheter 210 is used to measure the temperature inside a cavity or vessel and to provide, indirectly, a visual image of those temperatures when the catheter is electrically connected to a temperature display device, as illustrated in FIGS. 27A-B. An "ultrathermometer", such as that manufactured by Hart Scientific receives the signal from the thermocouple and measures the temperature. A dedicated microprocessor, such as a PC or laptop computer, receives the data from the thermometer and enters it into a suitable database with thermographic color images. The thermal sensitivity is 0.001° C. with activation time 0.35 sec., range 0-90° C.

Figure 28A:
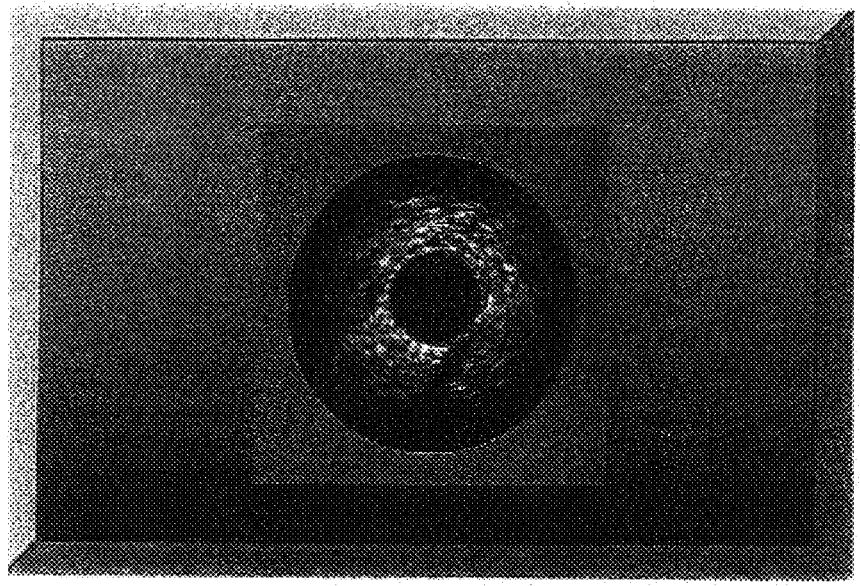
FIG. 28A is an intravascular ultrasound image of a coronary artery.
Figure 28B:
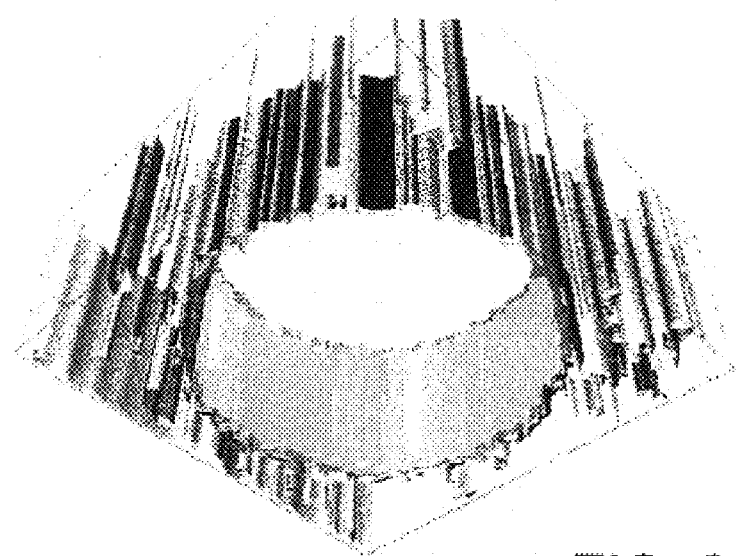
FIG. 28B is a schematic illustration of the IVUS image of FIG. 28A fused with a thermal image of the same region of artery.
Figure 28C:
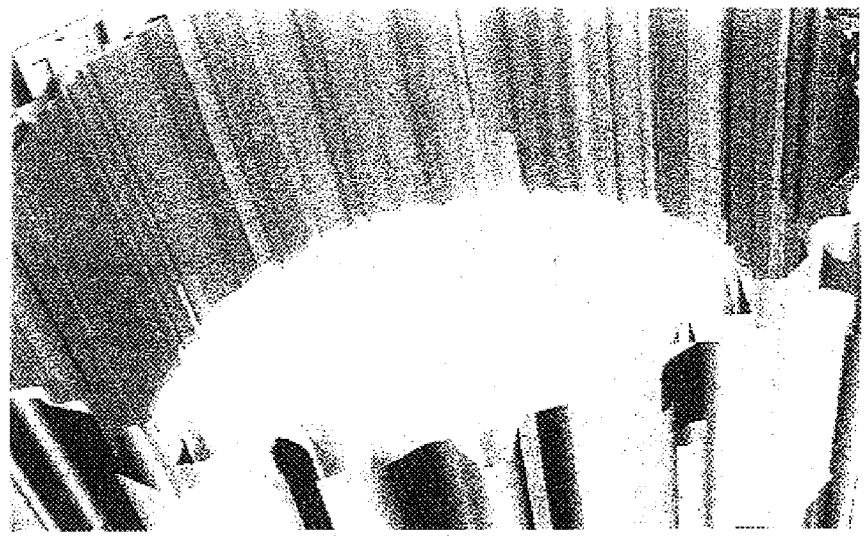
FIG. 28C is a schematic illustration of a fused ultrasound/thermal image simulating a three dimensional arterial view.

Alternatively, an ultrasound transducer/receiver is also included to increase the diagnostic power of the catheter. A conventional intravenous ultrasound (IVUS) wire that is small and flexible (such as an intravascular ultrasound catheter manufactured by EndoSonics Corporation, Rancho Cordova, Calif.) can be readily incorporated into the above-described basket catheter. Preferably the wire extends through the center of the basket and the ultrasound transducer is located on the distal end of the basket adjacent tip 232. An intravascular ultrasound image of a coronary artery is shown in FIG. 28A. When this image is combined with a thermal image of the same section of artery, a 3-dimensional image such as that illustrated in FIG. 28B results. FIG. 28C is another schematic illustration of a fused ultrasound/thenral image simulating a 3-D intra-arterial view. Three-dimensional reconstruction of sections of a vessel and image fusion (i.e., combining thermal mapping with ultrasound, angiography and angioscopy images) will further enhance the usefulness of the thermosensing catheters.

A thermocouple basket is also capable of delivering heat to specific regions of the vessel, if coupled with a heat source, such as a RF generator. The basket may be used to monitor temperature during heat therapy as well, if the catheter is equipped with a separate heat delivery system. Although spatial and thermal resolution obtained with a thermocouple catheter may not be quite as good or as rapid as that of an infrared catheter system, this type of thermocouple catheter does not pose the disadvantages of image degradation, cost and limited flexibility that may impede IR fiberoptic imaging. This catheter is well suited for intra-aortic as well as intracoronary measurement of temperature. Additional improvements may include a motorized Piezo-electric tracking system.

Thermistor Basket Catheter

Another alternative device for detecting temperature differences in a vessel is a thermistor basket catheter having a similar external appearance to the thermocouple catheter described above and shown in FIGS. 25A-D. A thermistor catheter is constructed by substituting externally mounted resistance temperature devices (RTDs or thermistors) for the thermocouples. In this case, the thermistors are also positioned at the maximum diameter positions on each channel and oriented so as to contact the vessel wall when the basket is in the expanded configuration. This thermistor basket catheter is used substantially the same was as described above for the thermocouple basket catheter. It also lends itself to use in a dual-function mode for determining the temperature at specific points inside the vessel and then, in cooperation with a suitably programmed microprocessor, automatically heating the target tissue to a predetermined temperature, as taught in U.S. Pat. No. 5,906,636, for gently heating at-risk lesions to reduce the level of inflammation. In making a dual function heat detection/heat treatment thermistor catheter, two RTDs are employed, one for measuring temperature and the other for heating. The temperature measuring accuracy of this thermistor basket exceeds 0.01° C. over a temperature range of 0-50° C., with a response time of about 0.3 second. The heating power is adjustable from 0 to 3 Watts. To measure and control the temperature the catheter must closely contact the vessel wall, allowing no blood flow between the RTD and the vessel wall. For prolonged use in a vessel, an insulated perfusion channel is included to allow continuous blood flow while the outer surface of the catheter tip contacts the vessel wall for the necessary period of time. The introduction of electrified catheters into the body is less preferred due to the potential danger to the patient.

As an alternative, thermosensors such as thermocouples or thermistors may be mounted on the surface, or embedded in the wall of, an inflatable balloon on a catheter that is similar to a conventional angioplasty catheter.

Another alternative thermosensing catheter assembly utilizes a thermocouple or thermistor at the distal end of the catheter, and another mounted at the distal end of the guide wire. If, when the guide wire is advanced down the vessel, it records a higher temperature than the more proximal sensor on the catheter, such temperature difference is useful in identifying the presence of diffuse inflammatory lesions. If confluent, such lesions might be identical in temperature, so that their increased temperature could not be detected by a catheter that measured temperatures at nearby loci (e.g., 0.1 cm apart) relative to each other. This type of false negative could be avoided using this device. This catheter also facilitates monitoring therapy by infusion of hot saline or by heating blood. Low level heat treatment of this type is one of several methods of thermal therapy developed and patented by the present inventors for prevention of plaque rupture or restenosis by induction of apoptosis in macrophages.

Near-Infrared Imaging Catheter

Still another catheter-based alternative to the IR fiber optic bundle catheter described above is a near-infrared (NIP) imaging catheter. It has been Long known that in the near-infrared range (NIR, 800 to 2500 nm) water exhibits a significant absorption of the electromagnetic radiation, and that NIR absorption of water significantly varies with temperature. Since tissue is mainly water, spectroscopy can be used to measure the tissue temperature to within 1-2° C., though in water or homogenious tissue thermal resolution of 0.2° C. has been reported by others (Kelly et al. *SPIE* 2389: 818-828 (1995)). Since near-IR spectroscopic imaging is a relatively new field, it has not been employed in catheter-based devices. Although NIR spectroscopy is less accurate than some other methods in terms of thermal resolution, its use has certain advantages. One advantage of the NIR spectroscopic approach is that the equipment is available commercially and relatively inexpensive. Another advantage is that there are additional ways that NIR spectroscopy can be helpful in identifying vulnerable plaque. For example, in related U.S. patent application Ser. No. 09/188,661 the inventors have recently identified marked variability in plaque pH, and the literature has amply documented the plaques high content of NO and reactive oxygen species, as well as its low partial pressure of oxygen. These chemical variables are relevant because each creates changes in the NIR spectrum of plaque. It is quite likely that together these features create a characteristic NIR spectrum for plaque vulnerability, and it is possible that such a spectrum would be even more predictive of imminent plaque rupture than thermography alone.

Intravascular Ultrasound Catheter

Another alternative catheter-based device that could be used instead of, or preferably in combination with, the IR fiber bundle catheter to detect vulnerable plaque is an ultrasound catheter. A heat detection ultrasound catheter takes advantage of the fact that ultrasound, being a mechanical wave propagated through tissue, is influenced by temperature. Two methods, "time of flight velocimetry" and "tissue discrete scattering," have been used in different applications by others to estimate tissue temperature during therapeutic hyperthermia (Seip et al., *IEEE Trans Biomed Eng* 42:828-39 (1995); Maass-Moreno et al. *J Acoust Soc Am* 100:2514-21 (1996)).

Liquid Crystal- or Temperature Sensitive Fluorphore-Coated Balloon

Another balloon catheter-based mode of detecting heat along a vessel wall utilizes liquid crystals or temperature-sensitive fluorphores coating the balloon of the catheter. Thermographic cholesterol-based liquid crystals are readily available commercially. In preliminary experiments, a catheter balloon coated with encapsulated liquid crystals demonstrated a visible color image with significant thermal and spatial resolution, as shown in FIG. 23E. In this test, a liquid crystal sheet was placed on the heated phantom described above with respect to the IR fiber bundle. The color images visible in FIG. 23E are the ends of the brass (26.8° C.) and lead (26.5° C.) rods heated from the same base heater at 28.7° C. One disadvantage of liquid crystal thermography is that spatial resolution changes rapidly as thermal energy spreads over the crystal. Also, the coated balloon requires visual monitoring from inside with an angioscope. An alternative to using liquid crystals is to internally coat a balloon with a temperature-sensitive fluorescent probe. Temperature-sensitive fluorescent dyes are also commercially available. The sensitivity of one of these has recently been described by Zohar et al. (*Biophys J* 74:82-9 (1998)). Using the temperature-dependent phosphorescence intenisity of the rare earth chelate. Eu TTA (europhium III thenoyltrifluoro-acetonate), subcellular (e.g., 1 micron) resolution, with thermal resolution was achieved, sufficient to see changes on stimulation of the cells' muscarinic receptors (Chapman et al. *Photochem Photobiol* 62:416-25 (1995)).

Intravascular Magnetic Resonance Imaging

Magnetic resonance imaging (MRI) has recently attracted attention as a non-invasive technique for studying atherosclerosis, and initial studies by others describe using magnetic resonance chemical shift imaging and spectroscopy of atherosclerotic plaque (See Mohiaddin *Br Heart J* 62:81-9 (1989); Vinitski et al. *Ivest Radiol* 26:703-14 (1991); and Trouard et al. *Magn Reson Med* 38:19-26 (1997)). However, because atherosclerotic vessels such as the aorta, coronary arteries, and renal arteries are located deep in the body, surface coils do not produce optimal images of vascular lesions. A small receiver coil placed inside a vessel near the vessel wall has superior signal/noise and spatial resolution. A few catheter MR receiver coil designs have been proposed by others for imaging the walls of large blood vessels such as the aorta (Zimmermnann et al. *Radiology* 204:769-74 (1997); Atalar et al. *Magn Reson Med* 36:596-605 (1996); Martin et al. *J Magn Reson Imaging* 2:421-9 (1992)). None of these devices has been used for measuring temperature differences in the vessel wall, however.

MRI is sensitive to temperature and the inventors propose employing intravascular magnetic resonance thermometry (MRT) similar to the procedures described by Matsumotu et al. *J Magn Reson Imaging* 4:65-70 (1994); Dickenson et al. *J Comput Assist Tomog* 10:468-472 (1986); Delannoy et al. *Magn Reson Med* 19:333-339 (1991); Zhang et al. *Int J Hyperthermia* 8:263-274 (1992); and Gewiese et al. *Invest Radiol* 29:345-351 (1994), the disclosures of which are incorporated by reference, to detect vulnerable plaques in a living vessel. Others have used thermal magnetic resonance imaging in animal models to follow heat therapy for experimental tumors, but these techniques have not been applied to detection of vulnerable atherosclerotic plaque. The current thermal resolution of such devices is in the range of about 1-2° C. with spatial resolutions of 1-3 mm. Even without further improvements in resolution, conventional magnetic resonance thermometry devices can he used to detect large areas of inflammation in large vessels such as the carotid arteries and the aorta by modifying the detection and processing systems described above for the IR fiber bundle catheter. Such areas of inflammation in living vessels after being identified by MRT, will likely be proven statistically to have a high incidence of developing aneurysm and rupture.

Figure 29A:
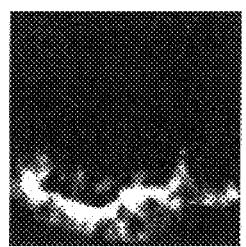
FIGS. 29A-F are magnetic resonance images of a specimen of cholesterol-fed Watanabe heritable hypercholesterolemic rabbit aorta taken at 0.3, 6, 10, 15 and 30 mins., respectively, as the specimen cooled from 42° C. to 37.4° C.
Figure 29B:
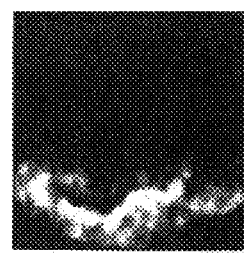
Figure 29C:
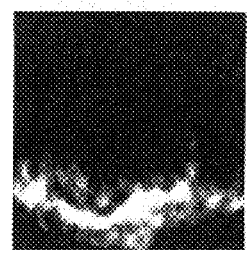
Figure 29D:
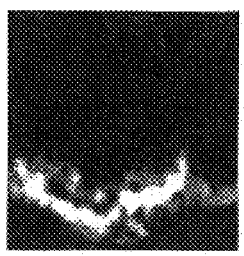
Figure 29E:
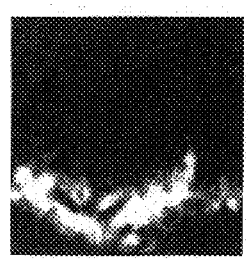
Figure 29F:
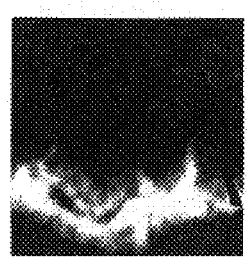
Figure 30B:
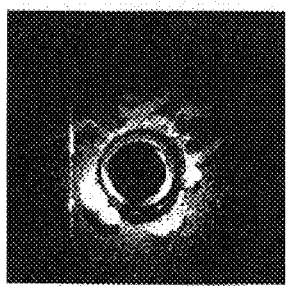
FIGS. 30B-G are in vivo IV MR images of live canine artery obtained with the catheter imaging coil of FIG. 30A.
Figure 30C:
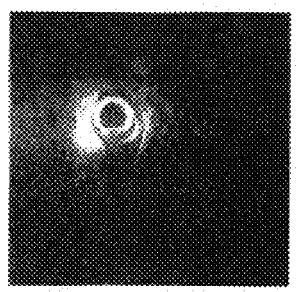
Figure 30D:
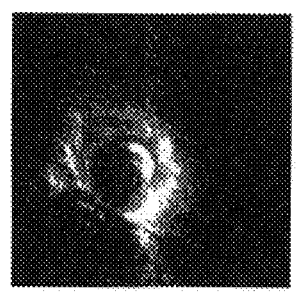
Figure 30E:
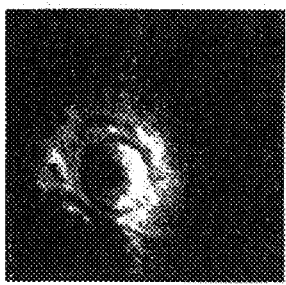
Figure 30F:
Figure 30G:
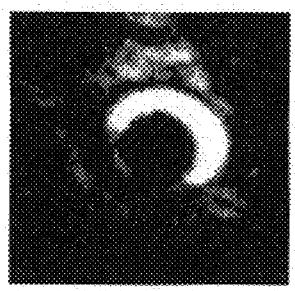

In one preliminary in vitro study, containers of water or lipid served as phantoms with varying temperatures. T-2 weighed images showed a loss of signal intensity with an increase in the temperature of the water. In the lipid phantom, signal intensity increased with temperature. A thermal resolution of approximately 0.8° C. was obtained. In a preliminary animal study, thermal MR imaging of living aortic specimens of Watanabe hypercholesterolemic rabbit was performed. After surgically exposing, the aorta was placed in a test tube containing Dulbeco's Modified Eale Medium (DMEM) and heated in a water bath at 42° C. for 15 mins. Using a small bore external coil, MRI pictures shown in FIGS. 29A-F were taken immediately after removal from the water bath (FIG. 29A) and at 3, 6, 10, 15 and 30 mins. after heating (FIGS. 29B-F, respectively), while the specimens gradually cooled to 37.4° C. The sensitivity of thermal sequences to temperature changes can be appreciated in FIGS. 29A-C, where the margins of the aorta are not as well demarcated (as shown by the arrow) as they are in FIGS. 29D-F.

Figure 30A:
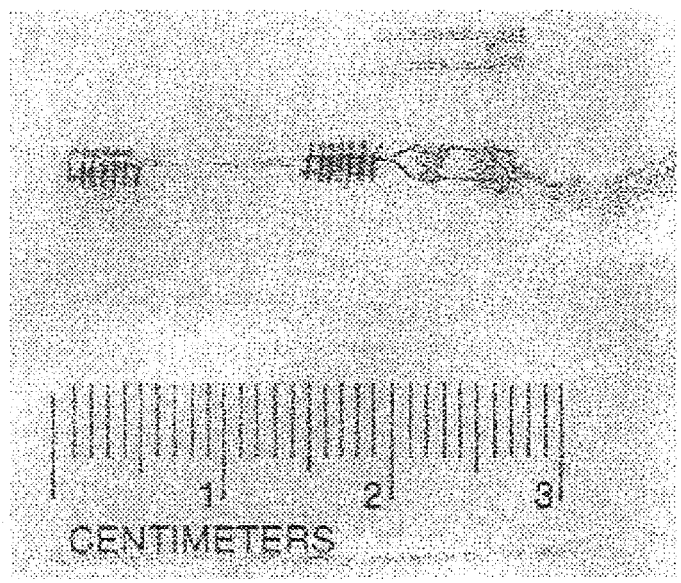
FIG. 30A is a photomicrograph of an intravascular magnetic resonance receiver (IV MR) catheter imaging coil of one embodiment of the invention.

An IV MR thermometry catheter such as that described by Hurst et al. (*Magn Reson Med* 24:343-57 (1992), is expected to provide a satisfactory substitute for the IR catheter described above. FIG. 30A shows the intravascular magnetic resonance receiver catheter imaging coil used in the inventors' preliminary studies. With this device the inventors have demonstrated thermal imaging MR sequences to detect temperature differences of about 1.0° C. in phantoms and tissue specimens. FIGS. 30B-G are exemplary in vivo MR images of live canine artery showing vessel wall architecture in a 2 cm field of view prepared by other investigators. Studies following a cohort of animals with and without extensive atherosclerosis, using periodic thermal MR to study the natural history of hot plaques will provide further indication of whether plaques with higher thermal signals are indeed those with histopathological features of vulnerability.

Predicting Vascular Restenosis After Angioplasty

Balloon angioplasty of the coronary arteries is a major advance in treatment and has been performed on hemodynamically significant coronary stenoses (those that are 70% to 99% of the cross-sectional diameter of the vessel) with a success rate of 90%. In about 40% of the patients, however, restenosis occurs in the vessel and most of the benefit gained by the procedure is lost. Restenosis is a renarrowing of an artery that has undergone one or more interventional techniques to relieve an original stenosis caused by plaque. The injury to the vessel wall caused by angioplasty or atherectomy probably causes the smooth muscle cells at that site to proliferate and to secrete an extracellular matrix which again narrows the artery. Both cell proliferation and secretion are exergonic (heat-generating) processes which should also be detectable according to the above-described procedure. Many factors have been reported to be predictive of which patients will develop restenosis. However, these studies are markedly at odds with each other and no factor has been strongly predictive of the restenosis process. Thus, cigarette smoking, hypertension, hypercholesterolemia, unstable angina, age, sex, and many other factors have been only weakly predictive, at best. Thus, in addition to the difficulty of identifying high risk plaques, another major diagnostic and prognostic dilemma for cardiologists not solved by prior art devices or methods is predicting which patients will develop restenosis. It is known that macrophage concentration in a region of vessel wall is correlated to the risk of restenosis, and some of the inventors have earlier established that active macrophages give off heat which is measurable in living vascular tissue. This heat is detectable using the devices of the present invention. The above-described IR fiber bundle imaging catheter, or one of the other heat-detection devices described herein, are will also serve as useful tools for assessing which angioplasty- or atherectomy-injured vessel wall sites are actively restenosing before significant luminal narrowing is detectable by conventional means.

These deices and methods will also be useful to those in the field to effectively identify patients who have arterial wall areas of lower rather than higher temperature, such as areas of extensive scarring, lipid pools where there is no cellular infiltration, or areas of hemorrhage and thrombosis which have yet to be colonized by inflammatory cells.

An Animal Model for Non-Invasively Following the Natural History of Hot Plaques

Figure 31A:
FIG. 31A is a color photograph of the ear of a Watanabe heritable hypercholesterolemic rabbit on a high cholesterol diet showing severe atherosclerosis extending to the arteries of the ear. The curved arrow indicates visible atherosclerotic lesions.
Figure 31B:
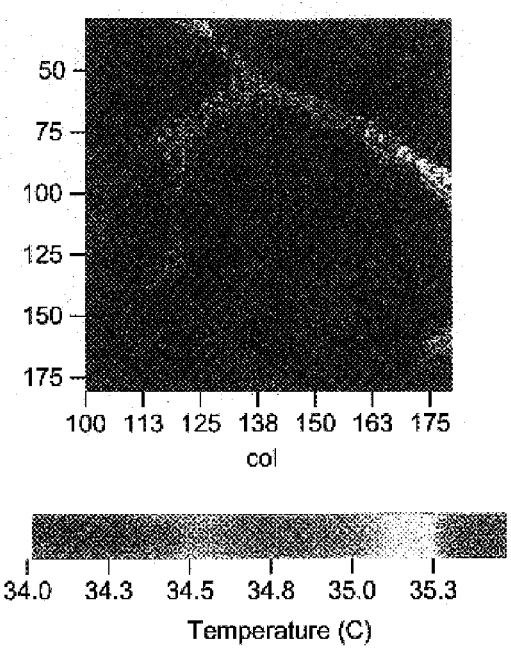
FIG. 31B is a color infrared photograph showing a close up view of the region of artery around the arrow shown in FIG. 31A. A color vs temperature key is also shown.

When Watanabe heritable hypercholesterolemic rabbits are fed a high-cholesterol diet, the resulting atherosclerosis extends as far as the central ear artery, as shown in FIG. 31A using routine visible color photography. It can be readily seen that the artery is beaded with lesions. FIG. 31B is an infrared photograph showing that the same ear artery has 1-2° C. of focal thermal heterogeneity. Also apparent is a region of low temperature. The absence of arterial branches to the low temperature region suggests ischemia due to atherosclerotic occlusion.

Figure 32A:
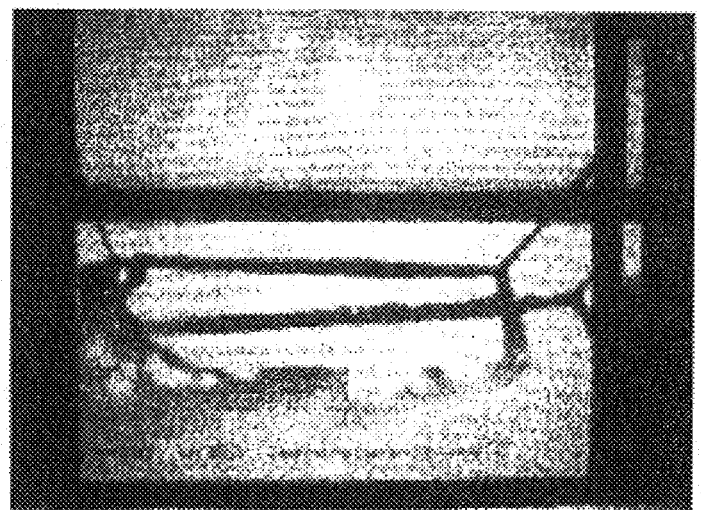
FIG. 32A is an in vivo color infrared photograph of the carotid arteries of a Watanabe rabbit like that of FIG. 31A, the hatched cross-hairs are placed to the right of three warm plaques (yellow dots) in a region 26.08° C.
Figure 32B:
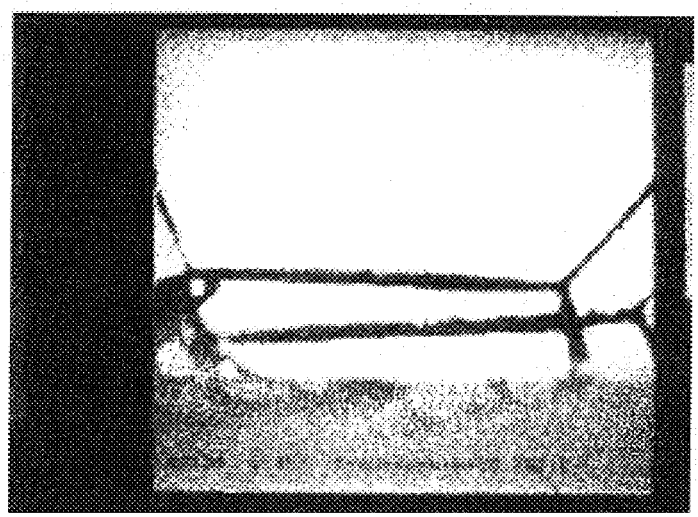
FIG. 32B is the same as FIG. 32A except that the crosshairs are over a plaque measuring 28.28° C.

FIGS. 32A,B are color infrared photographs showing that in this Watanabe rabbit thermal heterogeneity is visible from the outside using an infrared camera. The rabbit's carotid arteries were momentarily retracted upward by sutures for photography. The lower artery is in focus. FIG. 32A shows the cursor (hatched cross-hairs) to the right of the three warm plaques (yellow dots) in a region 26.08° C. FIG. 32B shows the same artery with the cursor over a plaque measuring 28.28° C. Additional studies in which the luminal surface of Watanabe heritable hypercholesterolemic rabbits exhibit thermal heterogeneity (both by thermistor and IR) which correlates with the density of underlying macrophages and inversely with their distance from the lumen are not shown. These studies are consistent with the findings in the human plaques.

The results of the inventors' present investigations demonstrate that living human and rabbit atherosclerotic plaques exhibit thermal heterogeneity on their lumen surface, and this relates well to the depth of underlying cells, most of which are macrophages. It is highly likely that lesions with inflammatory cells on the surface are dangerous because of the thrombotic tendency of these cells and the lack of antithrombotic and vasorelaxing endothelium. It is also likely that thin caps with inflammatory cells in or beneath the caps are at risk of rupture. The inventors' continuing investigations are expected to elucidate the actual frequency with which hot plaque goes on to rupture.

The cholesterol fed Watanabe heritable hypercholesterolemic rabbit model is thus one in which the natural history of warm plaques can be followed over time, preferably using externally applied infrared imaging as an indirect measure of tissue flow. The latter is correlated with electromagnetic flow meters (for arterial flow) and laser tissue Doppler measurements of regional microvascular perfusion, and eventual histology. This model is also suitable for following, non-invasively, the effects of local heat therapy or other interventions.

In Vivo Detection of Plaque Temperature Heterogeneity in an Animal Model

Figure 33E:
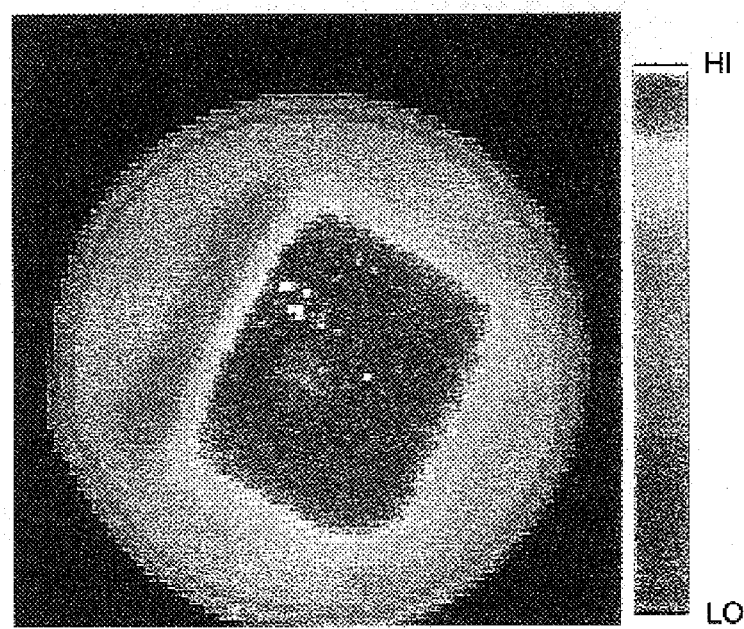
FIG. 33E shows an infrared image of a rabbit animal model.
Figure 33A:
FIG. 33A is a color photograph showing the atherosclerotic heart of a cholesterol-fed hypercholesterolemic canine model of human atherosclerosis.
Figure 33B:
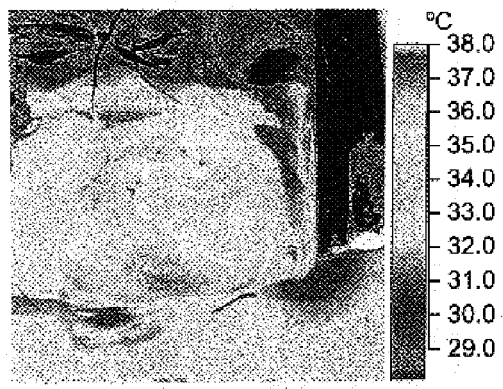
FIG. 33B is a color infrared image of the heart shown in FIG. 33A demonstrating temperature heterogeneity associated with certain atherosclerotic lesions.
Figure 33C:
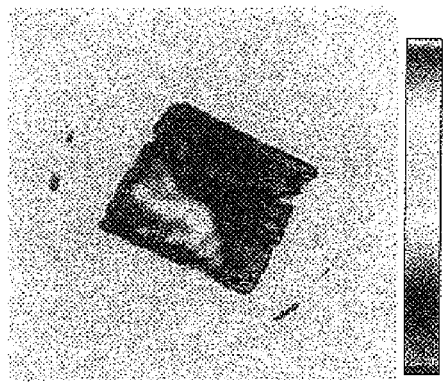
FIG. 33C is a color infrared image taken with the fiberoptic bundle employed in a catheter of the present invention showing different temperatures at the end of the bundle when the other side of the bundle is externally applied against an atherosclerotic lesion.
Figure 33D:
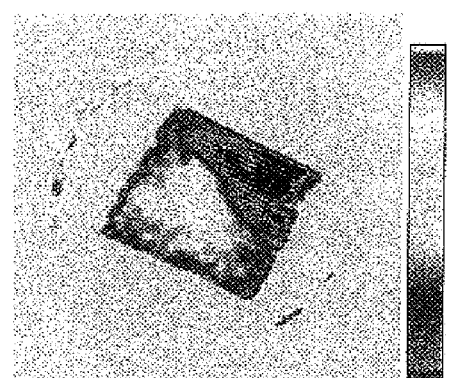
FIG. 33D is like FIG. 33C except the probe was placed at a different atherosclerotic area on the heart shown in FIGS. 33A-B.

An in vivo experiment was performed on an opened dog's heart. The dog was an animal model of human atherosclerosis that was developed by some of the inventors over a seven-year period, and was one of a group of unique fifth-generation dogs bred by carefully choosing their parents so that a higher probability will be obtained to develop atherosclerotic lesions on their vascular arteries. By feeding the dogs a high cholesterol diet for ten months, severe atherosclerotic plaques developed on their peripheral artery beds. The lesions are histologically very similar to human plaques. In two such dogs, which died of stroke, extensive lipid-laden atheroscleromas, mostly of the vulnerable types (i.e., type IV AHA classification). This animal model is ideal to study gene therapy or experimental treatment where access with a larger catheter is necessary. FIG. 33A is a routine visible photograph showing the well-developed lesions on the coronary artery. The same adapters used in the in vitro phantom experiment described above were employed in the animal test. Since the 6 mm diameter fiber bundle used in this experiment was too large to be inserted into the dog's coronary artery, the bundle was instead used outside the animal's body to collect the images in this study. The images clearly demonstrate that the temperature heterogeneity of the coronary artery of the developed animal model can be detected in vivo via the IR imaging fiber bundle. The IR image is shown in FIG. 33B, which clearly reveals that the temperatures along the coronary artery are highly heterogeneous. Comparing the visible with the IR image the extra information revealed by the IR image can be readily appreciated. Although one can see from the visible image the shining bead along the artery indicating the atherosclerotic plaques inside, the IR image clearly demonstrates the temperature heterogeneity and those inflammation sites. The visible images could easily be distorted by the blood, and are largely dependent on the lighting conditions in the operation room when the in vivo pictures are taken. IR images, to the contrary, are not affected by lighting conditions and blood colors. These advantages make IR imaging a valuable tool to detect plaque temperature heterogeneity in vivo. FIGS. 33C and 33D are sections of the coronary artery IR image obtained when the IR imaging fiber bundle was placed at different locations above the diseased artery. A similar study was conducted in a high cholesterol fed Watanabe rabbit animal model, and the in vivo infrared image is shown in FIG. 33E. In this case a 3 mm O.D. fiber bundle catheter was inserted near the rabbit aortic arch prior to tissue harvesting.

As previously noted, the temperature calibration of the camera is not valid after the adapters are added to the imaging system, as was the case in this study. In performing the calibration of the IR imaging system, there are a number of factors to be considered. First, a relay optics system is needed to efficiently couple the fiber bundle to the IR detector system. Secondly, the image must be calibrated pixel by pixel, since the individual fibers theoretically have different Modulation Transfer Functions (MTF). The other factors, such as dead pixels on the detector, dead fibers in the bundle, as well as the fill factors, are also taken into consideration. A simple phantom demonstrating temperature heterogeneity in a vessel has been built by the inventors for testing the C2 imaging bundle. This phantom consists of an approximately 10 cm long section of latex tubing, of various sizes to simulate different blood vessel diameters, surrounded by a fluid circulation and temperature control system. Micro heating elements are scattered along the latex tube to permit heating to different temperatures in order to generate the thermal heterogeneity. By varying the fluid circulation speed and volume, arterial blood flow is simulated. The temperature of the fluid is maintained at 37° C. with a constant temperature water bath. The catheter is tested using the phantom fluid set at temperatures ranging from 36° C. to 40° C., in 0.5° C. intervals. The micro heating elements create foci of 36.0° C.-40° C., in 0.5° C. intervals. This catheter is inserted through a catheter insertion port (CATH IN™) into the tube and withdrawn in 2 mm steps. At each step, the IR thermal image is recorded. When an occluding balloon is included on the catheter assembly, the thermal image is recorded after balloon inflation. The computer reconstructed image then maps the interior wall of the phantom vessel.

Temperature Calibration of the IR Fiber Imaging System

Ensuring the accuracy of remote sensing temperature measurement devices is more difficult that with most direct contacting devices, such as thermocouples and thermistors. Accuracy of less than 2% standard deviation is obtainable, however. Reproducibility is readily achieved with the IR catheters. For the purposes of most of the heat sensing methods described herein, measuring temperature heterogeneity (i.e., the spatial temperature distribution) rather than the absolute temperature of a site is of primary interest. Therefore, the high sensitivity (NEDT of 20 mK) and spatial resolution (<1 mm) of the IR fiber thermal imaging technology used advantageously. Initial calibration of the IR imaging bundle catheter is done with an aluminum block (painted black) at six different temperatures. The block is heated by a constant temperature water bath. The thermal images transmitted through each IR fiber is then fitted into a straight line pixel by pixel. The slope and Y-intercept are then used to calculate the temperature of other unknown images. Table 1 lists the temperature of the block as measured by thermistor and the predicted temperature of a 30×30 fiber array, as well as the standard deviation (SD).

TABLE 1

| Thermistor | IR Imaging Bundle | | | |
|---|---|---|---|---|
| ° C. | Mean (° C.) | SD | Max (° C.) | Min (° C.) |
| 42.5 | 43.1 | 0.09 | 43.5 | 42.9 |
| 39.5 | 39.0 | 0.08 | 39.3 | 38.7 |
| 38.8 | 38.8 | 0.10 | 39.2 | 38.2 |
| 36.6 | 36.2 | 0.08 | 36.5 | 35.9 |
| 34.8 | 43.2 | 0.08 | 34.4 | 33.9 |

The small diameter (i.e., 6 mm OD or less) IR catheters described above are useful tools for detecting temperature heterogeneity in vivo in this animal model and for subsequently monitoring particular plaques to follow-up on whether they progress or regress. For instance, a small diameter IR fiber bundle catheter is inserted into a coronary artery, and the temperature of a multiplicity of sites along the vessel wall of the dog are first measured to obtain a baseline temperature reading for each said site, employing the detector, processor, display and user interface as described above. The physical location of particular sites along the vessel wall and its temperature are recorded. The catheter is then removed from the animal and the animal is maintained or treated according to the desired protocol. At a later time, a similar catheter is reinserted into the vessel and the temperature measurements are repeated. By determining whether there is a temperature difference between adjacent sites, and/or between the first and subsequent readings for a particular site and its corresponding baseline temperature valuable information about the condition of the vessel wall can be ascertained. Such information could include ascertaining the natural history of a plaque region, i.e., whether it progresses to become a hotter, more vulnerable site, whether it becomes cooler, indicating that a warm, inflamed site has become less inflamed or resolved completely, or whether a new, elevated temperature plaque has developed where there was previously a normal temperature reading. The efficacy of a therapeutic regimen can be evaluated similarly in this animal model and a small diameter IR fiber bundle catheter system.

Figure 34B:
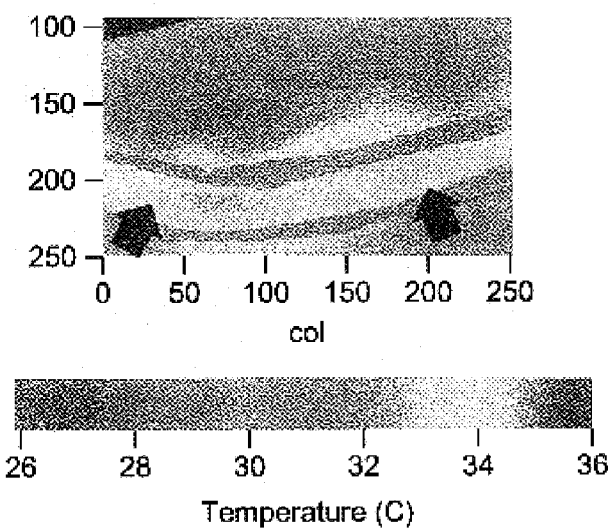
FIG. 34B is another infrared photograph like FIG. 34A, except the graft is from another patient with renal failure.

Detection and Non-invasive Monitoring of In Vivo Inflammation in a Human AV Graft Temperature heterogeneity of plaques can also be detected in vivo in hemodialysis patients with arteriovenous (AV) grafts by externally applied infrared thermography. Typically, the incidence of stenosis which is attributable to inflammation, thrombosis and fibrosis in the first postoperative year after graft implantation is about 50-60% (see Berkowitz et al. *J. Vasc Surg* 15:130-41(1992) [and the discussion at 141-2 of that reference]; Harris, et al. *Br J Surg* 74:252-5 (1987); and Tordoir et al. *Eur J Vasc Surg* 2:3-7 (1988)). The inventors found that grafts are subcutaneous and superficial enough that their heat can be detected by an infrared camera. In images obtained from six patients undergoing hemodialysis, it considerable temperature heterogeneity was found. An infrared photograph of a representative prosthetic AV hemodialysis graft taken from dialysis patient with renal failure is shown in FIG. 34A. This image demonstrates the temperature heterogeneity of the superficial AV graft. The dashed green strip visible in the lower right corner of the photograph is part of the bandage. This graft, which had good flow and no palpable lesions or palpable temperature heterogeneity, revealed fine temperature heterogeneity by infrared, as indicated by the arrows, when infrared temperature measurements were made using an IR imaging camera as described above. The mean temperature on the arterial side of the graft was 34.26° C.±0.93 vs. 35.03° C.±0.62 on the venous side (p<0.0001). The inventors suggest that this may reflect inflammation and/or cell proliferation, both of which are typically pronounced at the venous anastomosis. Analysis of 19 patients (mean age 46 years) showed that graft flow was inversely related to graft age and patient age. FIG. 34B is another representative infrared photograph of the prosthetic AV hemodialysis graft of another patient with renal failure also showing temperature heterogeneity in the graft.

Figure 35:
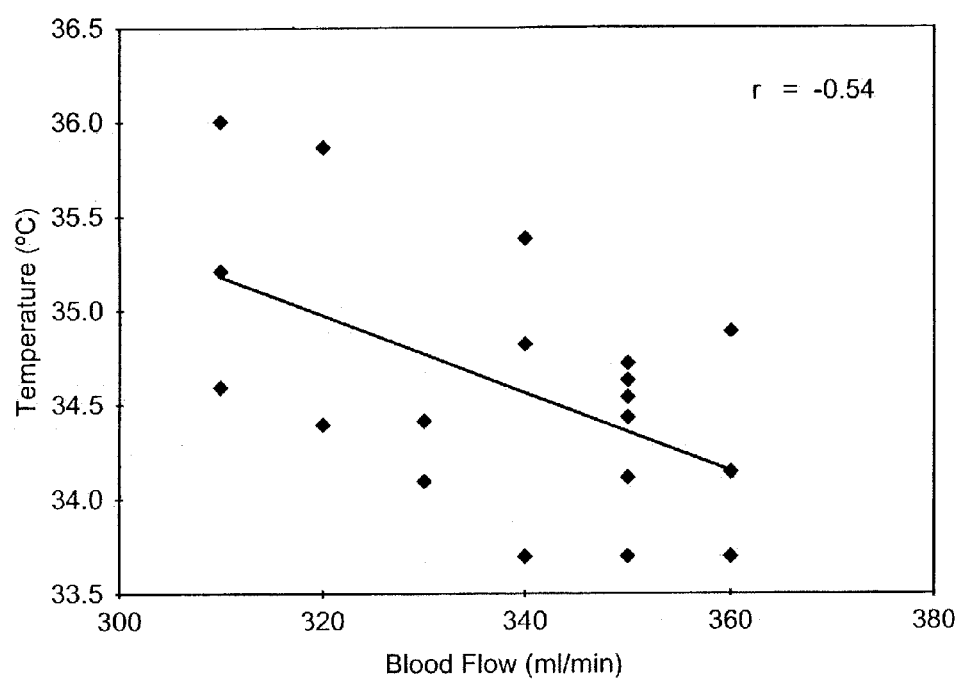
FIG. 35 is a graph showing the inverse relationship between blood flow through a graft and the graft temperature in grafts like those depicted in FIGS. 34A and 34B.

A surprising finding in this investigation was that flow was not proportional to the heat measured at the venous end, as would ordinarily be expected since heat causes vasodilation and vasoconstriction reduces surface heat. Instead, as shown in FIG. 35, graft heat and flow, were inversely related (r=−0.54), consitent with the inventors suggestion that inflammation and cell proliferation are generating heat. The regions of elevated temperature visualized by infrared thermometry, suggest that appreciable clustering of activated inflammatory cells has occurred at those sites. Accordingly, a conventional externally applied infrared imaging camera is employed to non-invasively detect and quantify, plaque temperature heterogeneity (in the range of about 0.4 to 4° C.) in a living patient, and to follow its natural course and outcome after intervention.

Non-Invasive Detection of Plaques at Risk

Infrared catheters, thermocouple and thermistor catheters are best suited for use in patients who are already known to have cardiovascular disease and are undergoing catheterization. A minimally invasive catheter-based device is presently preferred for use in the coronary arteries, as well as other arteries in the body. However, for imaging temperatures in carotid and femoral arteries in particular, a non-invasive method is preferred for screening people who are not known to be sick. To this end, other techniques conventionally used for unrelated purposes may also be used for detecting hot plaque in a vessel.

One such alternative non-invasive technique is thermal magnetic resonance imaging. As discussed above with respect to alternative catheter-based techniques for detecting vulnerable plaque, magnetic resonance spectroscopy has been used by others to identify some histochemical features of atherosclerotic lesions (Mohiaddin et al., id; Vinitski et al., id.; Trouard et al. id.; von Ingersleben et al. *Radiographics* 17:1417-23 (1997); Yuan et al. *Arterioscler Thromb Vasc Biol* 17:1496-503 (1997); and Pearlman et al. *Magn Reson Med* 7:262-79 (1988)). Several groups of investigators have adapted magnetic resonance to monitor the temperature of tumors after whole body hyperthermia (Stollberger et al. *J Magn Reson Imaging* 8:188-96 (1998); Kuroda et al. *Magn Reson Med* 38:845-51 (1997); MacFall et al. *Med Phys* 23:1775-82 (1996); Ishihara et al. *Magn Reson Med* 34:814-23 (1995); and Altbach et al. *Magn Reson Med* 20:319-26 (1991)). Temperature alters T-1 and T-2 relaxation times of both water and lipids, and alters the resonant frequency of water attributable to variations in the molecular screening effects of electron clouds surrounding water protons. Others have demonstrated that implanted thermocouples correlate with T-1 relaxation time (Dickinson et al. *J Comput Assist Tomogr* 10:468-72 (1986). The temperature-sensitive parameters that are measurable in MR experiments include the longitudinal and transverse relaxation times (T-1 and T-2), the molecular diffusion coefficient (D), and the proton chemical shift. In the case of relaxation times, the changes in T-1 and T-2 are tissue-specific and can often be difficult to measure reliable, i.e., different tissues have different relaxation parameters and their relative dependence on temperature changes is also different. On the other hand, for a specific tissue type such as plaque, the changes in the relaxation times may be a useful parameter to measure. While the measurement of molecular diffusion coefficient (D) can be used as a thermometer, the diffusion weighted imaging techniques are extremely sensitive to bulk motion caused by physiologic activity, such as respiration and blood flow. Finally, the rupture or bending of hydrogen bonds has been attributed as the mechanism for the change in chemical shift associated with alterations in local temperature. This chemical shift change is independent of tissue type and presents a unique advantage when compared to techniques that rely on changes in relaxation times. The measurement errors that can confound the chemical shift-based results include primarily the following factors: (a) system drifts or instabilities, (b) magnetic field heterogeneity, (c) motion and/or blood flow within the vessels, and (d) temperature dependence difference between different tissues. While these potential confounders are formidable challanges, it is possible to develop methods that minimize the effect of these artifacts, as similarly demonstrated by others Hentschel et al. *Int J Hyperthermia* 14:479-93 (1998); Frenzel et al. *Magn Reson Med* 35:364-9 (1996): Wlodarczyk et al. *J Magn Reson Imaging* 8:165-74 (1998)). In continuing the development of this non-invasive MRT technique, the inventors expect to use shimming techniques to minimize field perturbations, use navigator and ECG-based gated techniques to minimize the effect of motion, to develop techniques to reliably measure the system drift during the acquisition, and to develop specific methods to assess the temperature dependence differences between target tissues such as vulnerable vs. stable atherosclerotic plaque.

Figure 36A:
FIG. 36A is a magnetic resonance image of the leg of a living subject showing in vivo temperature changes in response to an ice pack applied to the calf.
Figure 36B:
FIG. 36B is a graph showing the variation of relative signal intensity with respect to time during the magnetic resonance thermography test of FIG. 36A.

In preliminary investigations in the inventors' laboratories, new pulse sequences for thermal magnetic resonance imaging were developed. FIGS. 36A,B illustrate the results of a test of the sensitivity of thermal sequences to temperature changes in vivo. In this test, a human subject placed his leg in an extremity coil overlying a plastic package containing ice cubes. Single shot last spin-echo sequences were obtained in the sagittal plane at one minute sampling intervals. FIG. 36A is a magnetic resonance image showing the level regions of the calf in which relative signal intensity was measured over increasing time. A graph of signal intensity vs time is shown in FIG. 36B. It can be readily seen in FIG. 36A that there is a rapid loss of signal at position (g) just beneath tie ice cube indicating loss of signal due to cooling. At positions (h) and (i), which are remote to the ice cubes, signal intensity increases, possibly due to hyperemia and warming of tissues in reaction to adjacent cooling. The dramatic differences in signal intensity demonstrated in this study illustrate that MRI pulse sequence can measure temperature changes in vivo independent of effects on flow in lipid-containing tissues.

Inflammatory cells avidly consume glucose and lactate. Thus, an alternative technique for non-invasively detecting foci of inflammatory cells in the vessel wall is or $^{14}$C-lactate positron emission tomatography (PET). $^{18}$fluorodeoxyglucose PET has been reported by others to image inflamed lymph nodes. See Scharki at al *PNAS USA* 93:6425-6430 (1996), the disclosure of which is incorporated herein by reference to the extent that it provides materials and methods not set forth herein. A disadvantage of PET techniques is that they involve high-energy radiation, expensive equipment and proximity of a facility with cyclotron.

Similar techniques employing computed infrared tomography could be developed for detecting vulnerable plaque, possibly in conjunction with interferometry, in which an incident beam is split by a moving mirror to produce a reference beam and a beam that is variably scattered and absorbed by the tissue of the vessel wall. The nonsynchronous reflected wavelengths are reconstituted to reveal structural detail with 20-μm resolution. See Benaron, et al., *Science* 259:1463-1466 (1993) and Brezinski, et al., *Circulation* 92:1-149 (1995). With these techniques thermal resolution and spatial resolution are as low as 10 μm.

Another non-invasive technique for imaging temperature heterogeneity in a living vessel is ultrasound thermal imaging. Thermal resolution of approximately 1.0° C. using non-invasive ultrasound thermal imaging prototypes has been described by others. Thermal techniques will very likely be combined with ultrasound catheters, or newer techniques such as optical coherence tomography to provide both functional and anatomic information. See Brezinski, et al. *Circulation* 93:1206, 13 (1996); Brezinski et al. *J. Surg Res* 71:32-40 (1997); Brezinski et al. *Heart* 77:397-403 (1997), and Brezinski et al. *Am J Cardiol* 77:92-3 (1996).

Other alternative non-invasive techniques include imaging the inflammatory cells with gallium, (Pasterkamp, et al., *Circulation* 91:1444-1449 (1995)), and use of radiolabeled anti-macrophage antibody fragments.

Still other techniques typically denote anatomy (e.g., CT or ultrasound), require angiographic contrast and radiation (e.g., angiography) or a radioactive tracer (e.g., nuclear imaging, as with a thallium or sesta MIBI scan) or require injection of a dye or other marker, together with blood sampling (e.g., green-dye dilution by the Fick principle). Similar information might be obtained by positron emission tomography, which can be used to determine flow and metabolism (with 18-fluorodeoxyglucose).

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, the methods and devices described above are exemplified primarily by their use in a blood vessel or artery. However, they are also applicable for any other cavity or tube inside the body, such as a synthetic graft, in which one might want to measure temperature as a sign of inflammation, infection, cancer or vulnerable plaque. All such modifications are intended to be included within the scope of the appended claims.

What is claimed is:

1. A thermal sensor basket catheter for detecting temperature heterogeneity of plaque along a vessel wall, comprising:
a catheter having a proximal end and a distal end;
an expandable basket at said distal end of said catheter, said expandable basket formed by at least four hollow channels and having proximal and distal ends, each said channel comprising a thermally conductive material and having a vessel wall-contacting side, a lumen-facing side, and a terminus;
a hollow shaft joined to said proximal end of said expandable basket;
a tip joined to said distal end of said expandable basket, wherein at least one said channel terminus is moveably enclosed inside said tip;
a thermal sensor disposed on the vessel wall-contacting side of each said channel at a point about mid-way between said basket proximal and distal ends, said thermal sensor comprising a thermocouple junction in thermal contact with said vessel wall-contacting side and thermally insulated from said lumen-facing side;
a pair of insulated wires in electrical contact with each said thermal sensor and extending from said thermal sensor through said proximal end and through said hollow shaft; and
a signal processor coupled to said proximal end of said catheter and in communication with said one or more thermal sensors, said processor being capable of receiving thermal information from said one or more thermal sensors and differentiating the different types of plaque based on the thermal information received.

2. The thermal sensor basket catheter of claim 1 wherein each said terminus is moveably enclosed inside said tip.

3. The catheter of claim 1 further comprising a thermally insulating material disposed inside each said channel between said junction and said lumen-facing side.

4. The thermal sensor basket catheter of claim 1 further comprising a microcontroller coupled to the signal processor and programmed to analyze thermal information received from the thermal sensors.

5. The thermal sensor basket catheter of claim 4 wherein the microcontroller is programmed to determine a thermal heterogeneity score for the plaque.

6. The thermal sensor basket catheter of claim 4 wherein the microcontroller is programmed to determine skewness of temperature for the plaque.

7. An intravascular thermocouple catheter assembly for detecting temperature heterogeneity along a vessel wall, said assembly comprising:

the thermal sensor basket catheter of claim 1; and a guiding catheter having a guiding lumen adapted for slidingly receiving said thermal sensor basket catheter.

8. The assembly of claim 7 wherein said guiding catheter further comprises an inflatable occluding balloon and an inflation lumen in communication with said balloon.

9. The assembly of claim 7 further comprising an intravascular ultrasound wire.

10. The assembly of claim 7 further comprising a microcontroller coupled to the signal processor and programmed to analyze thermal information received from the thermal sensors.

11. The assembly of claim 10 wherein the microcontroller is programmed to determine a thermal heterogeneity score for the plaque.

12. The assembly of claim 10 wherein the microcontroller is programmed to determine skewness of temperature for the plaque.

13. A thermal sensor basket catheter for detecting temperature heterogeneity of plaque along a vessel wall, comprising:

a catheter having a proximal end and a distal end;

an expandable basket at said distal end of said catheter, said expandable basket formed by at least four hollow channels and having proximal and distal ends, each said channel having a vessel wall-contacting side, a lumen-facing side, and a terminus;

a hollow shaft joined to said proximal end of said expandable basket;

a tip joined to said distal end of said expandable basket, wherein at least one said channel terminus is moveably enclosed inside said tip;

a thermal sensor disposed on the vessel wall-contacting side of each said channel at a point about mid-way between said basket proximal and distal ends;

a pair of insulated wires in electrical contact with each said thermal sensor and extending from said thermal sensor through said proximal end and through said hollow shaft; and a detector coupled to said proximal end of said catheter and in communication with said one or more thermal sensors, said detector being capable of receiving thermal information from said one or more thermal sensors and differentiating the different types of plaque based on the thermal information received.

14. The catheter of claim 13 wherein said thermal sensors comprise thermistors.

15. The catheter of claim 13 wherein each said terminus is moveably enclosed inside said tip.

16. The catheter of claim 13 wherein each of said channels further comprises a thermally conductive material.

17. The catheter of claim 13 further comprising a thermally insulating material disposed inside each said channel between said junction and said lumen-facing side.

18. An intravascular thermocouple catheter assembly for detecting temperature heterogeneity along a vessel wall, said assembly comprising:

the thermal sensor basket catheter of claim 13; and a guiding catheter having a guiding lumen adapted for slidingly receiving said thermal sensor basket catheter.

19. The assembly of claim 18 wherein said guiding catheter further comprises an inflatable occluding balloon and an inflation lumen in communication with said balloon.

20. The assembly of claim 18 further comprising an intravascular ultrasound wire.

\* \* \* \* \*

UNITED STATES PATENT AND TRADEMARK OFFICE
CERTIFICATE OF CORRECTION

PATENT NO. : 7,426,409 B2
APPLICATION NO. : 10/212860
DATED : September 16, 2008
INVENTOR(S) : S. Ward Casscells, III et al.

It is certified that error appears in the above-identified patent and that said Letters Patent is hereby corrected as shown below:

Please delete the sentence at Column 1, line 15 of U.S. Patent No. 7,426,409 and insert the following sentence:

--This invention was made with government support under contract number DAMD17-98-18002 awarded by the United States Army. The government has certain rights in the invention.--

Signed and Sealed this

Twenty-second Day of September, 2009

David J. Kappos
*Director of the United States Patent and Trademark Office*